United States Patent [19]

Kelly et al.

[11] 4,054,737

[45] Oct. 18, 1977

[54] THROMBOXANE B ANALOGS

[75] Inventors: Robert C. Kelly, Kalamazoo; Norman A. Nelson, Galesburg, both of Mich.

[73] Assignee: The Upjohn Company, Kalamazoo, Mich.

[21] Appl. No.: 716,449

[22] Filed: Aug. 20, 1976

[51] Int. Cl.² .................. C07D 309/36; C07D 309/38
[52] U.S. Cl. ................................ 542/413; 260/343.6; 260/343; 260/343.3 R; 260/343.5; 260/345.6; 260/345.7 R; 260/345.8 P; 260/410; 260/345.9 P; 260/395; 260/514 D; 260/535 R; 424/283; 424/279; 424/285; 542/400; 542/426; 542/427; 560/55
[58] Field of Search ............ 260/240 R, 345.7, 345.8, 260/345.8 P, 345.9, 345.9 P

[56] References Cited

U.S. PATENT DOCUMENTS

| | | | |
|---|---|---|---|
| 2,923,861 | 12/1975 | Nelson | 260/240 R |
| 3,864,387 | 2/1975 | Nelson | 260/346.2 R |
| 3,931,279 | 1/1976 | Nelson | 260/345.8 P |

OTHER PUBLICATIONS

Malmsten et al., Proc. Nat. Acad. Sci. U.S.A. 72 (1975), pp. 1446–1452.
Hamberg et al., Chem. Abst. 82 (1975), No. 2147.

*Primary Examiner*—Arthur P. Demers
*Attorney, Agent, or Firm*—Robert A. Armitage

[57] ABSTRACT

The present specification provides novel intermediates and novel processes for the synthesis of various side chain and skeletal analogs of Thromboxane $B_2$ ($11\beta$-homo-11a-oxa-$PGF_{2\alpha}$). These analogs are particularly and especially useful as reproductive cycle control agents.

54 Claims, No Drawings

THROMBOXANE B ANALOGS

BACKGROUND OF THE INVENTION

The present invention provides novel intermediates and chemical processes which are useful in preparing side chain and skeletal analogs of Thromboxane $B_2$ ($TXB_2$).

Some material essential to disclosure of the present invention is incorporated here by reference from Ser. No. 676,890, filed Apr. 14, 1976, now issued as U.S. Pat. No. 4,020,173, on Apr. 26, 1977, as hereinafter indicated.

Thromboxane $B_2$ has the structure:

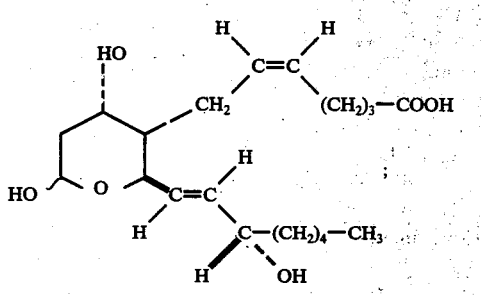

and can be considered as a derivative of thromboxanoic acid or 11a-homo-11a-oxa-prostanoic acid which has the following structure and carbon atom numbering:

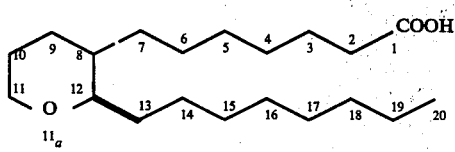

A systematic name for thromboxanoic acid is 7-[2β-octyltetrahydropyran-3α-yl]-heptanoic acid.

By way of comparison prostanoic acid has the structure and carbon atom numbering

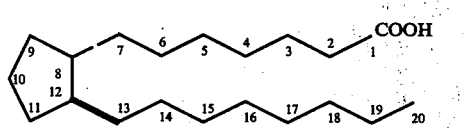

and systematic name: 7-[2β-octyl-cyclopenta-1α-yl]-heptanoic acid.

Alternatively Thromboxane $B_2$ is named as an analog of $PGF_{2\alpha}$, i.e., 11a-homo-11a-oxo-$PGF_{2\alpha}$.

In the above formulas, as well as in the formulas hereinafter given, broken line attachments to a tetrahydropyran ring or cyclopentane indicate substituents in alpha configuration i.e., below the plane of the ring. Heavy solid line attachments to a tetrahydropyran ring or cyclopentane indicate substituents in beta configuration, i.e., above the plane of the ring. The use of wavy lines (~) herein will represent attachment of substituents in either the alpha or beta configuration or attachment in a mixture of alpha and beta configurations. See especially the discussion below pertaining to anomeric mixtures.

The side-chain hydroxy at C-15 in the above formula of $TXB_2$ is in S configuration. See, Nature 212, 38 (1966) for discussion of the stereochemistry of the prostaglandins, which discussion applies hereto with respect to $TXB_2$. Expressions such as C-15, and the like, refer to the carbon atom in the thromboxane- or prostaglandin-type compound which is in the position corresponding to the position of the same number in thromboxanoic acid or prosanoic acid, respectively.

Molecules of the known prostaglandins each have several centers of asymmetry, and can exist in racemic (optically inactive) form and in either of the two enantiomeric (optically active) forms, i.e. the dextrorotatory and levorotatory forms. Likewise, $TXB_2$, which as discussed above is alternatively nominated as 11a-homo-11a-oxo-$PGF_{2\alpha}$, has similar centers of asymmetry, and thus, likewise can exist in optically active or racemic form. As drawn, the above formula represents the particular optically active form of the $TXB_2$ as is obtained biosynthetically, for examples, as obtained by Samuelsson, Proc. Nat. Acad. Sci. USA 71, 3400–3404 (1974). The mirror image of each of these formulas represents the other enantiomer of $TXB_2$. The racemic form of $TXB_2$ contains equal numbers of both enantiomeric molecules, and one of the above formulas and the mirror image of that formula is needed to represent correctly racemic $TXB_2$. For convenience hereinafter, use of the term, thromboxane or "TX" or "TXB" will mean the optically active form of that thromboxane-type compound thereby referred to with the same absolute configuration as $TXB_2$ obtained biosynthetically by Samuelsson. When reference to the racemic form of a thromboxane-type compound is intended, the word "racemic" or "dl" will precede the name, e.g., dl-$TXB_2$.

The term "thromboxane intermediate" as used herein, refers to any cyclopentane or tetrahydropyran derivative or acyclic compound which is useful in preparing the various skeletal or side chain analogs of $TXB_2$.

When a formula, as drawn herein, is used to depict a thromboxane intermediate each such formula represents the particular stereoisomer of the thromboxane intermediate which is useful in preparing the TXB analog of the same relative stereochemical configuration as $TXB_2$ obtained biosynthetically.

The term "thromboxane-type" (TX-type) product, as used herein, refers to each of the various tetrahydropyran derivatives herein which are useful for at least one of the same pharmacological purposes as the $TXB_2$, as indicated herein.

The formulas, as drawn herein, which depict a thromboxane-type product, each represent the particular stereoisomer of the thromboxane-type product which is of the same relative stereochemical configuration as $TXB_2$ obtained biosynthetically.

The term "thromboxane analog", as used herein, represents that stereoisomer of a thromboxane-type product which is of the same relative stereochemical configuration as $TXB_2$ obtained biosynthetically or a mixture comprising that stereoisomer and the enantiomer thereof. In particular, where a formula is used to depict a thromboxane-type compound herein, the term thromboxane analog refers to the compound of that formula, or a mixture comprising that compound and the enantiomer thereof.

With respect to the asymmetric C-11 position of $TXB_2$ and the various hemiacetal analogs thereof herein, the hemiacetal structure about C-11 results in the presence of two diastereiomeric forms: the α-hydroxy and β-hydroxy anomers. Dye to the mutarotation resulting from the conversion of $TXB_2$ or the hemiacetal analogs thereof to the hydroxy-aldehyde form, e.g.

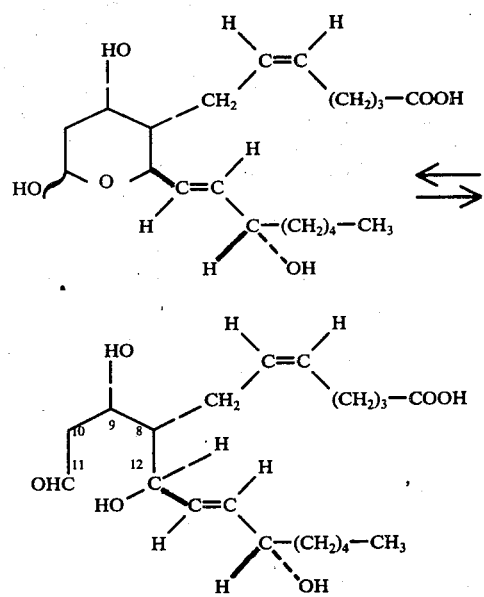

the 11-hydroxy represents an equilibrium mixture of alpha and beta hydroxy anomers in aqueous and certain other solutions, depicted by a ∼ OH, herein.

In formulas herein (e.g., formula IV) where a cyclopentane or tetrahydropyran ring is not present, such a ring having been cleaved or to be introduced in subsequent reaction steps, the convention by which substituents about asymmetric centers are depicted as alpha or beta is as defined above, but with respect to the plane of the various atoms which comprised said ring before its cleavage or will comprise said ring as synthesized in subsequent reaction steps. Thus, for example, in formula IV the oxygen atom of the 12-hydroxy substituent, having formerly been or successively to be the 11a-oxa of the tetrahydrofuran ring is viewed as planar with C-8 to C-11 and C-12. Accordingly the C-12 side chain is beta to this plane and thus rendered by a heavy solid line, while the C-12 hydrogen is alpha to this plane and thus rendered by a dotted line.

Thromboxane $B_2$ is known in the art. This compound is prepared biosynthetically from arachadonic acid by B. Samuelsson, Proc. Nat. Acad. Sci. U.S.A. 71, 3400–3404 (1974). This compound alternately is named by him as 8-(1-hydroxy-3-oxopropyl)-9,12L-dihydroxy-5,10-heptadecadienoic acid, hemiacetal or PHD.

$TXB_2$ is produced biosynthetically from arachadonic acid, employing the cyclic oxygenase system which is responsible for the production of prostaglandins from arachadonic acid.

$TXB_2$, 15-epi-$TXB_2$, their 11-(lower alkyl) acetals, acceptable salts have been discovered to be extremely potent in causing various biological responses. For that reason, these compounds (hereinafter $TXB_2$ compounds) have been found to be useful for pharmacological purposes.

These biological responses include:

a. stimulating smooth muscle (as shown by tests on guinea pig ileum, rabbit duodenum, or gerbil colon); and more especially and particularly b. affecting the reproductive organs of mammals as labor inducers, abortifacients, cervical dilators, regulators of the estrus, and regulators of the menstral cycle.

Because of these biological responses, these $TXB_2$ compounds are useful to study, prevent, control, or alleviate a wide variety of diseases and undesirable physilogical conditions in birds and mammals, including humans, useful domestic animals, pets, and zoological specimens, and in laboratory animals, for example, mice, rats, rabbits, and monkeys.

These $TXB_2$ compounds, being extremely potent in causing stimulation of smooth muscle, are also highly active in potentiating other known smooth muscle stimulators, for example, oxytoxic agents, e.g., oxytocin, and the various ergot alkaloids including derivatives and analogs thereof. Therefore, these compounds for example, are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the $TXB_2$ compound is administered by intravenous infusion immediately after abortion or delivery at a dose in the range about 0.01 to about 50μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The $TXB_2$ compounds, being useful in place of oxytocin to induce labor, are used in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The compounds are further useful for controlling the the reproductive cycle in menstruating female mammals, including humans. Menstruating female mammals are those mammals which are mature enough to menstruate, but not so old that regular menstruation has ceased. For that purpose the $TXB_2$ compound is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by thromboxanes is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the $TXB_2$ compound is administered locally or systemically.

$TXB_2$, for example, is administered orally or vaginally at doses of about 5 to 200 mg. per treatment of an adult female human, with from one to five treatments per 24 hour period. Alternatively $TXB_2$ is administered intramuscularly or subcutaneously at doses of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The $TXB_2$ compound is injected or applied in a feed at doses of 0.1–100 mg. per animal and may be combined with other agents such as steroids. Dosing schedules will depend on the species treated. For example, mares are given the $TXB_2$ compound 5 to 8 days after ovulation and return to estrus. Cattle, are treated at regular intervals over a 3 week period to advantageously bring all into estrus at the same time.

Certain 11-oxaprostaglandin-type compounds described above are known in the art. See Belgian Pat. No. 830,423 (Derwent Farmdoc CPI No. 01971X) and Tetrahedron Letters 43:3715–3718 (1975).

SUMMARY OF THE INVENTION

The present specification provides novel intermediates and processes for the production of $TXB_2$ and side chain and skeletal analogs of $TXB_2$. In particular, there are disclosed herein novel processes in the Charts herein.

In particular the present specification discloses:

a. a process for preparing a thromboxane intermediate of the formula

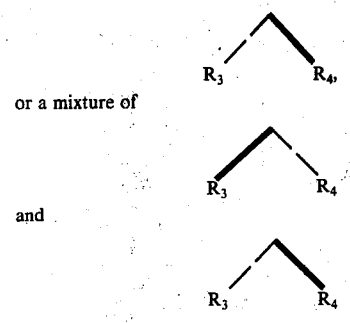

wherein $R_{33}$ is alkyl of one to 4 carbon atoms, inclusive; wherein $L_1$ is

or a mixture of

and

wherein $R_3$ and $R_4$ are hydrogen, methyl, or fluoro, being the same or different, with the proviso that one of $R_3$ and $R_4$ is methyl only when the other is hydrogen or methyl;

wherein $R_7$ is $-(CH_2)_m-CH_3,$  (1)

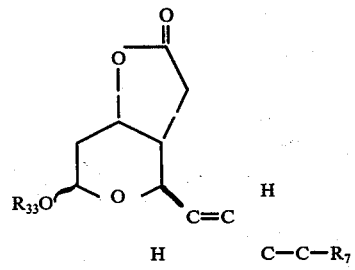, or

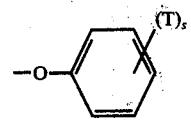 (3)

wherein 1 is zero, one, two, or three; wherein m is one to 5, inclusive, T is alkyl of one to 3 carbon atoms, inclusive, alkoxy of one to 3 carbon atoms, inclusive, chloro, fluoro, or trifluoromethyl, and s is one, two, or 3, the various T's being the same or different, with the further proviso that $R_7$ is

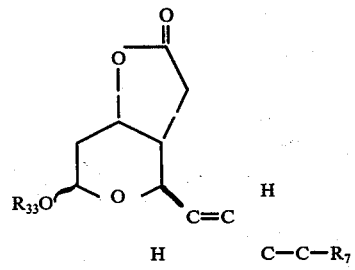

only when $R_3$ and $R_4$ are hydrogen or methyl, being the same or different;

which comprises:

1. Wittig oxoalkylating a thromboxane intermediate of the formula

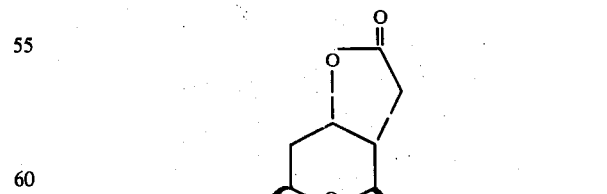

wherein $R_{33}$ is as defined above;

b. a process as in part (a) which further comprises:

2. hydrogenating the reaction product of step (1) of part (a), thereby preparing a thromboxane intermediate of the formula

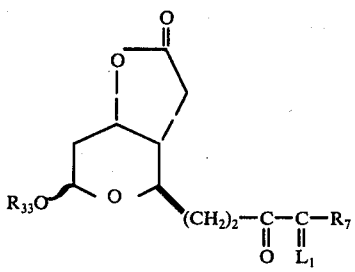

wherein $R_{33}$, $L_1$, $R_7$ are as defined above;
c. a process for preparing a thromboxane intermediate of the formula

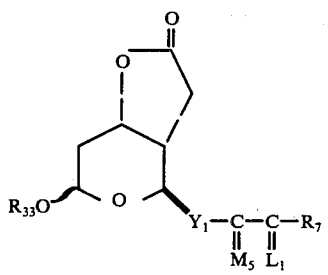

wherein $L_1$, $R_7$, and $R_{33}$ are as defined above;
wherein $Y_1$ is trans—CH=CH— or —$CH_2CH_2$—; and
wherein $M_5$ is

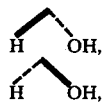

or a mixture of

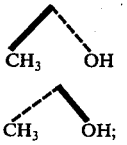

and which comprises:
1. reducing and separating epimeric alcohols or alkylating a thromboxane intermediate of the formula

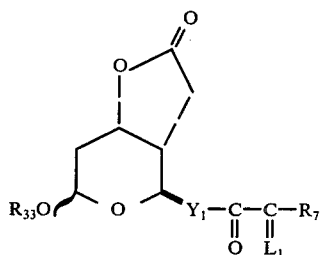

or

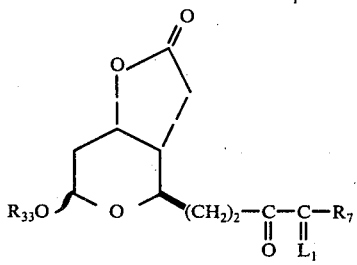

wherein $R_{33}$, $L_1$, and $R_7$ are as defined above.
d. a process as in part (c) which further comprises:
2. reducing the reaction product of step (1) of part (c) to a lactol, thereby preparing a thromboxane intermediate of the formula

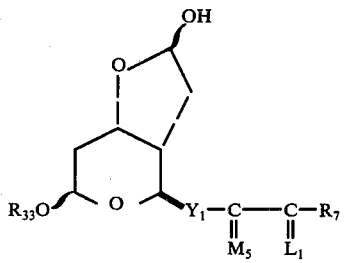

wherein $R_{33}$, $Y_1$, $M_5$, $L_1$, and $R_7$ are as defined above;
e. a process as part (j) which further comprises:
3. reducing to a primary alcohol the reaction product of step (3) of part (j), thereby preparing a thromboxane intermediate of the formula

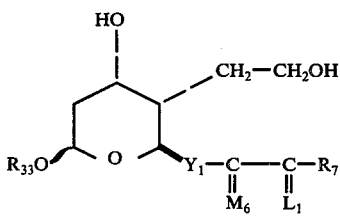

wherein $R_{33}$, $Y_1$, $L_1$, and $R_7$ are as defined above and $M_6$ is as defined in part (i);
f. a process as in part (e) which further comprises:
4. ortho carboxyalkylesterifying the reaction product of step (3) part (e) hydrolyzing the ortho ester; and optionally saponifying, reesterifying, or neutralizing with base, thereby preparing a thromboxane analog of the formula

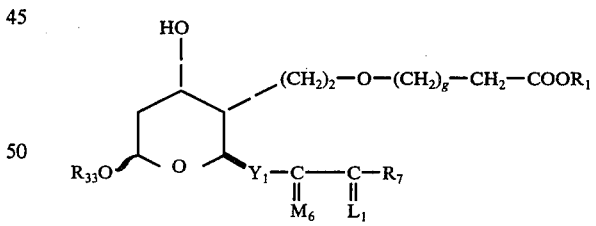

wherein g is one, two, or 3;
wherein $R_1$ is alkyl of one to 12 carbon atoms, inclusive, cycloalkyl of 3 to 10 carbon atoms, inclusive, aralkyl of 7 to 12 carbon atoms, inclusive, phenyl, phenyl substituted with one or two chloro, fluoro, or alkyl of one to 4 carbon atoms, inclusive, or a pharamcologically acceptable cation; and
wherein $R_{33}$, $Y_1$, $M_6$, $L_1$, and $R_7$ are as defined above;
g. a process as in part (d), which further comprises:
3. Wittig carboxyalkylating and optionally esterifying or neutralizing with base the reaction product of step (2) of part (d), thereby preparing a thromboxane analog of the formula

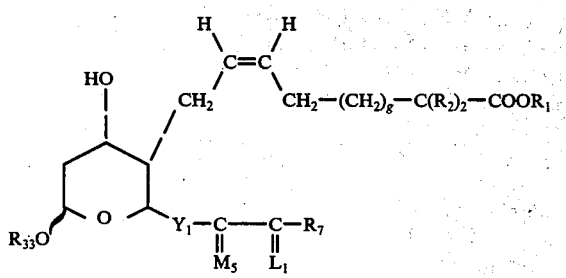

wherein $R_2$ is hydrogen or fluoro; and
wherein g, $R_1$, $R_{33}$, $Y_1$, $M_5$, $L_1$, and $R_7$ are as defined above.

h. a process according to part (g), which further comprises:

4. hydrogenating the cis-unsaturation of the reaction production of step (3) of part (g), thereby preparing a thromboxane analog of the formula

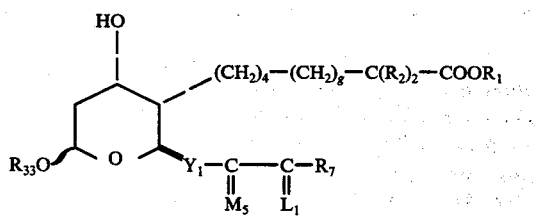

wherein g, $R_1$, and $R_2$, $R_{33}$, $Y_1$, $M_5$, $L_1$, and $R_7$ are as defined above;

i. a process according to part (c), which further comprises:

2. etherifying the reaction product of step (1) of part (c), thereby preparing a thromboxane intermediate of the formula

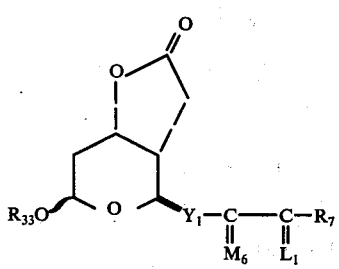

wherein $M_6$ is

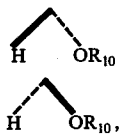

or a mixture of

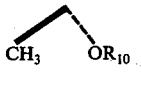

and

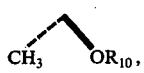

wherein $R_{10}$ is a blocking group; and
wherein $R_{33}$, $Y_1$, $M_6$, $L_1$, and $R_7$ are as defined above;
j. a process as in part (i), which further comprises:

3. reducing to a lactol the reaction product of step (2) of part (i), thereby preparing a thromboxane intermediate of the formula

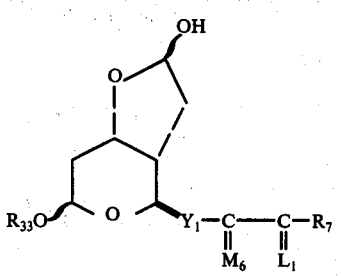

wherein $M_6$, $R_{33}$, $Y_1$, $L_1$, and $R_7$ are as defined above.

k. a process as in part (j), which further comprises:

4. Wittig alkylating the reaction product of step (3) of part (j), thereby preparing a thromboxane intermediate of the formula

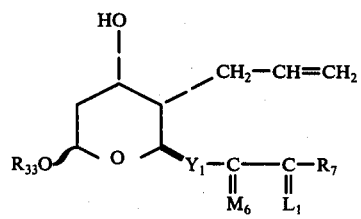

wherein $R_8$, $R_{33}$, $Y_1$, $L_1$, and $R_7$ are as defined above;

l. a process as in part (k) which further comprises:

5. primary hydroxylating the reaction product of step (4) of part (k), thereby preparing a thromboxane intermediate of the formula

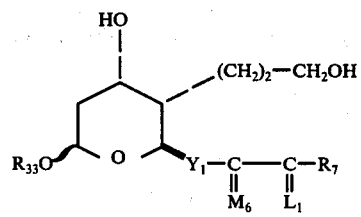

wherein $M_6$, $R_{33}$, $Y_1$, $L_1$, and $R_7$ are as defined above;

m. a process as in part (1), which further comprises:

6. silylating the reaction product of step (5) of part (1), thereby preparing a thromboxane intermediate of the formula

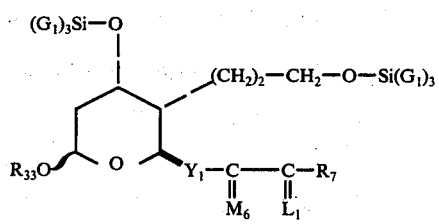

wherein $G_1$ is alkyl of one to 4 carbon atoms, cycloalkyl of 3 to 10 carbon atoms, inclusive, aralkyl of 7 to 12 carbon atoms, phenyl, or phenyl substituted with one or 2 fluoro, chloro, or alkyl of one to 4 carbon atoms, with the proviso that in the $-Si(G_1)_3$ moiety the various $G_1$'s are the same or different; and
wherein $M_6$, $R_{33}$, $Y_1$, $L_1$, and $R_7$ are as defined above.

n. a process as in part (m), which further comprises:

7. selectively oxidizing to an aldehyde the reaction product of step (6) of part (m), thereby preparing a thromboxane intermediate of the formula

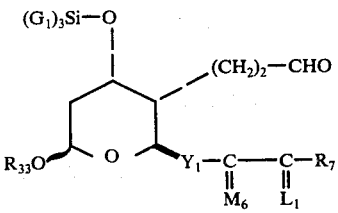

wherein $G_1$, $M_6$, $R_{33}$, $Y_1$, $L_1$, and $R_7$ are as defined above.

o. a process as in part (n), which further comprises:

8. hydrolyzing the reaction product of step (7) of part (n), thereby preparing a thromboxane intermediate of the formula

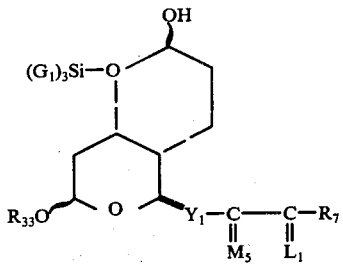

wherein $M_6$, $R_{33}$, $Y_1$, $L_1$, and $R_7$ are as defined above;

p. a process as in part (o), which further comprises:

9. Wittig carboxyalkylating and optionally esterifying or neutralizing with base the reaction product of step (8) of part (o), thereby preparing a thromboxane analog of the formula

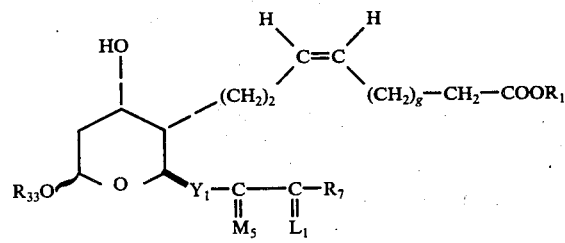

wherein g, $R_1$, $R_{33}$, $Y_1$, $M_5$, $L_1$, and $R_7$ are as defined above;

q. a process for preparing a thromboxane analog of the formula

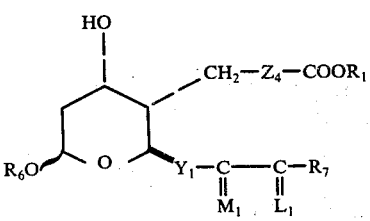

wherein $Z_4$ is (1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—, or
(6) —CH$_2$—O—CH$_2$—(CH$_2$)$_g$—CH$_2$—, wherein g is one, two, or 3;
wherein $R_6$ is hydrogen or alkyl of one to 4 carbon atoms, inclusive;
wherein $M_1$ is

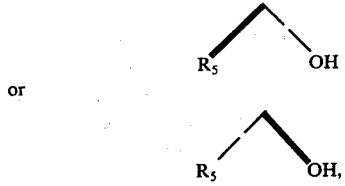

or wherein $R_5$ is hydrogen or methyl;
wherein $R_1$, $Y_1$, $L_1$, and $R_7$ are as defined above; which comprises:

optionally dealkylacetalating and separating any mixed epimers of a thromboxane analog of the formula

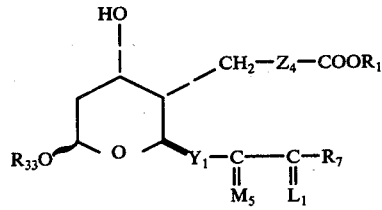

wherein $R_{33}$, $R_1$, $Z_4$, $Y_1$, $M_5$, $L_1$, and $R_7$ are as defined above.

r. a process for preparing a thromboxane analog of the formula

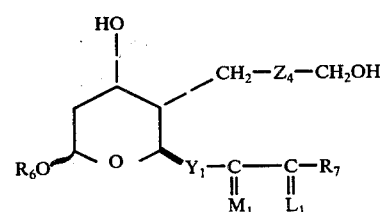

wherein $Z_1$, $R_6$, $Y_1$, $M_1$, $L_1$, and $R_7$ are as defined above; which comprises:

reducing to a primary alcohol and optionally dealkylacetalating a thromboxane analog of the formula

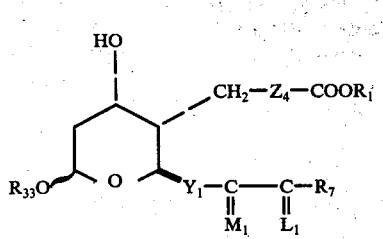
wherein $R_1$, $R_{33}$, $Y_1$, $M_1$, $L_1$, $Z_4$, and $R_7$ are as defined above.
In particular the present specification provides in conjunction with the above processes:
a thromboxane intermediate of the formula
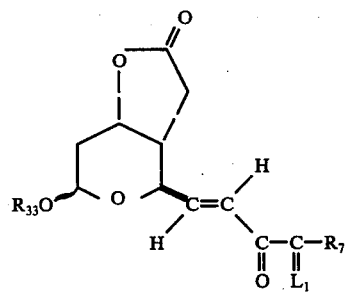
(a)
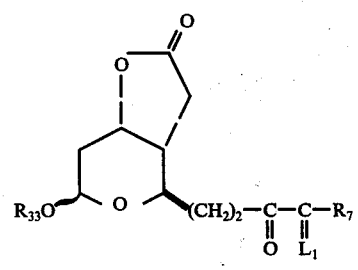
(b)
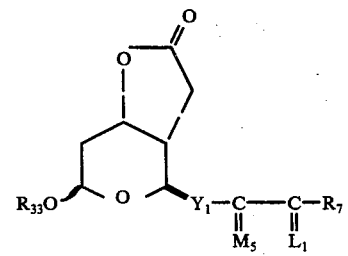
(c)
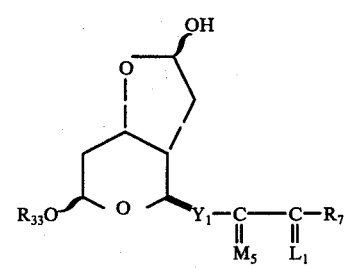
(d)
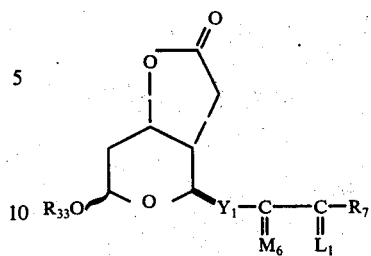
(e)
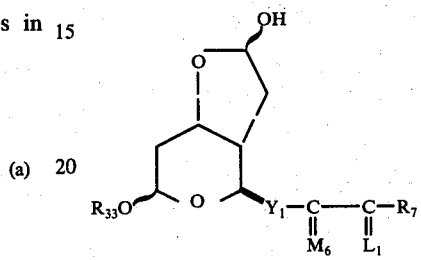
(f)
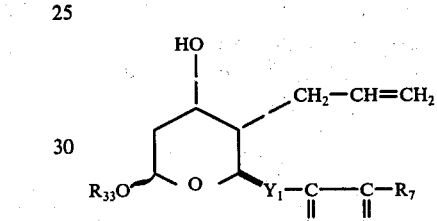
(g)
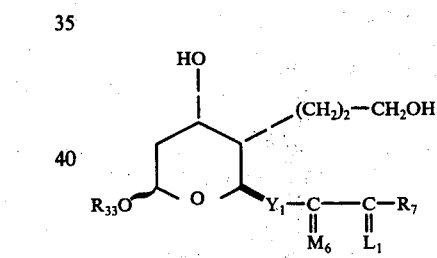
(h)
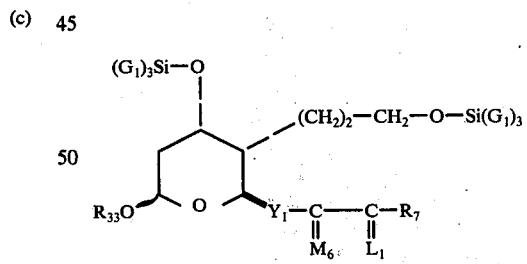
(i)
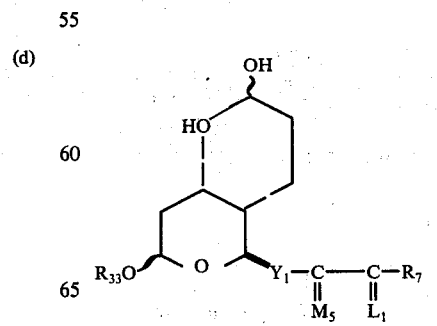
(j)

-continued

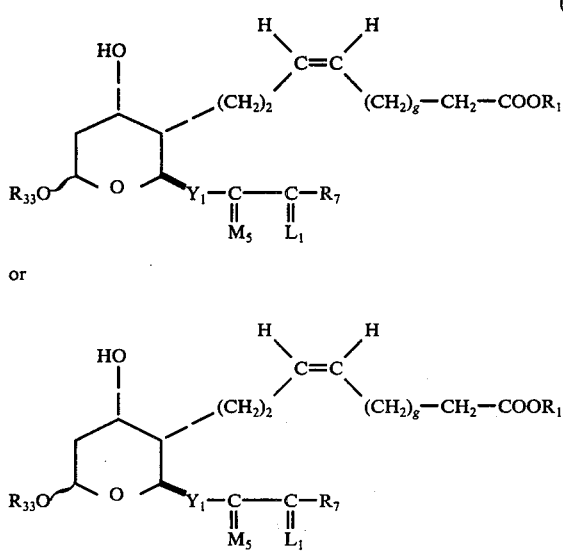

(k)

or (l)

wherein g, $R_{33}$, $L_1$, $R_7$, $M_5$, $M_6$, $Y_1$, and $G_1$ are as defined above.

Further the present specification discloses:

a. a process for preparing a thromboxane analog of the formula

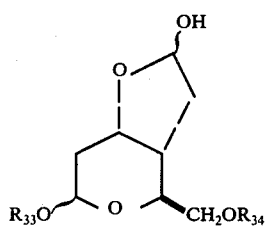

wherein $R_{33}$ is as defined above; and
wherein $R_{34}$ is an arylmethyl hydroxy-hydrogen replacing group;
which comprises:

1. reducing to a lactol a thromboxane intermediate of the formula

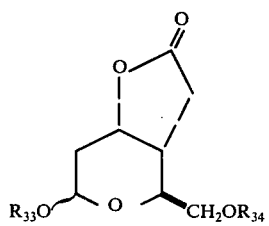

wherein $R_{33}$ and $R_{34}$ are as defined above;

b. a process as in part (a), which further comprises:

2. Wittig carboxylakylating and optionally esterifying the reaction product of step (1) of part (a), thereby preparing a thromboxane intermediate of the formula

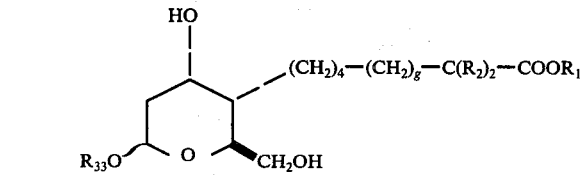

wherein $R_1$, $R_2$, g, $R_{33}$, and $R_{34}$ are as defined above;

c. a process as in part (b), which further comprises:

3. hydrogenating and hydrogenolyzing the reaction product of step (2) of part (b), thereby preparing a thromboxane intermediate of the formula wherein $R_1$, $R_2$, g, and $R_{33}$ are as defined above;

d. a process according to part (c), which further comprises:

4. oxidizing to an aldehyde the primary alcohol of the reaction product of step (3) of part (c), thereby preparing a thromboxane intermediate of the formula wherein $R_1$, $R_2$, g, and $R_{33}$ are as defined above;

e. a process as in part (d), which further comprises:

5. Wittig oxoalkylating and optionally hydrogenating the reaction product of step (4) of part (d);

6. transforming the oxo moiety of the reaction product of step (5) above to an $M_5$ moiety, wherein $M_5$ is or a mixture of and wherein $R_5$ is hydrogen or methyl;

7. optionally dealkylacetalizing the reaction product of step (6) above; and 8. separating any mixed tertiary alcohol epimers of the reaction product of step (7) above;
thereby preparing a thromboxane analog of the formula

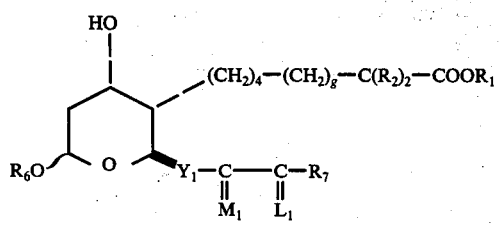

wherein $R_1$, $R_2$, g, $R_6$, $M_1$, $L_1$, and $R_7$ are as defined above.

In particular the specification provides in conjunction with the above processes:

a thromboxane analog of the formula

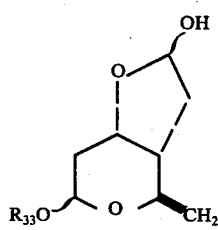

(a)

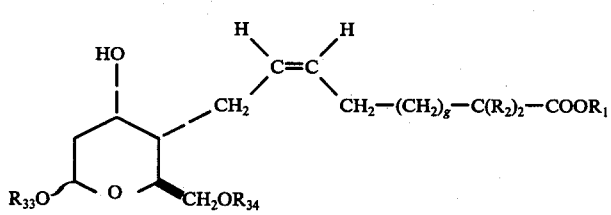

(b)

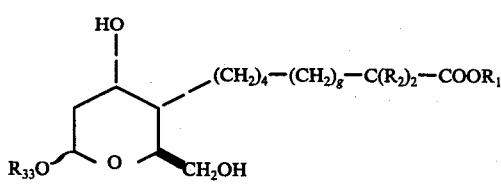

(c)

or

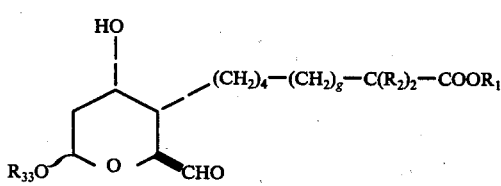

(d)

wherein $R_{33}$, $R_{34}$, $R_1$, $R_2$, and g are as defined above.

Further, the present specification discloses:

a. a process for preparing a thromboxane intermediate of the formula

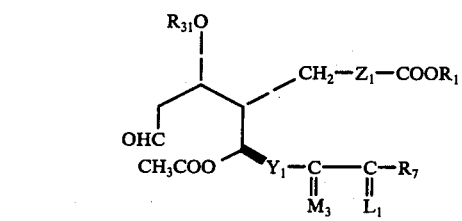

wherein $R_{31}$ is a hydroxy-hydrogen replacing group;
wherein $Z_1$ is 1. cis-CH=CH—$CH_2$—$(CH_2)_g$—$CH_2$—,
2. cis-Ch=CH—$CH_2$—$(CH_2)_g$—$CF_2$—,
3. cis—$CH_2$—OH=CH—$(CH_2)_g$—$CH_2$—,
4. —$(CH_2)_3(CH_2)_g$—$CH_2$—,
5. —$(CH_2)_3$—$(CH_2)_g$—$CF_2$—,
6. —$CH_2$—O—$CH_2$—$(CH_2)_g$—$CH_2$—,

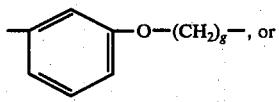  (7)

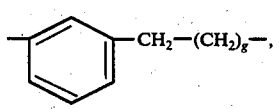  (8)

wherein g is as defined above;
wherein $M_3$ is

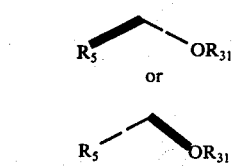

or wherein $R_5$ is hydrogen or methyl and $R_{31}$ is a hydroxy-hydrogen replacing group; and wherein $R_1$, $Y_1$, $L_1$, and $R_7$ are as defined above; which comprises:

1. oxidizing with lead tetraacetate a compound of the formula

[Structure: cyclopentane ring with $R_{31}O$, $CH_2-Z_1-COOR_1$, $HO$, and $Y_1-C(M_3)=C(L_1)-R_7$ substituents]

or a mixture comprising that compound and the enantiomer thereof;

wherein $R_{31}$, $Z_1$, $R_1$, $Y_1$, $M_3$, $L_1$, and $R_7$ are as defined above;

b. a process as in part (a) which further comprises:

2. dialkylacetalating the reaction product of step (1) of part (a), thereby preparing a thromboxane intermediate of the formula

[Structure: with $R_{31}O$, $CH_2-Z_1-COOR_1$, $(R_{33}O)_3HC$, $CH_3COO$, and $Y_1-C(M_3)=C(L_1)-R_7$]

wherein $R_{31}$, $R_{33}$, $Z_1$, $R_1$, $Y_1$, $M_3$, $L_1$, and $R_7$ are as defined above;

c. a process as in part (b) which further comprises:

3. replacing the hydroxy hydrogen replacing groups according to $R_{31}$ of the reaction product of step (2) of part (b) with hydrogen, thereby preparing a thromboxane intermediate of the formula

[Structure: with HO, $CH_2-Z_1-COOR_1$, $(R_{33}O)_3HC$, HO, and $Y_1-C(M_3)=C(L_1)-R_7$]

wherein $R_1$, $Z_1$, $Y_1$, $M_1$, $R_7$, and $R_{33}$ are as defined above;

d. a process for preparing a thromboxane intermediate of the formula

[Structure: bicyclic with O bridge, $CH_2-Z_1-C(=O)$, OHC, $CH_3COO$, and $Y_1-C(M_3)=C(L_1)-R_7$]

wherein $Z_1$, $Y_1$, $M_3$, $L_1$, and $R_7$ are as defined above; which comprises:

1. oxidizing with lead tetraacetate a compound of the formula

[Structure: cyclopentane with O bridge to $CH_2-Z_1-C(=O)$, HO, and $Y_1-C(M_3)=C(L_1)-R_7$]

or a mixture comprising that compound and the enantiomer thereof;

wherein $Z_1$, $Y_1$, $M_3$, $L_1$, and $R_7$ are as defined above.

e. a process as in part (d) which further comprises:

2. dialkylacetalating the reaction produce of step (1) of part (d), thereby preparing a thromboxane intermediate of the formula

[Structure: with O bridge, $CH_2-Z_1-C(=O)$, $(R_{33}O)_2HC$, $CH_3COO$, and $Y_1-C(M_3)=C(L_1)-R_7$]

wherein $Z_1$, $R_{33}$, $Y_1$, $M_3$, $L_1$, and $R_7$ are as defined above, f. a process as in part (e), which further comprises:

3. replacing hydroxy-hydrogen replacing groups according to $R_{31}$ with hydrogen, thereby preparing a thromboxane intermediate of the formula

[Structure: with HO, $CH_2-Z_1-COOH$, $(R_{33}O)_2HC$, HO, and $Y_1-C(M_1)=C(L_1)-R_7$]

wherein $Z_1$, $Y_1$, $M_1$, $L_1$, $R_7$, and $R_{33}$ are as defined above;

g. a process for preparing a thromboxane analog of the formula

[Structure: tetrahydropyran with HO, $CH_2-Z_1-COOR_1$, $R_{33}O$, O in ring, and $Y_1-C(M_1)=C(L_1)-R_7$]

wherein $R_1$, $Z_1$, $R_{33}$, $Y_1$, $M_1$, $L_1$, and $R_7$ are as defined above;

which comprises:

1. hydrolyzing a thromboxane intermediate of the formula

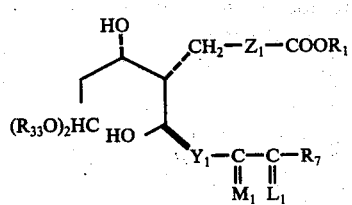

wherein $R_1$, $Z_1$, $R_{33}$, $Y_1$, $L_1$, and $R_7$ are as defined above;

h. a process as in part (g), which further comprises:

2. optionally dealkylacetalating the reaction product of step (1) of part (g), thereby preparing a thromboxane analog of the formula

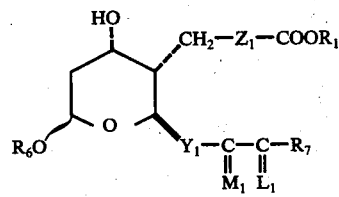

wherein $R_1$, $R_6$, $Z_1$, $Y_1$, $M_1$, $L_1$, and $R_7$ are as defined above;

i. a process as in part (h), which further comprises:

3. reducing to a primary alcohol the reaction product of step (2) of part (h), thereby preparing a thromboxane analog of the formula

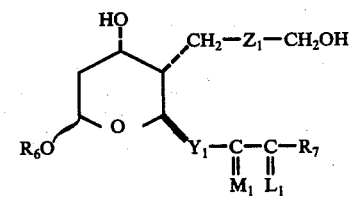

wherein $Z_1$, $Y_1$, $M_1$, $L_1$, $R_7$, and $R_6$ are as defined above.

In particulaar, the specification provides, in conjunction with the above process:

a thromboxane intermediate of the formula

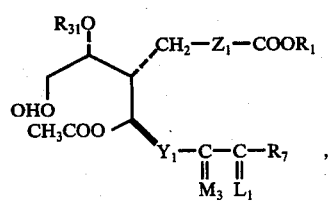  (a)

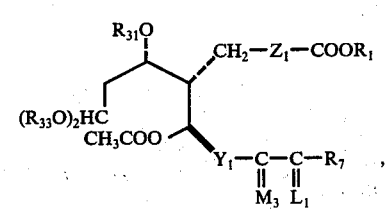  (b)

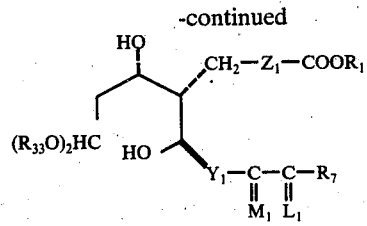  (c)

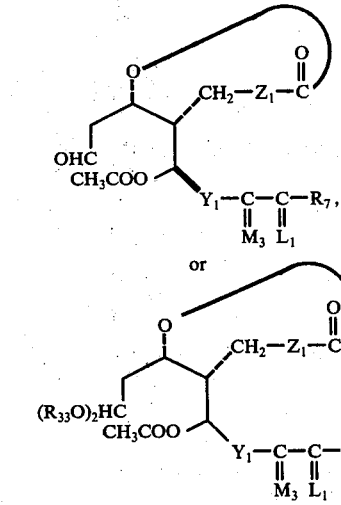

wherein $R_{31}$, $Z_1$, $R_1$, $Y_1$, $M_3$, $L_1$, $R_{33}$, $R_6$, and $R_7$ are as defined above.

Further the present specification discloses novel thromboxane analogs, as follows:

a. a thromboxane analog of the formula

wherein $R_6$, $Z_4$, $Y_1$, $M_1$, $L_1$, and $R_7$ are as defined above; and wherein $X_1$ is 1. —CH$_2$OH, or
2. —COOR$_1$, wherein $R_1$ is as defined above; with the overall proviso that $Z_1$ is cis—CH=CH—(CH$_2$)$_3$— $Y_1$ is trans—CH=CH—, $R_3$, $R_4$, and $R_5$ are all hydrogen, and $R_7$ is n-butyl, only when $X_1$ is —CH$_2$OH; and b. A thromboxane analog of the formula wherein $Z_5$ is

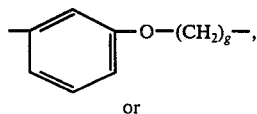

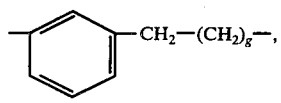

and wherein g, $X_1$, $R_6$, $Y_1$, $M_1$, $L_1$, and $R_7$ are as defined above.

Within the scope of the novel thromboxane analogs of this specification, thre are represented TXB-type compounds by virtue of the tetrahydropyran ring structure common to each of these thromboxane analogs:

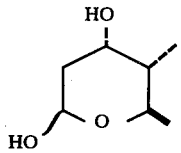

or 11-deoxy-11α- or 11β-alkoxy-TXB-type compounds (e.g., TXB-type, 11-alkyl acetals) by virtue of the tetrahydropyran ring structure common to each of these thromboxane analogs:

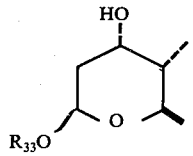

wherein $R_{33}$ is alkyl of one to 4 carbon atoms, inclusive.

Those analogs herein wherein $Z_4$ is cis—CH═CH—$CH_2$—$(CH_2)_g$— $CH_2$— or cis—CH═CH—($CH_2$—$(CH_2)_g$—$CF_2$— are named as "$TXB_2$" compounds. The latter compounds are further characterized as 2,2-difluoro-$TXB_2$-type compounds. When g is 2 or 3, the prostaglandin analogs so described are "2a-homo" or "2a,2b-dihomo" compounds, since in this event the carboxy terminated side chain contains 8 or 9 carbon atoms, respectively, in place of the 7 carbon atoms contained in $TXB_2$. These additional carbon atoms are considered as though they were inserted between the C-2 and C-3 positions. Accordingly, these additional carbon atoms are referred to as C-2a and C-2b, counting from the C-2 to the C-3 position.

Further when $Z_4$ is —$(CH_2)_3$—$(CH_2)_g$—$CH_2$— or —$(CH_2)_3$—$(CH_2)_g$—$CF_2$, wherein g is as defined above, the compounds so described are "$TXB_1$" compounds. When g is 2 or 3, the "2a-homo" and "2a,2b-dihomo" compounds are described as is discussed in the preceding paragraph.

When $Z_4$ is —$CH_2$—O—$CH_2$—$(CH_2)_g$—$CH_2$— the compounds so described are named as "5-oxa-$TXB_1$" compounds. When g is 2 or 3, the compounds so described are "2a-homo" or "2a,2b-dihomo" compounds, respectively, as discussed above.

When $Z_4$ is cis—$CH_2$—CH═CH—$(CH_2)_g$—$CH_2$—, wherein g is as defined above, the compounds so described are named "cis-4,5-didehydro-$TXB_1$" compounds. When g is 2 or 3, the compounds so described are further characterized as "2a-homo" or "2a,2b-dihomo" compounds, respectively, as discussed above.

For the novel compounds of this invention wherein $Z_5$ is

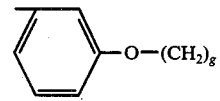

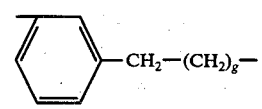

there are described, respectively, 3-oxa-3,7-inter-m-phenylene-4,5,6-trinor- or 3,7-inter-m-phenylene-4,5,6-trinor-$TXB_1$-type compounds, when g is 1. When g is 2 or 3, the above compounds are additionally described as "2a-homo" or "2a,2b-dihomo" TXB-type compounds, respectively.

The novel thromboxane analogs of this invention wherein $Y_1$ is —$CH_2CH_2$— are referred to as "13,14-dihydro" compounds.

When $R_7$ is —$(CH_2)_m$—$CH_3$, wherein m is as defined above, the compounds so described are named as "19,20-dinor", "20-nor", "20-methyl", or "20-ethyl" compounds when m is one, 2, 4, or 5, respectively.

When $R_7$ is

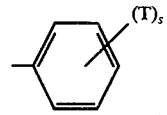

wherein T and s are as defined above, the compounds so described are named as "16-phenyl-17,18,19,20-tetranor" compounds, when s is 0. When s is one, 2, or 3, the corresponding compounds are named as "16-(substituted phenyl)-17,18,19,20-tetranor" compounds.

When $R_7$ is

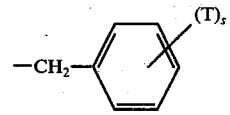

wherein T and s are as defined above, tne compounds so described are named as "17-phenyl-18,19,20-trinor" compounds, when s is 0. When s is one, 2, or 3, the corresponding compounds are named as "17-(substituted phenyl)18,19,20-trinor" compounds.

When $R_7$ is

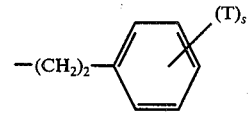

wherein T and s are as defined above, the compounds so described are named as "18,-phenyl-19,20-dinor" compounds, when s is 0. When s is one, 2, or 3, the corresponding compounds are named as "18-(substituted phenyl)-19,20-dinor" compounds.

When $R_7$ is

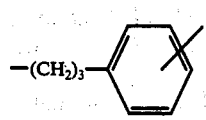

wherein T and s are as defined above, the compounds so described are named as "19-phenyl-20-nor" compounds, when s is 0. When s is one, 2, or 3, the corresponding compounds are named as "19-(substituted phenyl)-20-nor" compounds.

When $R_7$ is

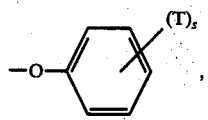

wherein T and s are as defined above, and neither $R_3$ nor $R_4$ is methyl, the compounds so described are named as "16-phenoxy-17,18,19,20-tetranor" compounds, when s is zero. When s is one, 2, or 3, the corresponding compounds are named as "16-(substituted phenoxy)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenoxy or 16-substituted phenoxy)-18,19,20-trinor" compounds or "16-methyl-16-phenoxy- or 16-(substituted phenoxy)-18,19,20-trinor" compounds, respectively.

When at least one of $R_3$ and $R_4$ is not hydrogen then (except for the 16-phenoxy compounds discussed above) there are described the "16-methyl" (one and only one of $R_3$ and $R_4$ is methyl), "16,16-dimethyl" ($R_3$ and $R_4$ are both methyl), "16-fluoro" (one and only one of $R_3$ and $R_4$ is fluoro), "16,16-difluoro" ($R_3$ and $R_4$ are both fluoro) compounds. For those compounds wherein $R_3$ and $R_4$ are different, the thromboxane analogs so represented contain an asymmetric carbon atom at C-16. Accordingly, two epimeric configurations are possible: "(16S)" and "(16R)". Further, there is described by this invention the C-16 epimeric mixture: "(16RS)".

When $R_5$ is methyl, the compounds so described are named as "15-methyl" compounds. When $R_6$ is alkyl, the compounds so described are named as TXB-type, 11α- or 11β-alkyl acetals or preferably, as described above, as "11-deoxy-11α- or 11β-alkoxy-TXB" compounds.

There is further provided by this invention both epimeric configurations of the hydroxy at C-15. As discussed herein, $TXB_2$, as obtained biosynthetically has the "S" configuration at C-15. Further, as drawn herein $TXB_2$, as obtained biosynthetically, has the 15-hydroxy moiety in the "alpha" configuration. Further, 15-epi-$TXB_2$, by the convention used for drawing the thromboxane analogs herein, has the 15-hydroxy substitutent in the beta configuration. Thus, the novel thromboxane analogs disclosed herein wherein the 15-hydroxy has the same absolute configuration as 15-epi-$TXB_2$ at C-15 will be named "15-epi" compounds. When the designation "15-epi" is absent, those compounds wherein the configuration of the 15-hydroxy is the same as the absolute configuration of $TXB_2$, i.e. the 15α-hydroxy configuration.

When $X_1$ is —$CH_2OH$ the thromboxane analogs so described are named as "2-decarboxy-2-hydroxymethyl" compounds.

Accordingly, as indicated by the preceeding paragraphs, the novel PG analogs disclosed herein are named according to the system described in Nelson, N.A., J. Med. Chem. 17, 911 (1974).

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2.3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one of 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

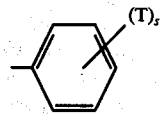

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)-ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)-chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3- 2,4-, 2,5-, 2,6-, 3,4-, or 3,5-)dichlorophenyl, 4-chloro-3-fluorophenyl, (3- or 4-) chloro-2-fluorophenyl, o-, m-, or p-trifluoromethylphenyl, (o-, m-, or p-)methoxyphenyl, (o-, m-, or p-)ethoxyphenyl, (4- or 5-)chloro-2-methoxyphenyl, and 2,4-dichloro(5- or 6-)methylphenyl.

The novel thromboxane analogs disclosed herein correspond to the TXB compounds described above, in that the novel thromboxane analogs exhibit $TXB_2$-like activity.

Specifically the TXB analogs disclosed herein correspond to the $TXB_2$ described above, in that these TXB analogs are useful for the above-described purposes for which the $TXB_2$ is used, and are used in the same manner as $TXB_2$, as described above. $TXB_2$ is potent in causing biological responses even at low doses. Moreover, for the above applications, $TXB_2$ exhibits an inconveniently short duration of biological activity. In striking contrast, the novel thromboxane analogs of this invention are substantially more selective with regard to potency in causing $TXB_2$-like biological responses, and have a substantially longer duration of biological activity. Accordingly, each of these novel thromboxane analogs is surprisingly and unexpectedly more useful than $TXB_2$ for at least one of the pharmacological purposes indicated above for the latter, because it has a different and narrower spectrum of biological potency than $TXB_2$ and therefore is more specific in its activity and causes smaller and fewer undesired side effects than when $TXB_2$ is used for the same purpose. Moreover, because of its prolonged activity, fewer and smaller doses of the novel thromboxane analog are frequently effective in attaining the desired result.

Another feature of the novel thromboxane analogs disclosed herein, especially the preferred TXB analogs defined hereinbelow is that these novel TXB analogs logs are administered effectively orally, sublingually, intravaginally, buccally, or rectally. These routes of administration are advantageous because they facilitate maintaining uniform levels of these compounds in the body with fewer, shorter, or smaller doses, and make possible self-administration by the patient.

Accordingly, the novel thromboxane analogs of this invention are administered in various ways for various purposes: e.g., intravenously, intramuscularly, subcutaneously, orally, intravaginally, rectally, buccally, sublingually, topically, and in the form of sterile implants for prolonged action. For intraveneous injection of infusion, sterile aqueous isotonic solutions are preferred. For intravenous injection or infusion, sterile aqueous isotonic solutions are preferred. For that purpose it is preferred because of increased water solubility that when $X_1$ is —$COOR_1$, $R_1$ be hydrogen or a pharmacologically acceptable cation. For subcutaneous or intramuscular injection, sterile solutions or suspensions of the acid, salt, or ester form in aqueous or non-aqueous media are used. Tablets, capsules. and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The novel TXB analogs of this invention are used for the purposes described above as primary alcohols or in the free acid form ($X_1$ is —COOH), in ester form or in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araaliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts are the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

To obtain the optimum combination of biological response specificity, potency, and duration of activity, certain compounds within the scope of this invention are preferred.

It is preferred that g be one or 3, and especially preferred that g be one, i.e., the natural chain length of $TXB_2$. Further when the other side chain contains —$(CH_2)_m$—$CH_3$, it is preferred that m be 3. For those compounds wherein $R_7$ is

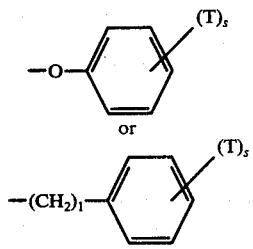

it is preferred that s and l be zero or one and T be chloro, fluoro, or trifluoromethyl.

For those compounds wherein at least one of $R_3$ and $R_4$ is methyl or fluoro, it is preferred that $R_5$ be hydrogen. For those compounds wherein $R_5$ is methyl, it is preferred that $R_3$ and $R_4$ both be hydrogen. For those compounds wherein $R_7$ is

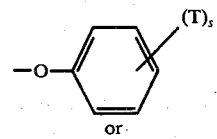

-continued

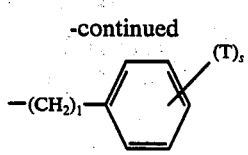

it is preferred that $R_3$, $R_4$, $R_5$, and $R_6$ all be hydrogen.

It is further preferred that the 15-hydroxy not be of the 15-epi configuration, i.e., that the hydroxy be in the alpha configuration when the formulas are as drawn herein.

Especially preferred are those compounds which satisfy two or more of the above preferences. Further, the above preferences are expressly intended to describe the preferred compounds within the scope of any generic formula of novel thromboxane analogs disclosed herein.

In another aspect of the interpretation of the preferences herein, the various thromboxane tetrahydropyran ring structures (e.g. hemiacetal and 11α- or 11β-alkyl acetals) as employed herein are each representative of a particular "parent structure" which is useful in naming and categorizing the novel thromboxane analogs disclosed herein. Further, where a formula depicts a genus of TXB analogs disclosed herein evidencing a single tetrahydropyran ring structure, then each corresponding genus of TXB analogs evidencing one of the remaining tetrahydropyran ring structures cited herein for novel thromboxane analogs is intended to represent an equally preferred genus of compounds. Thus, for example, for each genus of TXB-type products depicted by a formula herein, the corresponding genus of 11-deoxy-11α-methoxy-$TXB_2$-type products are equally preferred embodiments of present disclosure as the genus of TXB-type products.

Finally where subgeneric group of TXB analogs of any tetrahydropyran ring structure are described herein, then the corresponding subgeneric groups of TXB analogs of any other tetrahydropyran ring structure is intended to represent equally preferred embodiments of the present invention.

The Charts herein described methods whereby the novel thromboxane analogs of this invention are prepared.

With respect to the charts $R_1$, $R_2$, $R_6$, $R_{10}$, $R_7$, $R_{31}$, $R_{33}$, $R_{34}$, $M_1$, $M_3$, $M_5$, $M_6$, $L_1$, $Y_1$, $X_1$, $Z_4$, $Z_5$, $G_1$, $m$, and $g$ are as defined above.

Chart A (Part I)

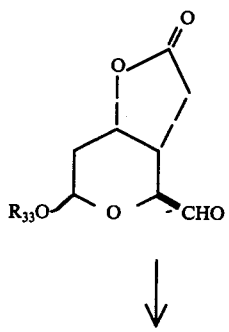

XI

-continued
Chart A (Part I)

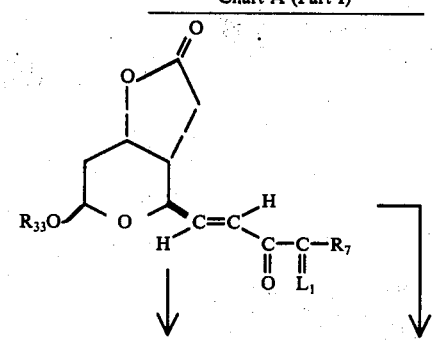

XII

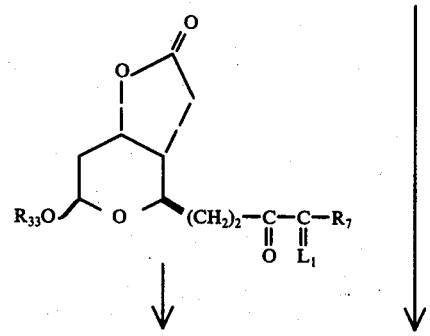

XIII

XIV

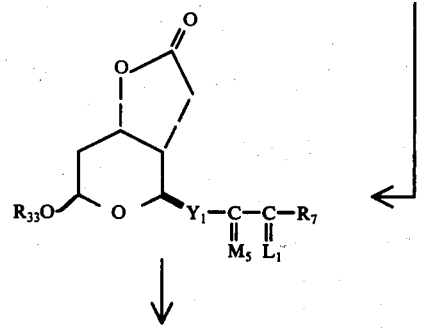

XV

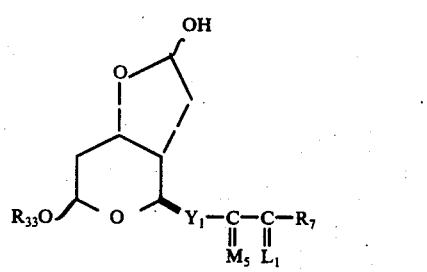

Chart A (Part II)

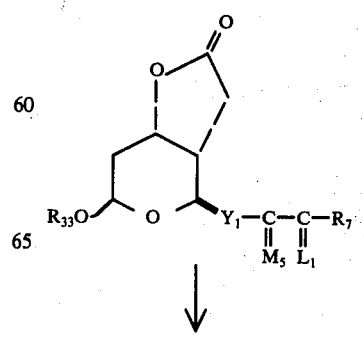

XVI

-continued
Chart A (Part II)
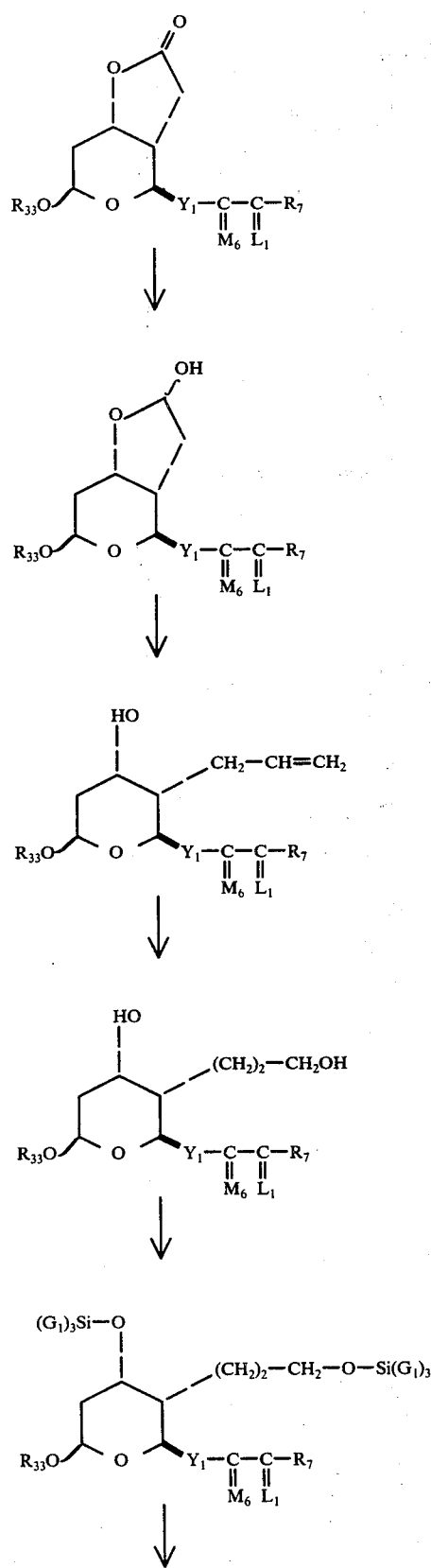
-continued
Chart A (Part II)
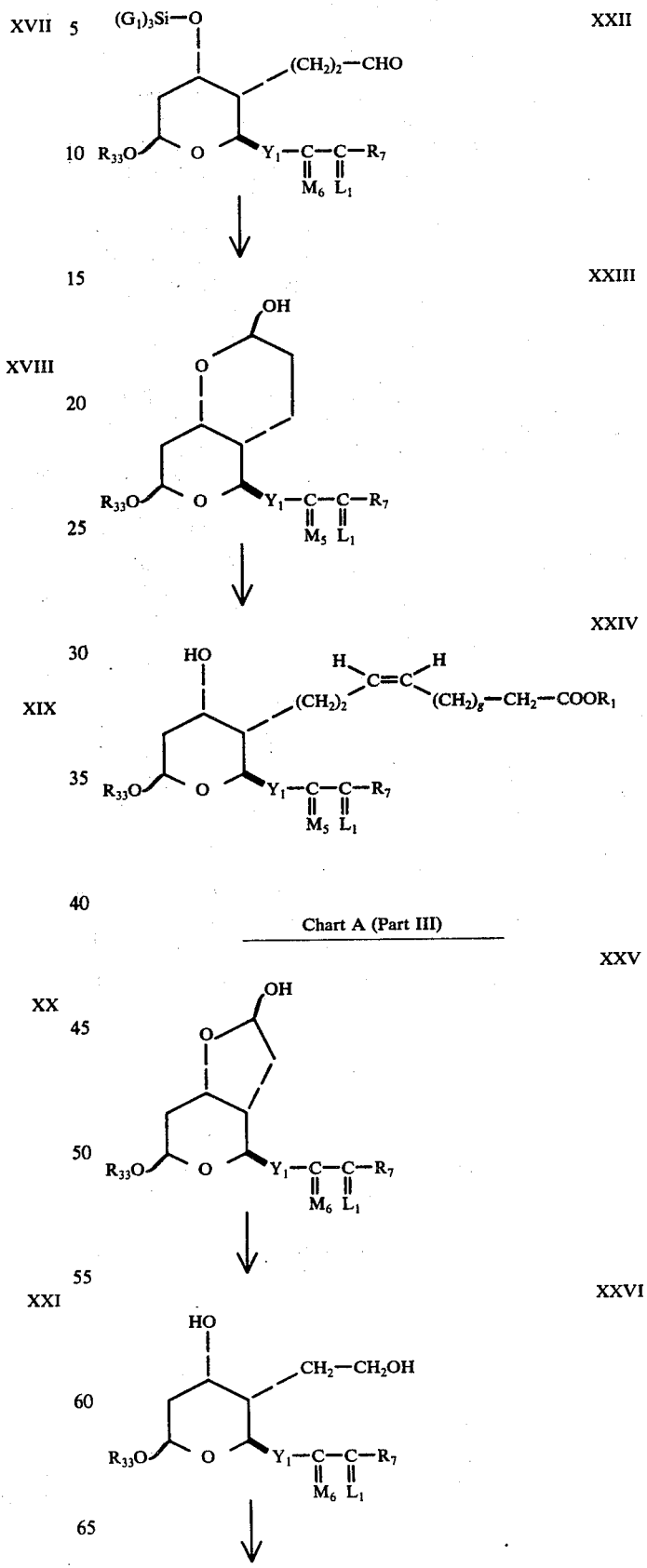
Chart A (Part III)
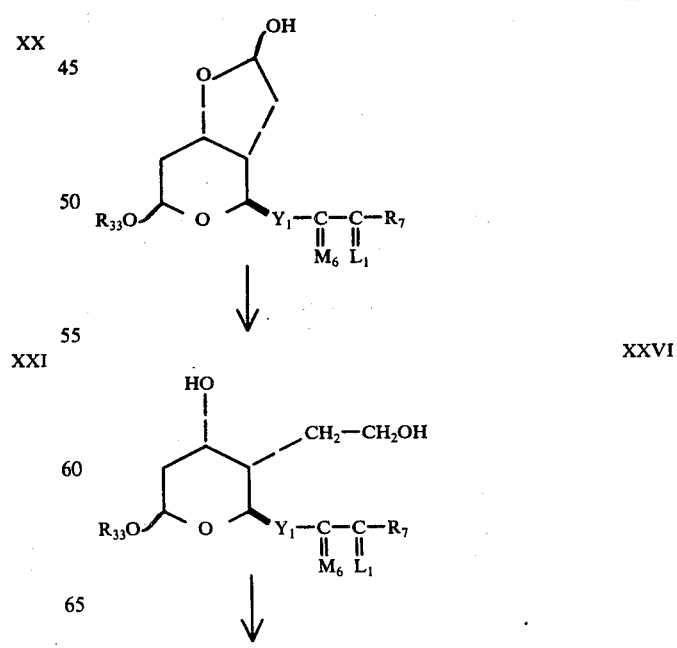

Chart A (Part III)
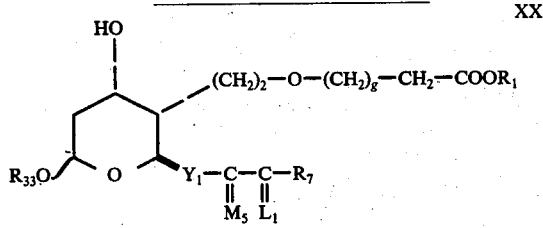
XXVII
Chart A (Part IV)
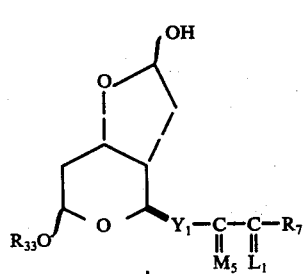
XXVIII
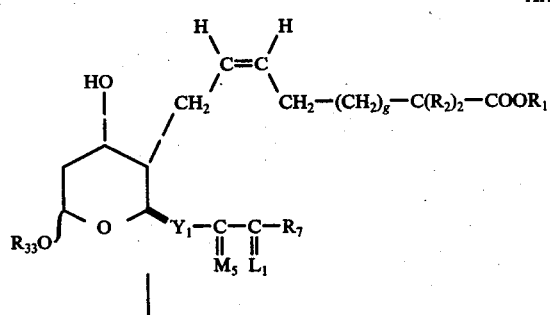
XXIX
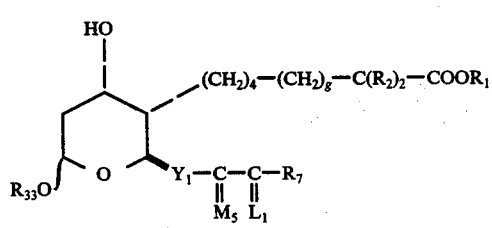
XXX
Chart A (part V)
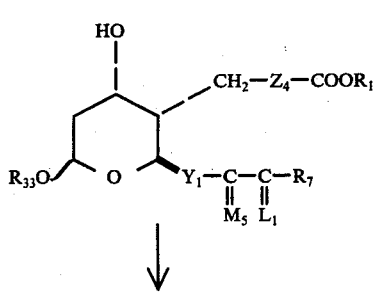
XXXI
Chart A (part V)
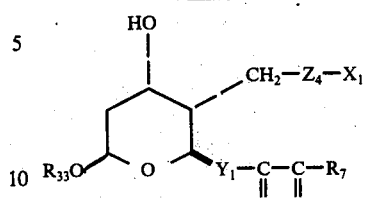
XXXII
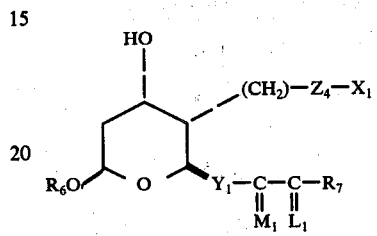
XXXIII
Chart A (Part VI)
XXXIV
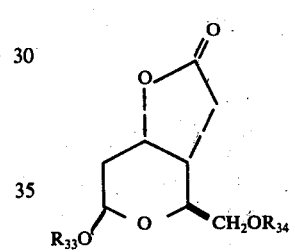
XXXV
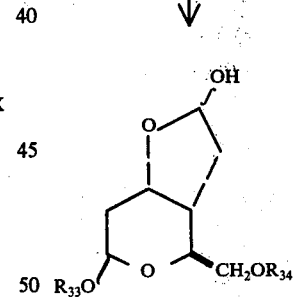
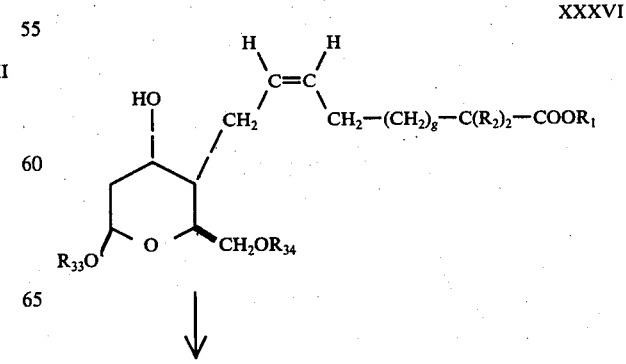
XXXVI 4,054,737
-continued
Chart A (Part VI)
XXXVII
XXXVIII
XXXIX
Chart B
XL
XLI
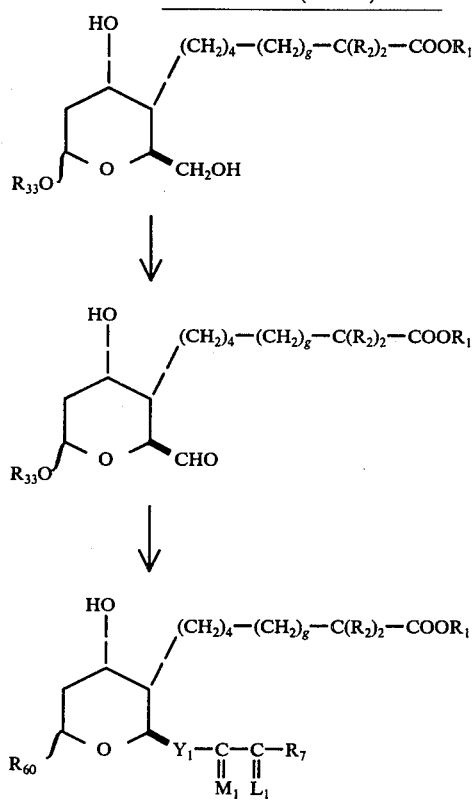
-continued
Chart B
XLIII
XLVIII
XLIX
L
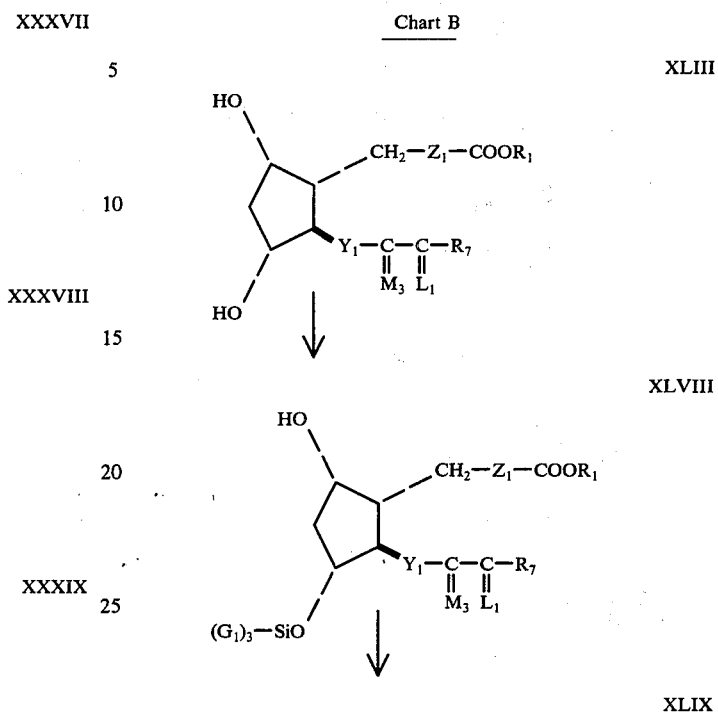
Chart C
LI
XLII
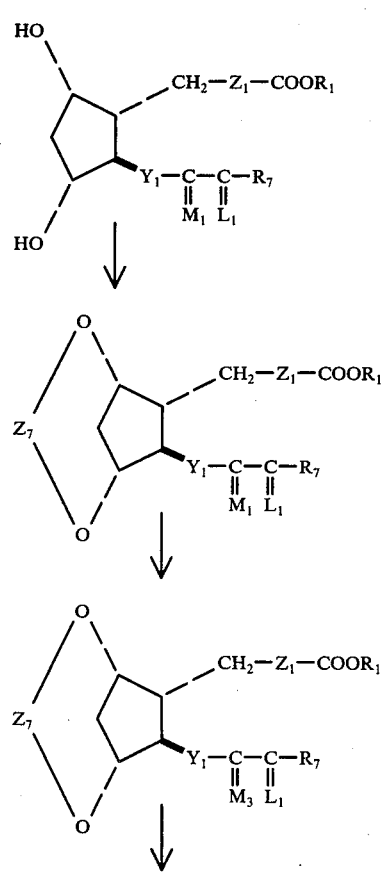
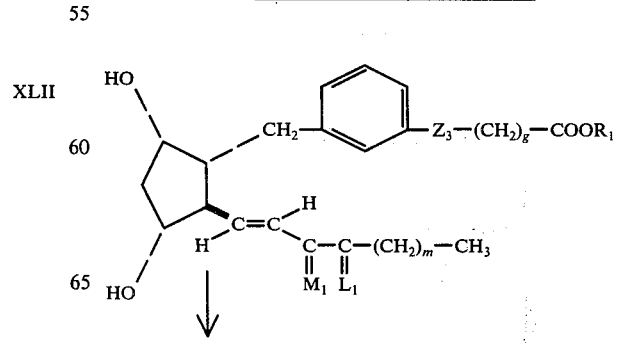

-continued
Chart C
LII 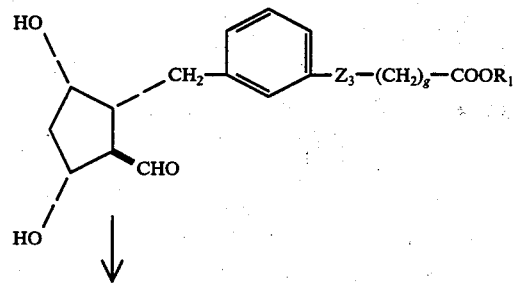
↓
LIII 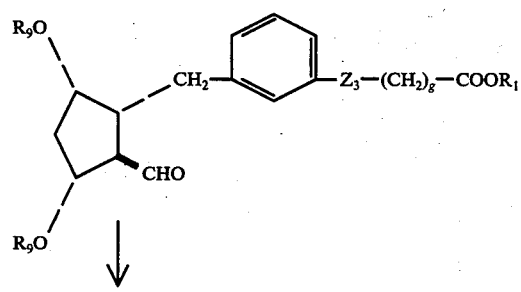
↓
LIV 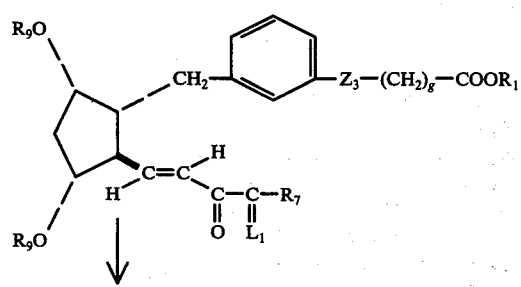
↓
LV 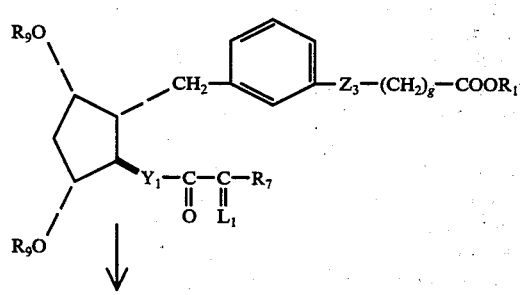
↓
LVI 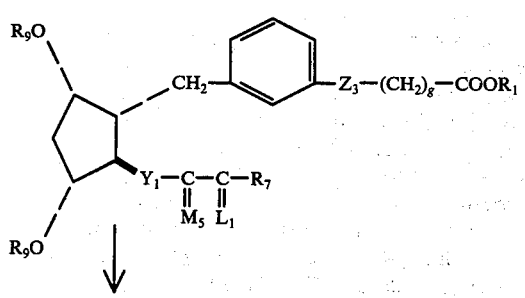
↓
-continued
Chart C
LVII 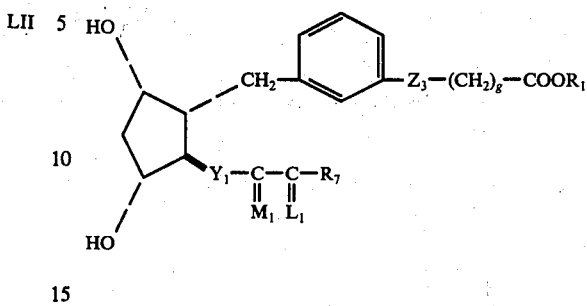
Chart D (Part I)
LXI 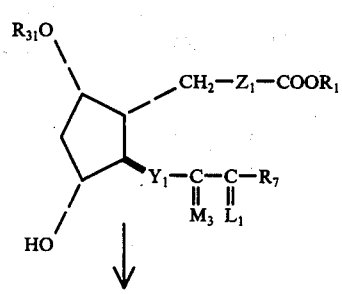
↓
LXII 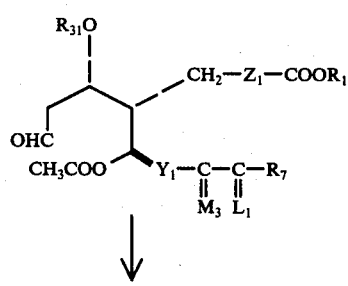
↓
LXIII 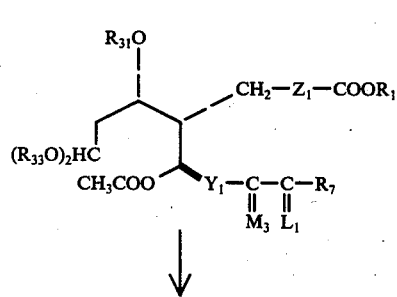
↓
LXIV 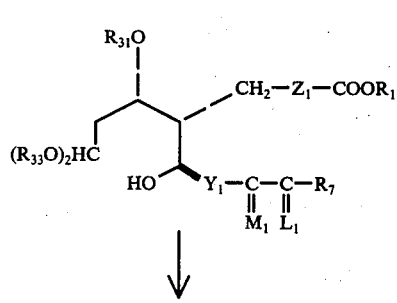
↓

Chart D (Part I)

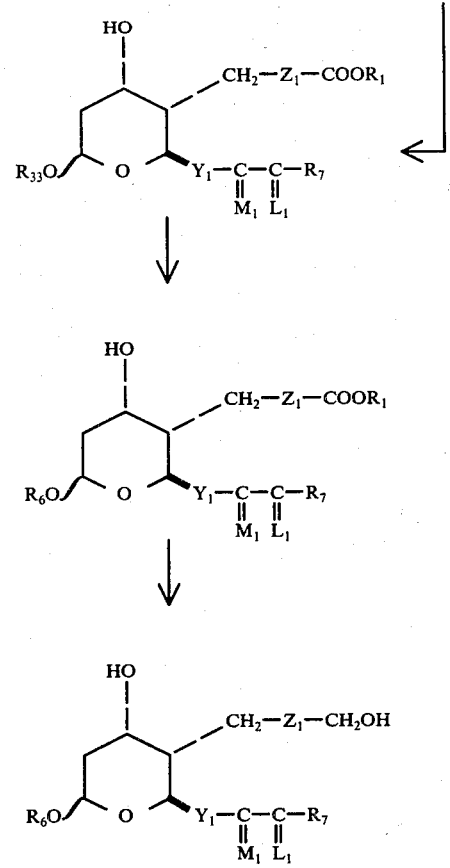

Chart D (Part II)

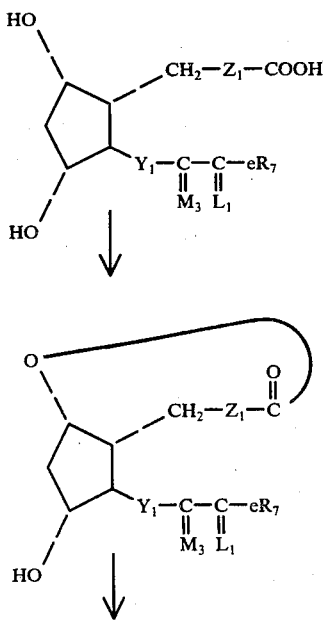

Chart D (Part II) -continued

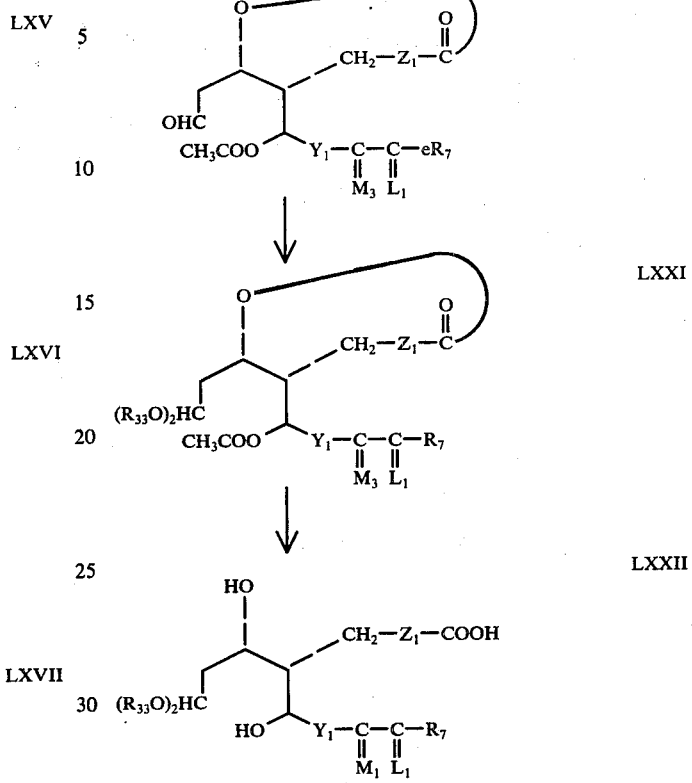

$R_9$ is an acyl protecting group.

$Z_1$ is $Z_4$ or $Z_5$, $Z_3$ is oxa or methyl. $Z_7$ is $R_{36}$-B wherein $R_{36}$ is alkyl or aryl, preferably such that the corresponding boranic acid is readily available, e.g., (n-butyl)-boronic acid or phenylboronic acid.

$R_9$ is an acyl protecting group. Acyl protecting groups according to $R_9$, include:

a. benzoyl;

b. benzoyl substituted with one to 5 alkyl of one to 4 carbon atoms, inclusive, phenylalkyl of 7 to 12 carbon atoms, inclusive, or nitro, with the proviso that not more than 2 substituents are other than alkyl, and that the total number of carbon atoms in the substituents does not exceed 10 carbon atoms, with the further proviso that the substituents are the same or different;

c. benzoyl substituted with alkoxycarbonyl of 2 to 5 carbon atoms, inclusive;

d. naphthoyl;

e. naphthoyl substituted with one to 9, inclusive alkyl of one to 4 carbon atoms, inclusive, phenylalkyl of 7 to 10 carbon atoms, inclusive, or nitro, with the proviso that not more than 2 substituents on either of the fused aromatic rings are other than alkyl and that the total number of carbon atoms in the substituents on either of the fused armoatic rings does not exceed 10 carbon atoms, with the further proviso that the various substituents are the same or different; or f. alkanoyl of 2 to 12 carbon atoms, inclusive.

In preparing these acyl derivatives of a hydroxy-containing compound herein, methods generally known in the art are employed. Thus, for example, an aromatic acid of the formula $R_9OH$, wherein $R_9$ is as defined above (e.g., benzoic acid), is reacted with the hydroxy-containing compound in the presence of a dehydrating agent, e.g. p-toluenesulfonyl chloride or dicyclohexylcarbodiimide; or alternatively an anhydride of the aromatic acid of the formula $(R_9)_2O$ (e.g., benzoic anhydride) is used.

Preferably, however, the process described in the above paragraph proceeds by use of the appropriate acyl halide, e.g., $R_9$Hal, wherein Hal is chloro, bromo, or iodo. For example, benzoyl chloride is reacted with the hydroxyl-containing compound in the presence of a hydrogen chloride scavenger, e.g. a tertiary amine such as pyridine, triethylamine or the like. The reaction is carried out under a variety of conditions, using procedures generally known in the art. Generally mild conditions are employed: 0°–60° C., contacting the reactants in a liquid medium (e.g., excess pyridine or an inert solvent such as benzene, toluene, or chloroform). The acylating agent is used either in stoichiometric amount or in substantial stoichiometric excess.

As examples of $R_9$, the following compounds are available as acids ($R_9$OH), anhydrides (($R_9$)$_2$O), or acyl chlorides ($R_3$Cl): benzoyl; substituted benzoyl, e.g., 2-, 3-, or 4-)-methylbenzoyl, (2-, 3-, or 4-)-ethyl benzoyl, (2-, 3-, or 4-)-isopropylbenzoyl (2-, 3-, or 4-)-tert-butylbenzoyl, 2,4-dimethylbenzoyl, 3,5-dimethylbenzoyl, 2-isopropyltoluyl, 2,4,6-trimethylbenzoyl, pentamethylbenzoyl, alphaphenyl-(2-, 3-, or 4-)-toluyl, (2-, 3-, or 4-)-phenethylbenzoyl, (2-, 3-, or 4-)-nitrobenzoyl, (2,4-, 2,5-, or 2,3-)-dinitrobenzoyl, 2,3-dimethyl-2-nitrobenzoyl, 4,5-dimethyl-2-nitrobenzoyl, 2-nitro-6-phenethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl, substituted naphthoyl, e.g., (2-, 3-, 4-, 5-, 6-, or 7-)-methyl-1-naphthoyl, (2- or 4-) ethyl-1-naphthoyl, 2-isopropyl-1-naphthoyl, 4,5-dimethyl-1-naphthoyl, 6-isopropyl-4-methyl-1-naphthoyl, 8benzyl-1-naphthoyl, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9$Cl compounds corresponding to the above $R_9$ groups. If the acyl chloride is not available, it is prepared from the corresponding acid and phosphorus pentachloride as is known in the art. It is preferred that the $R_9$OH, ($R_9$)$_2$O, or $R_9$Cl reactant does not have bulky hindering substituents, e.g. tert-butyl on both of the ring carbon atoms adjacent to the carbonyl attaching site.

The acyl protecting groups, according to $R_9$, are removed by deacylation, Alkali metal carbonate or hydroxide are employed effectively at ambient temperature for this purpose. For example, potassium carbonate or hydroxide in aqueous methanol at about 25° C. is advantageously employed.

Those blocking groups within the scope of $R_{10}$ are any group which replaces a hydroxy hydrogen and is neither attacked by nor as reactive to the reagents used in the transformations used herein as an hydroxy is and which is subsequently replaceable with hydrogen in the preparation of the prostaglandin-type compounds. Several blocking groups are known in the art, e.g. tetrahydropyranyl and substituted tetrahydropyranyl. See for reference E. J. Corey, Proccedings of the Robert A Welch Foundation Conferences on Chemical Research, 12, Organic Synthesis, pgs. 51–79 (1969). Those blocking groups which have been found useful include:

a. tetrahydropyranyl;
b. tetrahydrofuranyl; and
c. a group of the formula

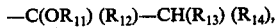

$-C(OR_{11})(R_{12})-CH(R_{13})(R_{14})$, wherein $R_{11}$ is alkyl of one to 18 carbon atoms inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together $-(CH_2)_a-$ or $-(CH_2)_b-O-(CH_2)_c$, wherein a is 3, 4, or 5, or b is one, 2, or 3, and c is one, 2, or 3, with the proviso that b plus c is 2, 3, or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the TXB-type intermediates herein is obtained by reaction of the hydroxy-containing compound with 2,3-dihydropyran in an inert solvent, e.g. dichloromethane, in the presence of an acid condensing agent such as p-toluenesulfonic acid of pyridine hydrochloride. The dihydropyran is used in large stoichiometric excess, preferably 4 to 100 times the stoichiometric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula

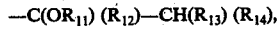

$-C(OR_{11})(R_{12})-CH(R_{13})(R_{14})$, wherein $R_{11}$, $R_{12}$, $R_{13}$, and $R_{14}$ are as defined above, the appropriate reagent is a vinyl ether, e.g. isobutyl vinyl ether or any vinyl ether of the formula

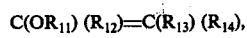

$C(OR_{11})(R_{12})=C(R_{13})(R_{14})$, wherein $R_{11}$, $R_{12}$, $R_{13}$, and $R_{14}$ are as defined above; or an unsaturated cyclic or heterocyclic compound, e.g. 1-cyclohexen-1-yl methyl ether, or 5,6-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above.

The blocking groups according to $R_{10}$ are removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking groups is achieved.

$R_{34}$ is an arylmethyl hydroxy-hydrogen replacing group, which is defined as any arylmethyl group which replaces the hydroxy hydrogen of the intermediates in the preparation of the various thromboxane analogs herein which is subsequently replaceable by hydrogen in the processes herein for preparation of these respective thromboxane analogs, being stable with respect to the various reactions to which $R_{34}$-containing compounds are subjected and being introduced and subsequently removed by hydrogenolysis under conditions which yield substantially quantitative yields of desired products.

Examples of arylmethyl hydroxy-hydrogen replacing groups are a. benzyl (i.e.,

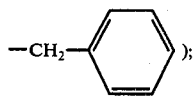

b. benzyl substituted by one to 5 alkyl of one to 4 carbon atoms, inclusive, chloro, bromo, iodo, fluoro, nitro, phenylalkyl of 7 to 12 carbon atoms, inclusive, with the further proviso that the various substituents are the same or different;

c. benzhydryl (i.e.,

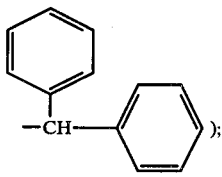

d. benzhydryl substituted by one to 10 alkyl of one to 4 carbon atoms, inclusive, chloro, bromo, iodo, fluoro, nitro, phenylalkyl of 7 to 12 carbon atoms, inclusive, with the further proviso that the various substituents are the same or different on each of the aromatic rings;

e. trityl (i.e.,

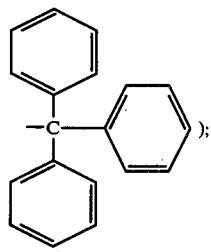

f. trityl substituted by one to 15 alkyl of one to 4 carbon atoms, inclusive, chloro, bromo, iodo, fluoro, nitro, phenylalkyl of 7 to 12 carbon atoms, inclusive, with the further proviso that the various substituents are the same or different on each of the aromatic rings.

The introduction of such ether linkages to the hydroxy-containing compounds herein, particularly the benzyl or substituted benzyl ether proceeds by methods known in the art, for example by reaction of the hydroxy-containing compound with the benzyl or substituted benzyl halide (chloride, bromide, or iodide) corresponding to the desired ether. This reaction proceeds in the presence of an appropriate condensing agent (e.g., silver oxide). The mixture is stirred and heated to 50°-80° C. Reaction times of four to 20 hours are ordinarily sufficient.

These arylmethyl grops are subsequently removed by hydrogenolysis, for example by catalytic hydrogenation over a 5-10 percent palldium-on-carbon catalyst.

$R_{31}$ is a hydroxy-hydrogen replacing group which is stable to the reagents employed herein in the preparation of $TXB_2$, and subsequently, readily hydrolyzed or hydrogenolysed as required herein. Those hydroxy-hydrogen replacing groups useful for this purpose include ay acyl protecting group according to $R_9$, blocking group according to $R_{10}$, or arylmetyl hydroxy-hydrogen replacing group according to $R_{34}$.

Various reactions in the succeeding charts introduce silyl groups of the formula $—Si(G_1)_3$. In some cases, such silylations are general, in that they silylate all hydroxyls, while in other cases they are selective, in that while one or more hydroxyls are silylated, at least one other hydroxyl remains unaffected. For any of these silylations, silyl groups within the scope of $—Si(G_1)_3$ include trimethylsilyl, dimethylphenylsilyl, triphenylsilyl, t-butyldimethylsilyl, or methylphenylbenzylsilyl. With regard to $G_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenylpropyl, α-naphthylmethyl, and 2-(β-naphthyl)-ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

These silyl groups are known in the art. See for example, Pierce "Silylation of Organic Compounds," Pierce Chemical Company, Rockford, Ill. (1968). When silylated products of the charts below are intended to be subjected to chromatographic purification, then the use of silyl groups known to be unstable to chromatography (e.g. trimethylsilyl) should be avoided. Further, when silyl groups are to be introduced selectively, silylating agents which are readily available and known to be useful in selective silylations are employed. For example, trimethylsilyl, triphenylsilyl and t-butyldimethylsilyl groups are employed when selective introduction is required. Further, when silyl groups are to be selectively hydrolyzed over protecting groups according to $R_{10}$ or acyl protecting groups, then the use of silyl groups which are readily available and known to be easily hydrolyzable with tetra-n-butylammonium fluoride are employed. A particularly useful silyl group for this purpose is t-butyldimethylsilyl, although other silyl groups (e.g. trimethylsilyl) are likewise employed.

With respect to Chart A (Part I) the formula XI compound is prepared as described in U.S. Pat. No. 4,020,173. This compound is available in either of two enantiomeric forms or as a mixture thereof.

The formula XII compound is prepared from the formula XI compound by a Wittig alkylation. Reagents known in the art of prepared by methods known in the art are employed. The transenone lactone is obtained stereospecifically. See for reference D. H. Wadsworth, et al., Journal of Organic Chemistry 30, 680 (1965).

In the preparation of the formula XII compound, certain phosphonates are employed in the Wittig reaction. These phosphonates are of the general formula

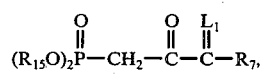

wherein $L_1$ and $R_7$ are as defined above and $R_{15}$ is alkyl of one to 8 carbon atoms, inclusive.

Phosphonates of the above general formula are prepared by methods known in the art. See Wadsworth, et al. as cited above.

Conveniently the appropriate aliphatic acid ester is condensed with the anion of dimethyl methylphosphonate as produced using n-butyllithium. For this purpose, acids of the general formula

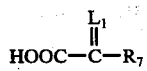

are employed in the form of their lower alkyl esters, preferably methyl or ethyl. The methyl esters for example are readily obtained by reaction of the corresponding acids with diazomethane.

For example, when $R_7$ is

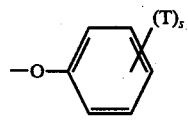

wherein T and s are as defined above, and $R_3$ and $R_4$ of the $L_1$ moiety are both hydrogen, the corresponding phenoxy or substituted phenoxy acetic acids are known in the art or readily available in the art. Those known in the art include those wherein the $R_7$ moiety is: phenoxy, (o-, m-, or p-)tolyloxy-, (o-, m-, or p-)ethylphenoxy-, 4-ethyl-o-tolyloxy-, (o-, m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-) chlorophenyoxy-, (2,3-, 2,4-, 2,5-, 2,6-, 3,4-, or 3,5-)dichlorophenoxy-, (o-, m-, or p-)trifluoromethylphenoxy-, or (o-, m-, or p-)methoxyphenoxy-.

Further, many 2-phenoxy- or substituted phenoxy propionic acids are readily available, and are accordingly useful for the preparation of the acids of the above formula wherein one and only one of $R_3$ and $R_4$ of the $L_1$ moiety is methyl and $R_7$ is phenoxy or substituted phenoxy. These 2-phenoxy or 2-substituted phenoxy propionic acids include those wherein the $R_7$ moiety is p-fluorophenoxy-, (o-, m-, or p-)chlorophenoxy-, (2,3-, 2,4-, 2,5-, 2,6-, 3,4-, or 3,5-)dichlorophenoxy-, (4- or 6-chloro-o-tolyloxy-, phenoxy-, (o-, m-, or p-)tolyloxy, 3,5-xylyloxy-, or m-trifluoromethylphenoxy-.

Finally there are available many 2-methyl-2-phenoxy- or (2-substituted)phenoxypropionic acids, which are useful in the preparation of the above acids wherein $R_3$ and $R_4$ of the $L_1$ moiety are both methyl and $R_7$ is phenoxy or substituted phenoxy. These 2-methyl-2-phenoxy-, or (2-substituted)phenoxypropionic acids include those wherein $R_7$ is: phenoxy-, (o-, m-, or p-) chlorophenoxy-, (2,3-, 2,4-, 2,5-, 2,6-, 3,4-, or 3,5-)dichlorophenoxy-.

Other phenoxy substituted acids are readily available by methods known in the art, for example, by Williamson synthesis of ethers using an α-halo aliphatic acid or ester with sodium phenoxide or a substituted sodium phenoxide. Thus, the $(T)_s$-substituted sodium phenoxide is reacted with, for example, the α-chloro aliphatic acid, or the alkyl ester derivative thereof, with heating to yield the acid of the above general formula, which is recovered from the reaction mixture by conventional purification techniques.

There are further available phenyl substituted acids of the above formula wherein $R_7$ is phenyl, benzyl, phenylalkyl, or substituted phenyl, benzyl, or phenylalkyl.

For example, when 1 is one and $R_3$ and $R_4$ of the $L_1$ moiety are both hydrogen, there are available the following phenyl or substituted phenyl propionic acids: (o-, m-, or p-)-chlorophenyl-, p-fluorophenyl-, m-trifluoromethylphenyl-, (o-, m-, or p-)methylphenyl-, (o-, m-, or p-)methoxyphenyl-, (2,4-, 2,5-, or 3,4-)dichlorophenyl-, (2,3- 2,4-, 2,5-, 2,6-, or 3,4-)dimethylphenyl-, or (2,3-, 2,4-, 2,5-, 2,6-, 3,4-, or 3,5-)dimethoxyphenyl-.

When one and only one or $R_3$ and $R_4$ of the $L_1$ moiety is methyl and 1 is one, there are available, for example, the following 2-methyl-3-phenyl or substituted phenyl propionic acids: phenyl, o-chlorophenyl-, (o-, or p-)methylphenyl-, (o-, m-, or p-)methoxy-m (2,4- or 3,4-)difluorophenyl-, 2,3-dimethylphenyl-, and (2,3-, 3,4-, or 4,5-)dimethoxyphenyl-.

When both $R_3$ and $R_4$ are methyl and 1 is one, there are available, for example, the following 2,2-dimethyl-3-phenyl or substituted phenyl propionic acids: phenyl- and p-methylphenyl.

When one and only one of $R_3$ and $R_4$ is fluoro and 1 is one, there is available, for example, 2-fluoro-3-phenyl propionic acid.

Phenyl substituted acids (as above wherein $R_7$ is aralkyl) are available by methods known in the art, for example, by reacting a mixture of the appropriate methyl- or fluoro-substituted acetic acid, with a solution of a secondary amine (e.g., diisopropylamine), and n-butyllithium in an organic diluent (e.g., tetrahydrofuran) with the appropriately substituted benzyl chloride. Thus, the above acid is obtained by the following reaction (when 1 is not zero);

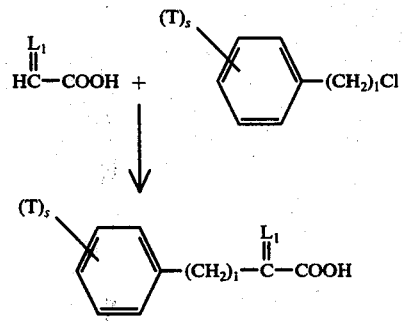

The above reaction proceeds smoothly, ordinarily at 0° C. The product acid is recovered using conventional methods.

For the acids of the above formula wherein $R_7$ is n-alkyl, many such acids are readily available.

For example, when $R_3$ and $R_4$ of the $L_1$ moiety are both hydrogen there are available butyric, pentanoic, hexanoic, heptanoic, and octanoic acids.

For example, when and only one of $R_3$ and $R_4$ of the $L_1$ moiety is methyl, there are available the following 2-methyl alkanoic acids: butyric, pentanoic, hexanoic, heptanoic, and octanoic.

For example, when one of $R_3$ and $R_4$ of the $L_1$ moiety is fluoro there are available the following 2-fluoro alkanoic acids: butyric, pentanoic, hexanoic, heptanoic, and octanoic.

The acids of the above general formula wherein $R_7$ is alkyl and $R_3$ and $R_4$ of the $L_1$ moiety are fluoro are conveniently prepared from the corresponding 2-oxoalkanoic acids, i.e. butyric, pentanoic, hexanoic, heptanoic, and octanoic. The transformation of these 2-oxoalkanoic acids to the corresponding 2,2-difluoro alkanoic acids proceeds by methods known in the art, using known ketonic fluorinating reagents. For example, $MoF_6.BF_3$ is advantageously employed in the fluorination.

The formula XII compound is transformed to the formula XIII compound by catalytic hydrogenation.

For example, conventional methods for hydrogenation of unsaturated prostanoic acid derivatives are employed. Thus a 5–10 percent palladium-on-carbon catalyst at low pressure (above or near atmospheric) is employed.

The formula XIV compound is prepared from the formula XII or XIII 3-oxo bicyclic acetal lactone by transformation of the 3-oxo-moiety to the $M_5$ moiety.

The above 3-oxo bicyclic acetal lactone is transformed to the corresponding $3\alpha$ or $3\beta$-hydroxy bicyclic acetal lactone, wherein $M_5$ is or

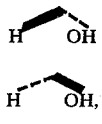

by reduction of the 3-oxo moiety, followed by optional separation of the $3\alpha$- and $6\beta$-hydroxy epimers. For this reduction the known ketonic carbonyl reducing agents which do not reduce ester or acid groups or carbon-carbon double bonds (when such reduction is undesirable) are employed. Examples of these agents are the metal borohydrides, especially sodium, potassium, and zinc borohydrides, lithium(tri-tert-butoxy)-aluminum hydride, metal trialkyl borohydrides, e.g. sodium trimethoxy borohydride, lithium borohydride, and the like. In those cases in which carbon-carbon double bond reduction need not be avoided, the boranes, e.g. disiamylborane (bis-3-methyl-2-butyl borane) are alternatively employed.

For the production of C-15 epimerically pure prostaglandins, the 15-epi compound is separated from the mixture by methods known in the art. For example, silica gel chromatography is advantageously employed.

The 3-oxo bicyclic acetal lactone is transformed into the corresponding (3RS)-3-methyl bicyclic acetal lactone wherein $M_5$ is a mixture of and

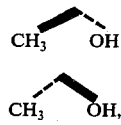

by reaction of the 3-oxobicyclic acetal lactone with a Grignard reagent, $CH_3MgHal$, wherein Hal is chloro, bromo, or iodo. The Grignard complex is thereafter hydrolyzed, for example, using saturated aqueous ammonium chloride as is known in the art. An alternate method for transforming the 3-oxo compound to a 3(RS)-3-methyl compound is by reaction of the 3-oxo bicyclic acetal lactone with trimethylaluminum.

The preferred method for separation of these (3RS)-3-methyl epimers is by separation of the corresponding C-15 epimers of the TXB-type, methyl esters using silica gel chromatography or high pressure liquid chromatography (HPLC). The formula XV compound is then prepared from the formula XI compound by reduction of the formula XIV acetal lactone to an acetal lactol. Methods known in the art are employed. For example, diisobutylaluminum hydride is employed at $-60°$ to $-78°$ C.

Chart A (Part II) provides a method whereby the formula XVI compound as prepared in Chart A (Part I) is transformd to a cis-4,5-didehydro-thromboxane analog according to formula XXIV. With respect to Chart A (Part II) the formula XVII compound is prepared from the formula XVI compound by etherifying the free hydroxyl. This etherification proceeds by methods described above for the introduction of blocking groups according to $R_{10}$. Thereafter, the formula XVII compound so produced is transformed to the corresponding lactol of formula XVIII employing diisobutyl aluminum hydride, as discussed above.

The formula XIX compound is then prepared from the formula XVIII compound employing methods known in the art. For example, the transformation of $\gamma$-lactols to corresponding prop-1-enyl, compounds as described in U.S. Pat. No. 3,920,327. In particular, see the discussion relating to Chart O of this patent. Thus, the formula XVIII lactol is reacted with methylenetriphenylphosphorane or methyltriphenylphosphonium bromide. The latter reaction proceeds as is generally known in the art, by first mixing the methyltriphenylphosphonium bromide with sodio dimethylsulfinylcarbanide, at ambient temperature, and thereafter adding the formula XVIII lactol.

The formula XIX compound is then converted to the corresponding formula XX or primary alcohol by methods known in the art, for example, as in the above cited U.S. Pat. No. 3,920,723 (see the discussion pertaining to Chart O). Thus, hydroboration effects this transformation.

Thereafter, the formula XX compound is transformed to corresponding formula XXI compound by silylation of both the primary and secondary alcohols of the formula XX compound. For this purpose trimethylsilyl is an especially preferred silylating group. The use of a especially stable silyl group (e.g. t-butyldimethylsilyl) should be avoided. Thereafter this formula XXI silylated compound is oxidized to the corresponding aldehyde, employing methods described in U.S. Pat. No. 4,020,173. See, for example, the discussion pertaining to Chart A therein, particularly the transformation of the formula XXX to formula XXXI compound. Thus, for this purpose the Collins reagent is employed by methods known in the art. See R. Ratcliffe, et al., Journal of Organic Chemistry, 35, 4000 (1970).

This formula XXII aldehyde is first hydrolyzed to the formula XXII lactol and then transformed to the formula XXIV compound by a Wittig carboxyalkylation. Accordingly, the appropriate ($\omega$-carboxyalkyl) triphenylphosphonium bromide is employed, as described above. When $R_1$ is not hydrogen, the preparation of the formula XXIV compound additionally requires esterification of the free acid produced by the Wittig alkylation. Procedures and methods for accomplishing this esterification are described below.

By the procedure of Chart A (Part III), the formula XXV lactol is transformed to the corresponding formula XXVII 5-oxa-11-deoxy-11$\alpha$- or 11$\beta$-alkoxy-$TXB_1$-type compound. First the formula XXVI compound is obtained by reduction of the formula XXV lactol, for example, with aqueous methanolic or ethanolic sodium borohydride to the formula XXVI compound. Alternatively, and preferably, the formula XXVI compound is obtained by a one step reduction of the formula XVII lactone of Chart A (Part II), for example, with lithium aluminum hydride or diisobutyl aluminum hydride at a temperature ranging from 0° to 35° C. For preparing the formula XXVII compound, a Williamson synthesis is employed followed by hydrolysis of the blocking group. For example, the formula XXVI compound is condensed with a haloalkanoate within the scope of $$Hal-(CH_2)_g-CH_2-COOR_1,$$

wherein Hal is chloro, bromo, or iodo and $g$ is as defined above. Normally the reaction is done in the presence of a base such as n-butyllithium, phenyllithium, trimethyllithium, sodium hydride, or potassium t-butoxide.

Alternatively and preferably, an ortho-4-bromoalkanoate is employed. Such reagents are available or are prepared by methods known in the art, for example, from the appropriate halonitrile by way of the corresponding imino ester hydrohalide as illustrated hereinafter.

The condensation is conveniently run in a solvent, such as tetrahydrofuran or dimethyl sulfoxide or especially if an organolithium compound is employed, preferably with addition of dimethylformamide or hexamethylphosphoramide. The reaction proceeds smoothly at −20° to 50° C., but is preferably performed at ambient temperature. Following the condensation, the formula XXVII compound is obtained by methods known in the art, for example, by hydrolysis in cold dilute mineral acid.

With regard to Chart A (Part IV), the formula XXIX compound is prepared from the formula XXVIII compound by a Wittig alkylation, using the appropriate (ω-carboxyalkyl)triphenylphosphonium bromide. The reaction proceeds as is generally known in the art, by first mixing the appropriate (ω-carboxyalkyl)triphenylphosphonium bromide with sodio dimethyl sulfinylcarbanide, at ambient temperature, and adding the formula XXVIII lactol to this mixture. Thereafter the carboxy hydrogen of the compound so formed is transformed to an $R_1$ moiety by the methods and procedures hereinbelow described.

The formula XXX compound is prepared from the formula XXIX compound by catalytic hydrogenation of the formula XXVIII compound. Methods known in the art for transformation of $PG_2$-type compounds to $PG_1$-type compounds are employed. Accordingly, metal catalysts (e.g. palladium) on a suitable support (e.g. carbon) at about 0° C. are employed under a hydrogen atmosphere. See for reference B. Samuelsson, Journal of Biological Chemistry 239, 491 (1974). Accordingly there is prepared the formula XXX 11-deoxy-11α- or 11β-deoxy-TXB$_1$-type compound.

Alternatively, and preferably the method of Chart A (Part VI) is employed in the preparation of TXB$_1$ analogs as in formula XXX.

With regard to Chart A (Part V) the formula XXXII compound is prepared from the formula XXXI compound by optional reduction and a separation of any mixed 15-epimers.

The mixed C-15 epimers are separated by conventional (e.g. chromatographic) means for separating diastereomeric mixtures. When 15-methyl-TXB analogs are prepared (i.e. $R_6$ is hydrogen, $R_5$ is methyl) epimeric separation is deferred until after the deacetalization, since the deacetalization conditions result in C-15 epimerization in this case. Otherwise, C-15 epimers are optionally separated at any convenient point in the synthesis of Chart A.

Finally the reduction proceeds with reagents known to reduce carboxylic acids to corresponding primary alcohols. For example, when the formula XXXII compound is an acid or an ester, the reduction proceeds with lithium aluminum hydride or diisobutylaluminum hydride.

Useful solvents include diethyl ether, tetrahydrofuran, dimethoxyethane, or like organic solvents. The reaction is conveniently run at temperatures of about −78° C. to 100° C., although preferably at about 0° C. to 50° C. When the formula XXXII compound is an acid, reducing agents such as diborane are also employed when double bond reduction is not a problem.

Thereafter the formula XXXIII compound is prepared by optional dialkylacetalizing the formula XXII compound, See methods described in U.S. Pat. No. 4,020,173 for the analogous transformation.

Chart A (Part VI) provides a method whereby the formula XXXIV compound (prepared as described in U.S. Pat. No. 4,020,173 is transformed into a formula XXXIX TXB$_1$ analog.

The formula XXXV compound is prepared from the formula XXXIV compound by reduction of the formula XXXIV lactone to a lactol, for example, as described in Chart A (Part I) for the transformation of the formula XIV compound to the formula XV compound.

Thereafter, the formula XXXV compound is Wittig carboxyalkylated as described in Chart A (Part IV).

This formula XXXVI compound is then subjected to catalytic hydrogenation, whereby the cis-5,6-unsaturation is removed and the arylmethyl hydroxy-hydrogen replacing group according to $R_{34}$ is hydrogenolyzed. Methods known in the art are employed. For example, see the procedure and references cited in Chart A (Part IV) for the transformation of the formula XXIX compound to the formula XXX compound.

Further, the formula XXXVIII compound is prepared from the formula XXXVIII compound by oxidation of the formula XXXVII primary alcohol to the corresponding aldehyde. For this purpose, Moffatt oxidation conditions are employed, as described in U.S. Pat. No. 4,020,173 for the transformation of the formula LXIII compound of Chart C therein to the formula LXIV compound.

Thereafter, the formula XXXVIII compound is transformed to the formula XXXIX TXB$_1$ analog by methods and procedures hereinabove described in Chart A. For example, first the formula XXXVIII compound is subjected a Wittig oxoalkylation as described in Chart A (Part I); thereafter optionally hydrogenated (when $Y_1$ is —CH$_2$CH$_2$—); the oxo moiety reduced or methylated, thereby transforming it to an $M_5$ moiety; the resulting compound thereafter optionally dealkylacetalated; and finally any mixed epimeric alcohols are separated by conventional means.

Chart D (Parts I and II) provide a methods whereby the formula LXI PGF$_\alpha$-type, 11,15-diacylate or bis(ether) or formula LXIX PGF$_\alpha$-type, 1,9-lactone, 15-acylate or ether is transformed to the various formula LXVI or LXVII thromboxane analogs. The formula LXI compound of Chart D is known in the art or prepared by methods known in the art. For example, Chart B provides a method whereby various PGF$_\alpha$-type compounds are transformed to corresponding PGF$_\alpha$-type 9,15-diacylates. The formula LXIX is prepared, as described in Chart D (Part II) from the readily available formula LXVIII compound. See Chart B, formula XLIII. Chart B requires as starting material various formula XL PGF$_\alpha$-type compounds which are known in the art or readily prepared by methods known in the art. For example, when $Z_1$ of formula XL is the same as $Z_4$, then the various compounds so depicted are prepared by general methods described in Chart A employing as starting material a bicyclic lactone aldehyde of the formula

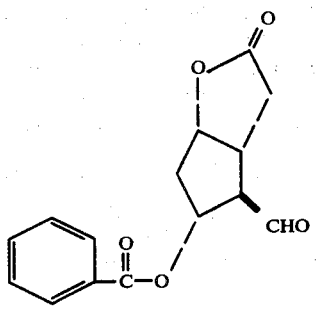

and modifying the reaction sequence of Chart A by methods such as those described in E. J. Corey, et al., JACS 92:397 (1970). Otherwise, the method of Chart C provides such compounds wherein $Z_1$ is

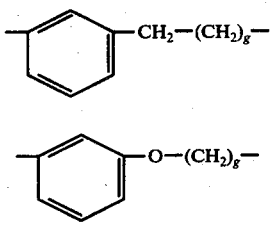

from known starting materials.

Thus, with respect to Chart B one method is provided whereby the formula XL $PGF_\alpha$-type compound is transformed to the $PGF_\alpha$, 15-acylate or 5-ether of formula XLIII or to the $PGF_\alpha$, 9,15-diacylate or 9,15-bis(ether) formula L, which is required as starting material for the process steps of Chart D.

In many cases, simpler more direct methods are available for the preparation of such diacylates and bis(ethers) and are preferably employed in place of the method of Chart B. For example, when there is no steric hinderance about C-15, e.g., when $R_3$, $R_4$, and $R_5$ are all hydrogen, formula XL compound is transformed to an 11,15-bis-silyl ether according to the selective silylation procedure described in the transformation of the formula XLIII compound to the formula XLVIII compound. This bis(silyl ether) is then acylated or etherified as in the transformation of the formula XLI compound to the formula XLII compound and the silyl group thereafter hydrolyzed, either by general methods or when $R_{10}$ blocking groups are introduced, by the selective procedures described above. Thereafter the procedure described in U.S. Pat. No. 4,020,173 is employed for the 15-monoacylation or 15-mono etherification of the resulting $PGF_\alpha$-type 9-acylate.

Alternatively, when, for example, $R_5$ is methyl the formula XL compound is transformed to a corresponding 11-silyl ether by this selective silylation procedure referred to above. This 11-silyl ether is then acylated or etherified at C-9 and C-15, as described above, and finally the silyl group is hydrolyzed, under selective conditions as required, as described above, yielding the desired diacylate or bis(ether).

In any event, however, the process of Chart B invariably provides, in high yield, the required 9,15-diacylate, or 9,15-bis(ether) regardless of the steric hindrance or lack thereof, of the formula XL starting material.

The formula XLI compound is prepared from the formula XL compound by cycloalkyl or aryl boronization. Accordingly, the formula XLI compound is prepared by reaction of the formula XL compound with a slight stoichiometric excess of the corresponding alkyl or aryl boronic acid. The course of the reaction is conveniently monitored by gas chromatography and the reaction is preferably carried forth on vigorous stirring at reflux temperatures. The preferred reaction diluent for the transformatin is methylene chloride, although other suitable organic solvents are likewise employed.

The formula XLII compound is then prepared from the formula XLI compound by introduction of a hydroxy-hydrogen replacing group according to $R_{31}$ at C-15. Methods and procedures described in U.S. Pat. No. 4,020,173 are employed. The choice of the replacing group herein is made in accord with considerations of convenience and ready availability of reactants, and thus, for example, acetyl groups provide conveniently employable moieties. Further, arylmethyl groups must be avoided where unsaturated thromboxane analogs are to be prepared in Chart D.

The formula XLIII compound is then prepared from the formula XLII compound by decycloboronization. For this purpose an alkaline metal hydroxide (e.g. sodium, lithium, or potassium hydroxide) is combined with the formula XLII compound in a water miscible diluent capable of yielding a homogeneous reaction mixture (e.g. methanol or ethanol), and the resulting solution is thereafter treated with dilute aqueous hydrogen peroxide. However, when acyl protecting groups according to $R_9$ are employed in the preceding reaction, the decycloboronization conditions must be adjusted to avoid deacylation. Thus alkanoic hydrogen peroxide in the presence of no more than a trace of hydroxide is employed at about 30° C.

The formula XLIII compound is then selectively monosilylated at C-11, thereby preparing the formula XLVIII compound. For this selective monosilylation procedures described in U.S. Pat. No. 3,822,303 issued July 2, 1974; German Offenlegungsschrift Pat. No. 2,259,195 (Derwent Farmdoc CPI No. 36457U-B) or Netherlands Pat. No. 7,214,142 (Derwent Farmdoc CPI No. 2622U-B) are employed. Silyl groups, are selected from those described hereinabove according to the criteria set forth when selective silylations are to be employed.

The formula XLIX compound is then prepared from the formula XLVIII compound by acylation or etherification at C-9. Methods and procedures described above for the introduction of hydroxy-hydrogen replacing groups according to $R_{31}$ are employed. Finally, the formula L $PGF_\alpha$-type 9,15-diacylate or 9,15-bis(ether) is prepared from the formula XLIX compound by hydrolysis of the silyl group at C-11. Methods known in the art and described above for the hydrolysis of silyl groups (mild acidic conditions or selective hydrolytic conditions) are employed.

As discussed above, Chart C provides a method whereby the formula LI 3,7-inter-m-phenylene- or 3,7-inter-m-phenylene-3-oxa-$PGF_\alpha$-type compound is transformed to a like formula LVII with various terminal side chains. The compounds according to formula LI which are employed as starting material for Chart C are known in the art or readily available by methods known in the art. For example, see U.S. Pat. No. 3,933,900, particularly Chart L therein which describes the preparation of 3,7-inter-m-phenylene-3-oxa-$PGF_{2\alpha}$.

With respect to Chart C, the formula LII compound is prepared from the formula LI compound by cleavage of the 13,14-trans double bond, conveniently by ozonolysis. Ozonolysis proceeds by bubbling dry oxygen, containing about 3 percent ozone, through a mixture of a formula LI compound in a suitable nonreactive diluent. For example, n-hexane is advantageously employed. The ozone may be generated using methods known in the art. See, for example, Fieser, et al., "Reagents for Oganic Synthesis," John Wiley and Sons, Inc. (1967), pages 773-777. Reaction conditions are maintained until the reaction is shown to be complete, for example, by silica gel thin layer chromatography or when the reaction mixture no longer rapidly decolorizes a dilute solution of bromine in acetic acid.

The formula LIII compound is prepared from the formula LII compound by acylation, employing methods described above for introducing acyl protecting groups according to $R_9$.

The formula LIV compound is then prepared from the formula LIII compound employing a phosphonate of the formula:

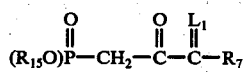

wherein $R_{15}$, $L_1$, and $R_7$ are as defined above. Phosphonates of this general formula are prepared by methods known in the art. See the text hereinabove accompanying Chart A for discussion of the preparation and the appropriate reaction conditions by which the Wittig reaction proceeds. The formula LV compound is prepared from the formula LIV compound by transformation of the C-13 to C-14 trans—CH=CH—moiety to a $Y_1$ moiety. Methods discussed in Chart A above are employed.

The formula LV compound is then transformed to the corresponding formula LVI compound by transformation of the 15-keto to an $M_5$ moiety, employing methods described above in Chart A.

Finally the formula LVI compound prepared above is transformed to the formula LVII compound by deacylation, employing methods described above for removal of acyl protecting groups according to $R_9$, followed by a chromatographic separation of C-15 epimeric mixtures.

Chart D provides a method whereby the various $TXB_2$ analogs herein are prepared from the formula LXI compound compound. Chart D provides a preferred method for preparing compounds wherein $Y_1$ is trans—CH=CH—. For those formula XLV or XLVI compounds wherein $Z_1$ contains no double bonds, and $Y_1$ is —$CH_2CH_2$—, a modified method according to Chart D is employed as the preferred method for preparing such compounds, which comprises employing an unsaturated formula LXI or LXIX starting material (i.e., $Y_1$ is trans-CH=CH—) transforming this material to the corresponding formula LXIV or LXXII compound, catalytically hydrogenating this formula LXIV or LXXII compound, and finally proceeding to the desired product as in Chart D (Part I).

With regard to Chart D (Part I), the formula LXI compound is transformed to the formula LXII aldehyde by reaction with lead tetraacetate in benzene. The reaction proceeds rapidly at temperatures of about 40° to 60° C., and is ordinarily complete within about 45 min. to 2 hr. The resulting formula LXII product exhibits limited stability and is accordingly converted to the formula LXIII acetal without further purification.

The preparation of the formula LXIII dialkyl acetal proceeds by methods known in the art for the preparation of acetals from aldehydes, e.g. reaction with an alkanol in the presence of a triallyl, orthoalkanoate and catalytic amount of an acid. See U.S. Pat. No. 4,020,173. Thus, when $R_{33}$ is methyl, the present reaction proceeds by treatment of the formula LXII compound with methanol, methylorthoformate, and pyridine hydrochloride. Pure formula LXIII product is thereafter isolated by conventional methods, such as chromatography.

The formula LXIV compound is then prepared from the formula LXIII compound by removal of the diacyl of bis-(ether) groups. Methods described hereinabove are employed. For example, when $R_{31}$ is acyl, sodium methoxide in methanol is employed in stoichiometric amounts, yielding the formula LXIV trihydroxy acetal. Optionally, the use of aqueous methanolic sodium hydroxide removes both such acyl protecting groups and the $R_1$ ester.

The formula LXV compound is then prepared from the formula LXIV compound by hydrolysis of the acetal group. Methods described above for the hydrolysis of tetrahydropyranyl ethers (i.e. acetic acid, water, and tetrahydrofuran mixtures) yield the formula LXV product. More vigorous conditions of hydrolysis of the formula LXIV compound yield the formula LXVI product wherein $R_6$ is hydrogen directly.

Optionally, however, the formula LXV compound is prepared directly form the formula LXII compound when $R_{31}$ is an acyl protecting group according to $R_9$ by treatment of such a formula LXII compound with an alkanol and anhydrous mineral acid in diethyl ether. When $R_{33}$ is methyl, for example, methanol and ethereal 2N hydrochloric acid yield the formula LXV compound directly form such a formula LXII reactant.

Finally, the formula LXVI and LXVII compounds are prepared as described in Chart A for the preparation of the formula XXXII and formula XXXIII compounds, respectively, from the formula XXXI reactant.

With respect to Chart D (Part II) an alternate method is provided for the preparation of the formula LXXII compound, which compound being identical to the formula LXIV compound of Chart D (Part I), is useful in the synthesis of various compounds of the present invention. The formula LXIX compound of Chart D is successively transformed to the formula LXX, formula LXXI, and formula LXXII compounds as in the corresponding transformations of Chart D (Part I) wherein the formula LXI compound is successively transformed to the formula LXII, formula LXIII, and formula LXIV compound respectively.

The formula LXIX compound is prepared from the formula LXVIII reactant (available as the formula XLIII compound of Chart B, according to process of that Chart) by a 1,9-lactonization. This 1,9-lactonization proceeds by methods known in the art. For a discussion of a general method for preparing large ringed lactones, see E. J. Corey, Journal of the Americal Chemical Society 96, 5614 (1974); and for a discussion of the 1,9-lactonization of $PGF_{2\alpha}$ see E. J. Corey, et al., Journal of the Americal Chemical Society 97, 653 (1975). Thus, by this lactonization procedure the formula LXVII free acid is transformed to a 2-pyridine thiol ester by reaction of the formula LXVIII free acid with 1.5 equivalents of 2,2'-dipyridyldisulfide and 1.5 equivalents of triphenylphosphine in dry (anhydrous) oxygen-free xylene or benzene. The 2-pyridinethiol esterification proceeds at room temperature, in about 2 to 24 hr. Thereafter ring closure is accomplished by first diluting the thiol ester with dry oxygen-free xylene or benzene and thereafter heating at reflux for 1 to 24 hr.

In the reaction sequence described by Charts B and D, the use of C-1 esters, particularly and especially lower alkyl esters, is preferred.

In each of the above Charts, diastereomeric mixtures, other than anomeric mixtures, when produced by any reaction step herein, are separated immediately by isolation and conventional separation techniques, e.g., chromatography.

Optically active TXB analogs and related products are obtained from optically active intermediates, according to the process steps of the above charts. Likewise racemic $TXB_2$ analogs are obtained from corresponding racemic $TXB_2$ intermediates following the procedures in the above charts, e.g. when racemic intermediates are used in the reactions above, racemic products are obtained.

In all of the above described reactions, the products are separated by conventional means from starting material and impurities. For example, by use of silica gel chromatography monitored by thin layer chromatography the products of the various steps of the above charts are separated from the corresponding starting materials and impurities.

As discussed above, the processes herein described lead variously to primary alcohols acids ($R_1$ is hydrogen) or to esters.

When the alkyl ester has been obtained and an acid is desired, saponification procedures, as known in the art for PGF-type esters are employed. Optionally, however, free acids are prepared by enzymatic process for transformation of PGE-type esters to their acid forms. Thus the TXB-type, methyl ester is combined with prepared enzyme powder and hydrolyzed. See for reference E. G. Daniels, Process For Producing An Esterase, U.S. Pat. No. 3,761,356.

When an acid has been prepared and an alkyl, cycloalkyl, or aralkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbns are known in the art or can be prepared by methods known in the art. See, for example, Organic Reactions, John Wiley and Sons, Inc., New York, N.Y. vol. 8, pp. 389–394 (1954).

An alternative method for alkyl, cycloalkyl or aralkyl esterification of the carboxy moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Various methods are available for preparing phenyl or substituted phenyl esters within the scope of the invention from corresponding aromatic alcohols and the free acid TXB-type compounds, differing as to yield and purity of product.

Thus by one method, the TXB-type compound is converted to a tertiary amine salt, reacted with pivaloyl halide to give the mixed acid anhydride and then reacted with the aromatic alcohol. Alternatively, instead of pivaloyl halide, an alkyl or arylsulfonyl halide is used, such as p-toluenesulfonyl chloride. See for example Belgian Pat. Nos. 775,106 and 776,294, Derwent Farmdoc Nos. 33705T and 39011T.

Still another method is by the use of the coupling reagent, dicyclohexylcarbodiimide. See Fieser et al., "Reagents for Organic Synthesis", pp. 231–236, John Wiley and Sons, Inc., New York, (1967). The TXB-type compound is contacted with one to ten molar equivalents of the aromatic alcohol in the presence of 2–10 molar equivalents of dicyclohexylcarbodiimide in pyridine as a solvent.

One preferred novel process for the preparation of these esters, however, comprises the steps:

a. forming a mixed anhydride with the TXB-type compound and isobutylchloroformate in the presence of a tertiary amine and b. reacting the anhydride with an appropriate aromatic alcohol.

The mixed anhydride described above is formed readily at temperatures in the range $-40°$ to $+60°$ C., preferably at $-10°$ to $+10°$ C. so that the rate is reasonably fast and yet side reactions are minimized. The isobutylchloroformate reagent is preferably used in excess, for example 1.2 molar equivalents up to 4.0 per mole of the TXB-type compound. The reaction is preferably done in a solvent and for this purpose acetone is preferred, although other relatively nonpolar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The aromatic alcohol is preferably used in equivalent amounts or in substantial stoichiometric excess to insure that all of the mixed anhydride is converted to ester. Excess aromatic alcohol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. Although they are effectively used, 2-methylpyridine and quinoline result in a slow reaction. A highly hindered amine such as 2,6-dimethyllutidine is, for example, not useful because of the slowness of the reaction.

The reaction with the anhydride proceeds smoothly at room temperature (about 20° to 30° C.) and can be followed in the conventional manner with thin layer chromatography (TLC).

The reaction mixture is worked up to yield the ester following methods known in the art, and the product is purified, for example by silica gel chromatography.

Solid esters are converted to a free-flowing crystalline form on crystallization from a variety of solvents, including ethyl acetate, tetrahydrofuran, methanol, and acetone, by cooling or evaporating a saturated solution of the ester in the solvent or by adding a miscible non-solvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 75° C. Although the crystals are normally pure enough for many applications, they may be recrystallized by the same general techniques to achieve improved purity after each recrystallization.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinbove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 or 137 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on an CEC model 21-110B Double Focusing High Resolution Mass Spectrometer on an LKB Model 9000 Gas-Chromatograph-Mass Spectrometer. Trimethylsilyl derivatives are used, except where otherwise indicated.

"Brine" herein, refers to an aqueous saturated sodium chloride solution.

The A-IX solvent system used in thin layer chromatography is made up from ethyl acetate-acetic acid-cyclohexane-water (90:20:50:100) as modified from M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

EXAMPLE 1

2,2-Difluoro-TXB$_2$ (Formula XXXII M$_1$ is

Z$_4$ is cis—CH=CH—(CH$_2$)$_2$—CF$_2$—, Y$_1$ is trans—CH=CH—, R$_1$, R$_3$, R$_4$, and R$_6$ are hydrogen, and R$_7$ is n-butyl) its methyl ester, the 11α-methyl acetals thereof or the 15-epimers thereof.

Refer to Chart A (Parts I, IV, and V).

A. 2β-Carboxaldehyde-4α-hydroxy-6α-methoxy-3α-tetrahydropyranacetic acid γ-lactone as prepared in U.S. Pat. No. 4,020,173, Example 14, part A (425 mg.) is dissolved in 20 ml. of diethyl ether and the solution treated with 4.8 ml. of 0.5 M 2-oxo-heptylidine-tri-n-butyl phosphorane in diethyl ether. After 20 min., the reaction mixture is evaporated and the residue chromatographed on 80 g. of silica gel. The column is eluted with ethyl acetate in n-hexane (1:1) and fractions containing pure 3α-hydroxy-5α-methoxy-2β-(3-oxo-trans-1-octenyl)-3α-tetrahydropyranacetic acid γ-lactone, a formula XII compound, are combined (524 mg.) NMR absorptions are observed at 0.6–1.9, 1.9–3.0, 3.33, 4.25, 4.5–5.0, 6.4, and 6.80 δ. Infrared absorptions are observed at 2900, 1780, 1670, 1160, 1130, 1070, 1050, and 1025 cm.$^{-1}$. The mass spectrum exhibits parent peak at 296.1589. Silica gel TLC R$_f$ is 0.43 in ethyl acetate and Skellysolve B (1:1).

B. To a mixture of 2.18 g. of anhydrous zinc chloride and 15 ml. of 1,2-dimethoxyethane under a nitrogen atmosphere is added with stirring 0.61 g. of sodium borohydride. The resulting mixture is then stirred at ambient temperature for 2 hr. and thereafter cooled to −15° C. A solution of 1.17 g. of the reaction product of Part A in 10 ml. of 1,2-dimethoxyethane is then added dropwise over about 2 min. The mixture is then stirred at −15° C. for 2 hr., thereafter at 0° C. for one hr. and finally at ambient temperature for about 1.5 hr. The mixture is then cooled to 0° C. and 4.4 ml. of water is added dropwise, with caution (hydrogen gas evolution). The resulting mixture is then diluted with 75 ml. of ethyl acetate and filtered through Celite. The filtrate is then washed with 30 ml. of brine and the organic layer dried over magnesium sulfate and concentrated under reduced pressure. The resulting residue (1.24 g.) is then chromatographed on 125 g. of silica gel, deactivated by addition of 25 ml. of ethyl acetate. Eluting with 500 ml. of ethyl acetate and hexane (3:1) and 500 ml. of ethyl acetate affords 1.05 g. of 4α-hydroxy-6α-methoxy-2β-[(3RS)-3-hydroxy-trans-1- acid octenyl]-3α-tetrahydropyranacetic γ-lactone (formula XIV). Epimeric alcohols are then separated employing silica gel thin layer chromatography, eluting with methanol and chloroform (1:19). Alternatively, the epimeric mixture of alcohols is employed directly in succeeding parts of the present example. For the epimeric mixture, a characteristic NMR absorption is observed at 3.27 δ. The mass spectrum exhibits a parent peak at 370.2194 and other peaks at 369, 345, 329, 327, 323, 229, 267, 247, 241, 199, 185, 173, and 129.

C. To a stirred solution of 1.05 g. of the epimeric mixture of the reaction production of part C in 15 ml. of toluene and 10 ml. of dry tetrahydrofuran at −78° C. under a nitrogen atmosphere is added 15 ml. of a 10 percent solution of diisobutylaluminum hydride in toluene over a 5 min. period. The mixture is stirred for 20 min. and thereafter a solution of 3 ml. of water and 10 ml. of tetrahydrofuran is added cautiously with vigorous stirring. The resulting mixture is allowed to warm to ambient temperature and then filtered through Celite, rinsing with ethyl acetate. The filtrate is then shaken with 30 ml. of brine and the resulting mixture filtered through Celite. The filtrate is then washed with brine, and concentrated under reduced pressure to yield 1.0 g. of a formula XV compound; 4α-hydroxy-6α-methoxy-2β-[(3RS)-3-hydroxy-trans-1-octenyl]-3α-tetrahydropyran acetic acid γ-lactol, an oil. Silica gel TLC $R_f$ is 0.21 and 0.24 in methanol and chloroform (1:19).

Alternatively reaction product of part C is prepared directly from the reaction product of part A as follows:

The reaction product of part A (500 mg.) is dissolved in 10 ml. of tetrahydrofuran and the solution cooled to −78° C. under an argon atmosphere. This stirred solution is then treated over 30 min. with 0.7 ml. of diisobutylaluminum hydride, diluted to 2.8 ml. with toluene. The reaction mixture is then treated dropwise with 2 ml. of water and allowed to warm to ambient temperature. Ethyl acetate in 0.25 N aqueous hydrochloric acid are added to the reaction mixture, and the mixture partitioned between organic and aqueous phases. The organic phase is washed with brine, dried over magnesium sulfate and concentrated under reduced pressure to yield 0.364 g. of a crude oil, the (3RS)-3-hydroxy formula XXV compound, as above.

D. A mixture of 1.69 g. of 57 percent sodium hydride in mineral oil and 45 ml. of dry dimethylsulfoxide are stirred slowly under nitrogen at 65°–70° C. for one hr. This solution is then cooled to 15° C. and 9.0 g. of 4,4-difluoro-4-carboxybutyltriphenphosphonium bromide is added. The resulting orange mixture is then stirred for 30 min. at ambient temperature, cooled to 15° C. and the solution of 1.0 g. of the reaction product of part C in 5 ml. of dimethyl sulfoxide is added. The resulting mixture is then stirred at ambient temperature for 2.5 hr. and is then cooled to 15° C. Water is added with cooling, yielding a solution of about pH 9. This solution is then extracted with diethyl ether to remove neutral materials. To the aqueous layer is added a suspension of 10 g. of ammonium chloride in 60 ml. of brine and the resulting mixture extracted with ethyl acetate. The ethyl acetate extract is then washed with brine, dried over magnesium sulfate, and concentrated under reduced pressure. The resulting residue (1.5 g.) is is chromatographed on 100 g. of acid-washed silica gel, deactivated by addition of 20 ml. of ethyl acetate. Eluting with one l. of ethyl acetate and hexane (1:1) yields 11-deoxy-11α-methoxy-15-epi-2,2-difluoro-TXB$_2$, and 11-deoxy-11α-methoxy-2,2-difluoro-TXB$_2$.

E. Methyl esterification employing ethereal diazomethane, yields 2,2-difluoro-11-deoxy-11α-methoxy-TXB$_2$, methyl ester, or its 15-epimer.

F. A solution of one ml. of 85 percent aqueous phosphoric acid and 10 ml. of water is added with stirring to a solution of 220 mg. of the reaction product of part D the (15S)- or (15R)-epimer in 10 ml. of tetrahydrofuran. The resulting solution is then heated to 40° C. for 6 hr. and sodium chloride is thereafter added to the mixture. The resulting mixture is extracted with ethyl acetate and the ethyl acetate extract washed with brine until the aqueous layer is neutral. The organic phase is then dried over magnesium sulfate and concentrated to a residue. The residue (210 mg.) is then chromatographed on 20 g. of acid-washed silica gel, deactivated by addition of 4 ml. of ethyl acetate. Eluting with 70 ml. of ethyl acetate and hexane (3:1), and 100 ml. of ethyl acetate yields the title 2,2-difluoro TXB$_2$ or its 15-epimer respectively.

G. Methyl esterification, of the reaction product of part F, employing ethereal diazomethane, yields 2,2-difluoro-TXB$_2$, methyl ester or its 15-epimer.

EXAMPLE 2

13,14-Dihydro-TXB$_2$ (Formula XXXII: $R_1$, $R_5$ of the $M_1$ moiety, $R_3$ and $R_4$ of the $L_1$ moiety, and $R_6$ are all hydrogen, $Z_4$ is cis—CH=CH—(CH$_2$)$_3$—, $Y_1$ is —CH$_2$CH$_2$—, and $R_7$ n-butyl) its 11α-methylacetal, the methyl esters thereof, or the 15-epimers thereof.

Refer to Chart A. (parts I, IV, and V).

A. A mixture of 4 g. of the reaction product of Example 1, part A, 800 mg. of a 5 percent palladium-on-charcoal catalyst, and 400 ml. of ethyl acetate are stirred at ambient temperature under one atmosphere of hydrogen for one hr. Hydrogen uptake proceeds rapidly, and the reaction is terminated when silica gel TLC indicates the reaction is complete. The resulting mixture is then filtered through Celite and washed with ethyl acetate. The filtrate is then evaporated to yield a formula XIII compound: 3α-hydroxy-5α-methoxy-2β-(3-oxo-octyl)-3α-tetrahydropyranacetic acid γ-lactone.

B. Following the procedure of Example 1, parts B and C, the reaction product of Example 1, part A, is transformed to 4α-hydroxy-6α-methoxy-2β-[(3RS)-3-hydroxyoctyl]-3α-tetrahydropyranacetic acid γ-lactol, a formula XV compound.

C. Following the procedure of Example 1, part D, but employing 4-carboxybutyltriphenylphosphonium bromide in place of 4,4-difluoro-4-carboxybutyltriphenylphosphonium bromide there is prepared 11-deoxy-11α- methoxy-15-epi-13,14-dihydro-TXB$_2$ or 11-deoxy-11α-methoxy-13,14-dihydro-TXB$_2$.

D. Following the procedure of Example 1, part E, F, and G, there are prepared the various title products of this example: 11-deoxy-11α-methoxy-13,14-dihydro-TXB$_2$, methyl ester or its 15-epimer; 13,14-dihydro-TXB$_2$, or its 15-epimer; and 13,14-dihydro-TXB$_2$, methyl ester or its 15-epimer.

EXAMPLE 3

15-Methyl-TXB$_2$ (Formula XXXII: R$_1$, R$_6$ and R$_3$ and R$_4$ of the L$_1$ moiety are all hydrogen, R$_5$ of the M$_1$ moiety is methyl, Z$_4$ is cis—CH=CH—(CH$_2$)$_g$—, Y$_1$ is trans—CH=CH—, and R$_7$ is n-butyl) its 15-epimer, the 11α-methylacetals thereof, or the methyl esters thereof.

Refer to Chart A (Parts I, IV, and V).

A. The reaction product of Example 1, part A, in tetrahydrofuran is treated with stirring at −78° C. with 3M methyl magnesium bromide in diethyl ether, added dropwise. After 2 hr., there is added dropwise at −78° C. 10 ml. of saturated aqueous ammonium chloride. The resulting mixture is then warmed to 25° C. and shaken with diethyl ether and water. The organic phase is then washed with brine and dried and concentrated to yield 4α-hydroxy-6α-methoxy-2β-[(3RS)-3-methyl-3-hydroxy-trans-1-octenyl]-3α-tetrahydropyranacetic acid γ-lactone, a formula XIV compound.

B. Following the procedure of Example 1, parts B and C, the procedure of Example 2, part C and the procedure of Example 1, parts E, F, and G, successively, there are prepared the various title products: 11-deoxy-11α-methoxy-15-methyl-TXB$_2$, or its 15-epimer; 11-deoxy-11α-methoxy-15-methyl-TXB$_2$, methyl ester, or its 15-epimer; 15-methyl-TXB$_2$, or its 15-epimer; and 15-methyl-TXB$_2$, methyl ester, or its 15-epimer.

EXAMPLE 4

TXB$_1$ (Formula XXXII: R$_1$, R$_3$ and R$_4$ of the L$_1$ moiety, R$_5$ and R$_6$ are all hydrogen, Z$_4$ is —(CH$_2$)$_5$—, Y$_1$ is trans—CH=CH—, and R$_7$ is n-butyl) its 15-epimer, the 11α-methylacetals thereof, and the methyl esters thereof.

Refer to Chart A (Parts, I, IV and V).

A. A mixture of TXB$_2$, its 15-epimer, the 11α-methylacetals thereof, or the methyl esters thereof; a 5 percent rhodium-on-alumina catalyst; and ethyl acetate is stirred under one atmosphere of hydrogen at 0° C. until substantially all the starting material has been consumed as indicated by silica gel TLC. The resulting mixture is then filtered to remove catalyst and the filtrate is concentrated under reduced pressure. The residue so obtained is then chromatographed on silica gel and fractions containing one of the respective pure title products are combined and concentrated to yield the title compound.

EXAMPLE 5 cis-4,5-Didehydro-TXB$_1$ (Formula XXXII: R$_1$, R$_3$ and R$_4$ of the L$_1$ moiety, R$_5$ of the M$_1$ moiety and R$_6$ are all hydrogen, Z$_4$ is cis—CH$_2$—CH=CH—(CH$_2$)$_2$—, Y$_1$ is trans—CH=CH—, and R$_7$ is n-butyl) its 15-epimer, the 11α-methylacetals thereof, or Refer to Chart A (parts I, II, and V).

A. A mixture of the reaction product of Example 1, part B, (35.9 g.), 15 ml. of freshly distilled dihydropyran, and 0.3 g. of pyridine hydrochloride in 100 ml. of dichloromethane is stirred under a nitrogen atmosphere at about 25° C. for 18 hr. The resulting mixture is then diluted with cold diethyl ether and washed with ice-cold 0.1 N hydrochloric acid, water, 5 percent aqueous sodium bicarbonate, and brine. This solution is then dried and concentrated under reduced pressure and chromatographed yielding the THP ether of the starting material: 6α-methoxy-4α-hydroxy-2β-[(3RS)-3-tetrahydropyranyloxy-trans-1-octenyl]-3α-tetrahydropyranacetic acid γ-lactone, a formula XVII compound.

B. The reaction product of part A above is transformed to 6α-methoxy-4α-hydroxy-2β-[(3RS)-3-tetrahydropyranyloxy-trans-1-octenyl]-3α-tetrahydropyranacetic acid γ-lactol following the procedure of Example 1, part C.

C. Methyltriphenylphosphonium bromide (17.5 g.) is added to a solution of sodiodimethylsulfinylcarbanide prepared from sodium hydride (57 percent, 2.02 g.) and 75 ml. of dimethylsulfoxide at 65° to 70° C.) and cooled to 15° C. The resulting mixture is then stirred at 15° to 25° C. for 20 min., and cooled to 15° C. To this solution is added a mixture of the reaction product of part B above (10 g.) in 20 ml. of dimethylsulfoxide. The resulting mixture is then stirred at about 25° C. for 2.5 hr., and then shaken with water and 500 ml. of diethyl ether. The organic phase is then washed with water and brine, dried, and concentrated under reduced pressure. The residue is triturated with diethyl ether and then Skellysolve B and filtered and the filtrate evaporated to yield a residue which is chromatographed on silica gel yielding 6α-methoxy-4α-hydroxy-2β-[(3RS)-3-tetrahydropyranyloxy-trans-1-octenyl]-3α-(2'-propenyl)-tetrahyropyran, a formula XIX compound.

D. To a solution of 5.2 g. of the reaction product of part C above in 50 ml. of dry tetrahydrofuran at 0° C. under a nitrogen atmosphere is added with stirring 10 ml. of disiamylborane (bis(1,2-dimethylpropyl)borane), 1M. in tetrahydrofuran. After 1 hr. at 0° C. there is added one ml. of water and (cautiously) a solution of one ml. of 50 percent aqueous sodium hydroxide in 20 ml. of methanol. To this mixture is added 15 ml. of 15 percent hydrogen peroxide, maintaining the reaction temperature below 40° C. After stirring for one hr at about 25° C. the mixture is shaken with brine and ethyl acetate. The organic phase is then washed with brine, dried and concentrated. The residue is then taken up in xylene and then concentrated again under reduced pressure. The product is then chromatographed on silica gel yielding a formula XX product: 6α-methoxy-4α-hydroxy-2β-[(3RS)-3-tetrahydropyranyloxy-trans-1-octenyl]-3α-(3-hydroxypropyl)-tetrahydropyran.

E. To a solution of 21.3 g. of the reaction product of part D above, 190 ml. of tetrahydrofuran, and 100 ml. of hexamethyldisilizane at ambient temperature is added with stirring 25 ml. of trimethylsilyl chloride. The resulting mixture is then allowed to stand at ambient temperature until silica gel TLC indicates the formation of the bis-(trimethylsilyl) derivative is complete. Thereupon crude product is concentrated under reduced pressure and the residue diluted with 250 ml. of dry benzene. This benzene containing mixture is then filtered, the solids washed with benzene, and the filtrate and washings combined and concentrated under reduced pressure to yield a formula XXI compound: 6α-methoxy-4α-trimethylsilyloxy-2β-[(3RS)-3-tetrahydropyranyloxy-trans-1-octenyl]-3α-(3-trimethylsilyloxypropyl)-tetrahydropyran.

F. To a solution of 100 ml. of dry methylene chloride in 6.2 ml. of pyridine at 15° C. is added with stirring 3.09 g. of dried chromium trioxide. This mixture is then stirred at 20°-23° C. for 30 min. and thereafter cooled to 15° C. To this cooled mixture is then added a solution of 2.3 g. of the reaction product of part E above in 15 ml. of methylene chloride. The resulting mixture is then stirred at ambient temperature for 30 min. Benzene (25 ml. and 3 g. of diatomaceous earth (Celite) are added to the mixture. The resulting mixture is then filtered through a bed of diatomaceous earth (Celite) and acid washed silica gel. The resulting solids are then washed with ethyl acetate and the filtrate and washings combined and concentrated under reduced pressure at ambient temperature to a residue which is mixed with ethyl acetate and filtered by the method described above. This second filtrate and ethyl acetate washings are then combined and concentrated under reduced pressure at about 25° C., preparing the formula XXXII compound: 6α-methoxy-4α-trimethylsilyloxy-2β-[(3RS)-3-tetrahydropyranyloxy-trans-1-octenyl]-3α-(3-oxopropyl)tetrahydropyran.

G. The reaction product of part F is reacted with a mixture of tetrahydrofuran, and acetic acid (1:3:6) at 40° C. for 4 hours. Thereafter the resulting mixture is diluted with water, freeze-dried, extracted with ethyl acetate, washed, dried, and concentrated to yield the formula XXIII lactol.

H. Following the procedure of Example 1, part D, but employing 3-carboxypropyltriphenylphosphonium bromide in place of 4,4-difluoro-4-carboxybutyltriphenylphosphonium bromide the reaction product of part G is transformed to a formula XXIV compound. Purification and separation of mixed C-15 epimers on silica gel chromatography yields 11-deoxy-11α-methoxy-cis-4,5-didehydro-TXB$_1$.

Following the procedure of Example 1, parts E, F, and G, there are prepared the various title products.

EXAMPLE 6

5-Oxa-TXB$_1$ (Formula XXXII: R$_1$, R$_3$ and R$_4$ of the L$_1$ moiety, M$_5$, and R$_6$ are all hydrogen, Z$_4$ is CH$_2$—O—(CH$_2$)$_3$—, Y$_1$ is trans—CH═CH—, and R$_7$ is n-butyl) its 15-epimer, the 11α-methyl acetals thereof, or methyl esters thereof.

Refer to Chart A (parts I, III, and V).

A. A mixture of the reaction mixture of Example 5, part A (6.3 g.) and 15 ml. of 95 percent ethanol is treated at 0° C., with stirring, with a solution of sodium borohydride (0.6 g.) in 10 ml. of water. The borohydride is added over a period of about one min. The resulting mixture is then stirred at 0° C. for 10 min. and shaken with 20 ml. of water, 250 ml. of ethyl acetate, and 150 ml. of brine. The organic phase is then washed with brine, dried, and concentrated under reduced pressure to yield a formula XXVI compound: 5α-methoxy-4α-hydroxy-2β-[(3RS)-3-tetrahydropyanyloxy-trans-1-octenyl]-3α-(2-hydroxyethyl)-tetrahydropyran.

B. A solution of potassium t-butoxide (1.77 g.) in 30 ml. of tetrahydrofuran is mixed at 0° C., with stirring, with a solution of 5.8 g. of the reaction product of part A above in 30 ml. of tetrahydrofuran. The resulting mixture is then stirred at 0° C. for 5 min. and thereafter 5 ml. of trimethyl ortho-4-bromobutyrate (see U.S. Pat. No. 3,864,387) is added. Stirring is continued at 0° C. for 2 hr. and at about 25° C. for 16 hr. To this mixture is then added 30 ml. of dimethylformamide and 0.5 g. of potassium-t-butoxide. The mixture is then stirred for 20 hr. Some of the solvent is then removed under reduced pressure and the residue shaken with water and diethyl ether dichloromethane (3:1). The organic phase is then washed with water and brine, dried, and concentrated. The residue containing the ortho ester is then dissolved in 60 ml. of methanol at 0° C. and treated with 15 ml. of cold water, containing 2 drops of concentrated hydrochloric acid. The resulting mixture is then stirred at 0° C. for 5 min. and shaken with 200 ml. of diethyl ether, 50 ml. of dichloromethane, and 200 ml. of brine. The organic phase is then washed with brine, dried, and concentrated under reduced pressure. The residue is then subjected to silica gel, separating mixed 15-epimer and yielding 11-deoxy-11α-methoxy-5-oxa-TXB$_1$, methyl ester, 15-tetrahydropyranyl ether or its 15-epimer.

C. Following the procedure of Example 5, part G, the reaction product of part B is transformed to 11-deoxy-11α-methoxy-5-oxa-TXB$_1$, methyl ester or its 15-epimer.

D. The methyl esters of part B above are saponfied by reaction with dilute aqueous alcoholic sodium hydroxide. Thereafter, the sodium salt thusly prepared is acidified wit dilute aqueous hydrochloric acid, yielding 11-deoxy-11α-methoxy-5-oxa-TXB$_1$ or its 15-epimer.

E. Following the procedure of Example 1, parts F, and G, there are prepared 5-oxa-TXB$_1$ or its 15-epimer or 5-oxa-TXB$_1$, methyl ester or its 15-epimer.

Following the procedures described in Example 1–6, and selecting the appropriate reactants and starting materials, there are prepared each of the various compounds described by formula XXXII.

Preparation 1

3,7-Inter-m-phenylene-3-oxa-16-phenoxy-4,5,6,17,18,19,20-heptanor-PGF$_{1\alpha}$ (Formula LVII: R$_1$, R$_3$, and R$_4$ or the L$_1$ moiety, and R$_5$ of the M$_1$ moiety are all hydrogen, Z$_3$ is oxa, Y$_1$ is trans—CH═CH—, g is one, and R$_7$ is phenoxy).

Refer to Chart C.

A. 3,7-Inter-m-phenylene-4,5,6-trinor-PGF$_{1\alpha}$, methyl ester (1 g.) in 200 ml. of methanol is cooled to 0° C. in an ice bath. A stream of ozone generated from a conventional ozone producing apparatus is passed through the mixture until the starting material is completely consumed. Thereupon the resulting ozonide is treated with dimethylsulfide, with stirring and allowed to warm to ambient temperature. The resulting product is washed and concentrated and the residue chromatographed yielding the formula LII aldehyde. About 4.5 g. of the formula LII aldehyde and 20 ml. of pyridine are subjected to dropwise addition of 4 g. of benzoyl chloride. The resulting mixture is then stirred at 25° C. for about 24 hr. The reaction mixture is then cooled to 0° C. and 5 ml. of water is added with stirring over about 10 min. Thereafter the resulting mixture is extracted with diethyl ether and the ethereal layers are washed with sodium bisulfate, sodium bicarbonate, and brine; dried over magnesium sulfate; filtered; and concentrated under reduced pressure to yield the formula LIII dibenzoate.

B. Following the procedure of Example 1, part A, but employing dimethyl 2-oxo-3-phenoxypropylphosphonate in place of dimethyl 2-oxo-heptylphosphonate, there is prepared the formula LIV product.

C. Following the procedure of Example 1, part B, the reaction product of part B above is transformed to the formula LVI compound.

D. The reaction product of part C above in a solution of 2 percent bicarbonate in methanol stirred at −25° C. for 24 hr. and the resulting mixture acidified to pH 4 or 5 with sodium bisulfate and concentrated to a residue. The residue is then extracted with ethyl acetate and the ethyl acetate extracts are washed with brine and dried over anhydrous magnesium sulfate. The resulting mixture is then concentrated under vacuum and the residue chromatographed on silica gel TLC to yield pure title free acid.

Preparation 2

3,7-Inter-m-phenylene-3-oxa-16-phenoxy-4,5,6,17,18,19,20-heptanor-PGF$_{1\alpha}$, 9,15-diacetate (formula L: R$_1$ and R$_3$ and R$_4$ of the L$_1$ moiety are hydrogen, Z$_1$ is

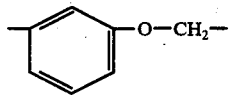

R$_{31}$ is benzoyl, Y$_1$ is trans—CH=CH—, R$_5$ of the M$_3$ moiety is methyl, R$_7$ is phenoxy and R$_{31}$ of the M$_3$ moiety is benzoyl).

Refer to Chart B.

A. A solution of the reaction product of Preparation 1 (800 mg.) and 1-butaneboronic acid (250 mg.) in 25ml. of methylene chloride is heated at reflux. After 15 min. the methylene chloride is allowed to distill off slowly and fresh methylene chloride is added each time the total volume is reduced to about one-half of the original volume. After 90 min. all of the methylene chloride is removed under reduced pressure yielding the formula XLI cyclic boronate of the starting material.

B. To the solution of about 0.8 g. of the reaction product of part A above in pyridine (5 ml.) is added acetic anhydride (2 ml.). The mixture is then stirred for about 4 hr. under a nitrogen atmosphere and thereafter water (50 ml.) is added and the resulting mixture stirred for an additional one hr. The second resulting mixture is then extracted with ethyl acetate and combined organic extracts are then washed, dried, and concentrated to yield the formula XLII 15-acetate.

C. The reaction product of part B above is dissolved in methanol in water (2:1) and a 30 percent methanolic solution of hydrogen peroxide (about 4 equivalents per equivalent of cyclic boronate) is added. The reaction mixture is maintained at ambient temperature, with stirring, until silica gel TLC indicates complete hydrolysis of the boronate ester.

D. A solution of 0.60 g. of the reaction product of part C above in 70 ml. of dry acetone is cooled to −20° C. Thereafter 2.8 ml. of trimethylsilyldiethylamine is added. After 30 min. another 2.8 ml. of trimethylsilyldiethylamine is added. After 1.5 hr. the reaction mixture is cooled to −70° C. and 150 ml. of cooled (−70° C.) diethyl ether is added. This mixture is then cooled and poured into 100 ml. of ice cold saturated sodium bicarbonate solution and extracted three times with diethyl ether. The combined ethereal extracts are then washed with ice cold saturated sodium bicarbonate and brine, dried over magnesium sulfate, and concentrated to yield the formula XLVIII 11-silylated compound.

E. As described in part B above, the reaction product of part E is acylated at C-9, yielding the formula XLIX compound.

F. The formula LXIX compound is then dissolved in 25 ml. of tetrahydrofuran and treated with a solution of tetra-n-butyl ammonium fluoride and tetrahydrofuran. This reaction mixture is then stirred at 65° C. for 2 hr. and thereafter cooled to ambient temperature. The resulting product is then concentrated and the reduced pressure, diluted with brine, and extracted with ethyl acetate. The organic extract is then washed with 2M aqueous potassium bisulfate and brine over magnesium sulfate. Concentrated under reduced pressure yields the title product.

Preparation 3

3,7-Inter-m-phenylene-3-oxa-16-phenoxy-4,5,6,17,18,19,20-heptanor, 15-acetate, 1,9-lactone (Formula LXIX: Z$_1$ is

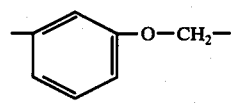

Y$_1$ is trans—CH=CH—, M$_3$ is

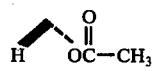

R$_3$ and R$_4$ of the L$_1$ moiety are hydrogen, and R$_7$ is phenoxy).

Refer to Chart B and Chart D (Part II).

A. 3,7-Inter-m-phenylene-3-oxa-4,5,6,17,18,19,20-heptanor-PGF$_{1\alpha}$, 15-acetate (Preparation 2, part C, 35 mg.), 39 mg. of triphenylphosphine, and 33 mg. of 2,2′-dipyridyldisulfide in 0.5 ml. of dry oxygen free benzene is stirred at ambient temperature for 18 hr. The mixture is thereafter diluted with 25 ml. of benzene and heated at reflux for 24 hr. Thereafter, pure product is isolated from the reaction mixture employing silica gel chromatographic separation.

Following the procedure of Preparations 2 and 3, each of the various PGF$_\alpha$-type compounds of formula XL of Chart B is transformed to a PGF$_\alpha$-9,15-diacylate of formula L or a PGF$_\alpha$, 15-aceylate, 1,9-lactone formula LXIX.

EXAMPLE 7

3,7-Inter-m-phenylene-3-oxa-16-phenoxy-4,5,6,17,18,19,20-heptanor-TXB$_1$, methyl ester (Formula LXVI: R$_1$ is methyl, Z$_1$ is

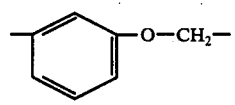

R$_6$ is hydrogen, Y$_1$ is trans—CH=CH—, R$_3$ and R$_4$ of the L$_1$ moiety and R$_5$ of the M$_1$ moiety are hydrogen, and R$_7$ is phenoxy).

Refer to Chart D.

A solution of 800 mg. of 3,7-inter-m-phenylene-3-oxa-16-phenoxy-4,5,6,17,18,19,20-tetranor-PGF$_{1\alpha}$, methyl ester 9,15-diacetate in 32 ml. of dry benzene is treated with 1.21 g. of lead-tetraacetate (recrystallized from acetic acid and dried under reduced pressure over potassium hydroxide) at 50° C. under a nitrogen atmosphere. Reaction conditions are maintained for about 70 min. The resulting mixture is then filtered through Celite and the filtrate washed with brine. The process of filtration is repeated and the second such filtrate is washed with brine, dried over sodium sulfate, and evaporated under reduced pressure at ambient temperature to yield {m-2-[(1'S)-3'-oxo-1'-hydroxypropyl]-(2S,3R,6R)-3,6-dihydroxy-7-phenoxy-trans-4-heptene-phenoxy}acetic acid, methyl ester, 3,6,1'-triacetate, a formula LXII compound.

B. The entire crude reaction product from part A is then dissolved in 16 ml. of dry methanol, 2.5 ml. of trimethyl orthoformate, and 175 mg. of pyridine hydrochloride. This mixture is then stirred over a nitrogen atmosphere for about 60 hr. at ambient temperature. Thereafter about 30 ml. of dry benzene is added and the methanol removed by concentration under reduced pressure. The resulting benzene-containing solution is then washed twice with brine, dried over sodium sulfate, and concentrated, yielding a residue.

This residue is then chromatographed on silica gel, eluting with 50 to 75 percent ethyl acetate in hexane. Fractions containing pure dimethylacetal of the reaction product of part A are combined, yielding the formula LXIII thromboxane intermediate.

C. A solution of 110 mg. of sodium and 10 ml. of dry methanol is prepared under a nitrogen atmosphere and to this mixture is added a solution of 420 mg. of the reaction product of part B and 5 ml. of dry methanol. The resulting mixture is then stirred at ambient temperature for 1.5 hr. and thereafter 0.5 ml. of acetic acid is added, followed by addition of benzene. Thereafter, the methanol is substantially removed by evaporation under reduced pressure. This benzene containing solution is then washed with brine, dried over sodium sulfate, and evaporated to yield a crude product which is then chromatographed on silica gel elution with two percent methanol and ethyl acetate. Fractions containing pure {m-2-[(1'S)-3'-oxa-1'-hydroxypropyl]-(2S,3R,6R)-3,6-dihydroxy-7-phenoxy-trans-4-heptenephenoxy}acetic acid, methyl ester, dimethylacetal are obtained.

D. A mixture of 187 mg. of the reaction product of part C under a nitrogen atmosphere is treated with a mixture of 4 ml. of acetic acid, 2 ml. of water, and 1 ml. of tetrahydrofuran for about 4 hr. Thereupon, the resulting mixture is stirred at ambient temperature under vacuum for about one hr. and the mixture then freeze dried and chromatographed on silica gel eluting with one percent methanol and ethyl acetate. There is thereby obtained 3,7-inter-m-phenylene-3-oxa-16-phenoxy-4,5,6,17,18,19,20-heptanor-11-deoxy-11α- and 11β-methoxy-TXB$_1$, methyl ester and 3,7-inter-m-phenylene-16-phenoxy-4,5,6,17,18,19,20-heptanor-TXB$_1$, methyl ester.

E. A solution of 300 mg. of the reaction product of part B in 5 ml. of dry methanol under nitrogen is treated at room temperature with 10 ml. of a sodium methoxide solution (120 mg. sodium dissolved in 10 ml. of methanol) for 45 min. Then 6 ml. of water is added and stirring is continued for 135 min. to hydrolyze the methyl ester. A solution of 2.5 ml. of 85 percent phosphoric acid in water is added and some of the methanol is removed at reduced pressure. The aqueous residue is then extracted with ethyl acetate. The extracts are dried over sodium sulfate and evaporated, yielding a free acid formula LXIV residue.

F. The residue of part E is dissolved in 12 ml. of tetrahydrofuran and treated with 9 ml. of water and 1 ml. of 85 percent phosphoric acid for 4.5 hr. at room temperature for about 35 hr. Thereafter the mixture is saturated with sodium chloride and extracted with ethyl acetate. The ethyl acetate extracts are then washed with brine, dried over sodium sulfate, and concentrated to a residue. This residue is then chromatographed on silica gel yielding 11-deoxy-11α- and 11β-methoxy 3,7-inter-m-phenylene-3-oxa-16-phenoxy-4,5,6,17,18,19,20-tetranor-TXB$_1$, and 3,7-inter-m-phenylene-3-oxa-16-phenoxy-4,5,6,17,18,19,20-tetranor-TXB$_1$.

EXAMPLE 8

3,7-Inter-m-phenylene-3-oxa-16-phenoxy-4,5,6,17,18,19,20-heptanor-TXB$_1$, methyl ester.

Refer to Chart D (Parts I and II).

A. A solution of the reaction product of Preparation 3 is transformed to the reaction product of Example 7, part C, following the procedure of Example 7, parts A, B, and C.

B. The title product is prepared following the procedure of Example 7, parts D, E, and F.

EXAMPLE 9

2-Decarboxy-2-hydroxymethyl-TXB$_2$ (Formula Z$_1$ is cis—CH=CH—(CH$_2$)$_3$—, Y$_1$ is trans—CH=CH—, R$_5$ of the M$_1$ moiety, R$_3$ and R$_5$ of the L$_1$ moiety, and R$_6$ are all hydrogen, and R$_7$ is n-butyl).

Refer to Chart A, 750 mg. of 11-deoxy-11α-methoxy-TXB$_2$, methyl ester dissolved in 50 ml. of diethyl ether are reacted with 500 mg. of lithium aluminum hydride at room temperature, with stirring. When the starting material is completely consumed (as indicated by thin layer chromatographic analysis) one ml. of water is cautiously added. Thereafter 0.8 ml. of 10 percent aqueous sodium hydroxide is added and the resulting mixture allowed to stir for 12 hr. Thereupon magnesium sulfate is added with stirring and the stirred mixture then filtered through magnesium sulfate and evaporated to a residue, which contains pure 2-decarboxy-2-hydroxymethyl-11-deoxy-11α-methoxy-TXB$_2$.

Following the procedure of Example 1, part F, the reaction product of the preceding paragraph is transformed to the title product.

Following the procedure of Example 9, but employing each of the various 11-deoxy-11α- or 11β-methoxy-TXB- or TXB-type compounds described above, there are prepared each of the various corresponding 2-decarboxy-2-hydroxymethyl-11-deoxy-11α- or 11β-methoxy-TXB- or TXB-type products.

Following the procedure of Example 7 or 8, but employing corresponding PGF$_{2α}$-type compounds in place of the starting material therein, there are prepared:

11-deoxy-11α-methoxy- or 11β-methoxy-TXB$_1$; TXB$_1$;
13,14-dihydro-11-deoxy-11α-methoxy- or 11β-methoxy-TXB$_1$;
13,14-dihydro-TXB$_1$;
11-deoxy-11α-methoxy- or 11β-methoxy-TXB$_2$;
13,14-dihydro-TXB$_2$;

or their respective 15-epimers and the methyl esters thereof.

Following the procedure of Example 7, but employing a corresponding PGFα starting material as described above, there are prepared 11-deoxy-11α-methoxy-TXB$_2$-, 11-deoxy-11β-methoxy-TXB$_2$-, 11-deoxy-11α-methoxy-TXB$_1$-, 11-deoxy-11β-methoxy-TXB$_1$-, TXB$_2$-, or TXB$_1$-type compounds, in free acid or methyl ester form, or the 15-epimers thereof, which exhibit the following functional characteristics:

16-Methyl-;
16,16-Dimethyl-;
16-Fluoro-;
16,16-Difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
16-Methyl-16-phenoxy-18,19,20-trinor-;
15,16-Dimethyl-;
15,16,16-trimethyl-;
16-fluoro-15-methyl-;
16,16-difluoro-15-methyl-;
17-phenyl-18,19,20-trinor-15-methyl-;
17-(m-trifluoromethylphenyl)-18,19,20-trinor-15-methyl-;
17-(m-chlorophenyl)-18,19,20-trinor-15-methyl-;
17-(p-fluorophenyl)-18,19,20-trinor-15-methyl-;
16-methyl-17-phenyl-18,19,20-trinor-15-methyl-;
15,16,16-trimethyl-17-phenyl-18,19,20-trinor-;
16-fluoro-17-phenyl-18,19,20-trinor-15-methyl-;
16,16-difluoro-17-phenyl-18,19,20-trinor-15-methyl-;
15-phenoxy-17,18,19,20-tetranor-15-methyl-;
16-(m-trifluoromethylphenoxy)-17,18,19,20-tetranor-15-methyl-;
16-(m-chlorophenoxy)-17,18,19,20-tetranor-15-methyl-;
16-phenoxy-18,19,20-trinor-15-methyl-;
15,16-dimethyl-16-phenoxy-18,19,20-trinor-;
13,14-Dihydro-;
16-Methyl-13,14-dihydro-;
16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
2,2-Difluoro-;
2,2-Difluoro-16-methyl-;
2,2-Difluoro-16,16-dimethyl-;
2,2-Difluoro-16-fluoro-;
2,2-Difluoro-16,16-difluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-dimethyl-17-phenyl-18,19,20-trinor-;
2,2-Difluoro-16-fluoro-17-phenyl-18,19,20-trinor-;
2,2-Difluoro-16,16-difluoro-17-phenyl-18,19,20-trinor-;
2,2-Difluoro-16-phenoxy-17,18,19,20-tetranor-;
2,2-Difluoro-16-(m-trifluoromethylphenoxy)-17,18,19,20-tetranor-;
2,2-Difluoro-16-(m-chlorophenoxy)-17,18,19,20-tetranor-;
2,2-Difluoro-16-(p-fluorophenoxy)-17,18,19,20-tetranor-;
2,2-Difluoro-16-phenoxy-18,19,20-trinor-;
2,2-Difluoro-16-methyl-16-phenoxy-18,19,20-trinor-;
13,14-dihydro-15-methyl-;
15,16-dimethyl-13,14-dihydro-;
15,16,16-trimethyl-13,14-dihydro-;
16-fluoro-13,14-dihydro-15-methyl-;
16,16-difluoro-13,14-dihydro-15-methyl-;
17-phenyl-18,19,20-trinor-13,14-dihydro-15-methyl-;
17-(m-trifluoromethylphenyl)-18,19,20-trinor-13,14-dihydro-15-methyl-;
17-(m-chlorophenyl)-18,19,20-trinor-13,14-dihydro-15-methyl-;
17-(p-fluorophenyl)-18,19,20-trinor-13,14-dihydro-15-methyl-;
15,16-dimethyl-17-phenyl-18,19,20-trinor-13,14-dihydro-;
15,16,16-trimethyl-17-phenyl-18,19,20-trinor-13,14-dihydro-;
16-fluoro-17-phenyl-18,19,20-trinor-13,14-dihydro-15-methyl-;
16,16-difluoro-17-phenyl-18,19,20-trinor-13,14-dihydro-15-methyl-;
16-phenoxy-17,18,19,20-tetranor-13,14-dihydro-15-methyl-;
16-(m-trifluoromethylphenoxy)-17,18,19,20-tetranor-13,14-dihydro-15-methyl-;
16-(m-chlorophenoxy)-17,18,19,20-tetranor-13,14-dihydro-15-methyl-;
16-(p-fluorophenoxy)-y)-17,18,19,20-tetranor-13,14-dihydro-15-methyl-;
16-Phenoxy-18,19,20-trinor-13,14-dihydro-15-methyl-;
15,16-Dimethyl-16-phenoxy-18,19,20-trinor-13,14-dihydro-;
2,2-Difluoro-16-methyl-16-phenoxy-18,19,20-trinor-;
2,2-difluoro-15-methyl-15,16-dimethyl-;
2,2-difluoro-15,16,16-trimethyl-;
2,2-difluoro-15-methyl-;
2,2-difluoro-16,16-difluoro-15-methyl-;
2,2-difluoro-17-phenyl-18,19,20-trinor-15-methyl-;
2,2-difluoro-17-(m-trifluoromethylphenyl)-18,19,20-trinor-15-methyl-;
2,2-difluoro-17-(m-chlorophenyl)-18,19,20-trinor-15-methyl-;
2,2-difluoro-17-(p-fluorophenyl)-18,19,20-trinor-15-methyl-;
2,2-difluoro-15,16-dimethyl-17-phenyl-18,19,20-trinor-;
2,2-difluoro-15,16,16-trimethyl-17-phenyl-18,19,20-trinor-;
2,2-difluoro-16-fluoro-17-phenyl-18,19,20-trinor-15-methyl-;

2,2-difluoro-16,16-difluoro-17-phenyl-18,19,20-trinor-15-methyl-;
2,2-difluoro-16-phenoxy-17,18,19,20-tetranor-15-methyl-;
2,2-difluoro-16-(m-chlorophenoxy)-17,18,19,20-tetranor-15-methyl-;
2,2-difluoro-16-phenoxy-18,19,20-trinor-15-methyl-;
2,2-difluoro-15,16-dimethyl-16-phenoxy-18,19,20-trinor-;
2,2-Difluoro-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;
2,2-Difluoro-17-phenyl-18,19,20-trinor-13,14-dihydro-;
2,2-Difluoro-17-(m-trifluoromethylphenyl)-18,19,20-trinor-13,14-dihydro-;
2,2-Difluoro-17-(m-chlorophenyl)-18,19,20-trinor-13,14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2,16-Trifluoro-17-phenyl-18,19,20-trinor-13,14-dihydro-;
2,2,16,16-Tetrafluoro-17-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy(-17,18,19,20-tetranor-13,14-dihydro-;
2,2-Difluoro-16-(m-chlorophenoxy)-17,18,19,20-tetranor-13,14-dihydro-;
2,2-Difluoro-16-(p-fluorophenoxy(-17,18,19,20-tetranor-13,14-dihydro-;
2,2-difluoro-16-phenoxy-18,19,20-trinor-13,14-dihydro-;
2,2-difluoro-16-methyl-16-phenoxy-18,19,20-trinor-13,14-dihydro-;
2,2-difluoro-13,14-dihydro-15-methyl-;
2,2-difluoro-15,16-dimethyl-13,14-dihydro-;
2,2-difluoro-15,16,17-trimethyl-13,14-dihydro-;
2,2,16-trifluoro-13,14-dihydro-15-methyl-;
2,2,16,16-tetrafluoro-13,14-dihydro-15-methyl-;
2,2-difluoro-17-phenyl-18,19,20-trinor-13,14-dihydro-15-methyl-;
2,2-difluoro-17-(m-trifluoromethylphenyl)-18,19,20-trinor-13,14-dihydro-15-methyl-;
2,2-difluoro-17-(m-chlorophenyl)-18,19,20-trinor-13,14-dihydro-15-methyl-;
2,2-difluoro-17-(p-fluorophenyl)-18,19,20-trinor-13,14-dihydro-15-methyl-;
2,2-difluoro-15,16-dimethyl-17-phenyl-18,19,20-trinor-13,14-dihydro-;
2,2-difluoro-15,16,16-trimethyl-17-phenyl-18,19,20-trinor-13,14-dihydro-;
2,2,16-trifluoro-17-phenyl-18,19,20-trinor-13,14-dihydro-15-methyl-;
2,2,16,16-tetrafluoro-17-phenyl-18,19,20-trinor-13,14-dihydro-15-methyl-;
2,2-difluoro-16-phenoxy-17,18,19,20-tetranor-13,14-dihydro-15-methyl-;
2,2-difluoro-16-(m-trifluoromethylphenoxy)-17,18,19,20-tetranor-13,14-dihydro-15-methyl-;
2,2-difluoro-16-(m-chlorophenoxy)-17,18,19,20-tetranor-13,14-dihydro-15-methyl-;
2,2-difluoro-16-(p-fluorophenoxy)-17,18,19,20-tetranor-13,14-dihydro-15-methyl-;
2,2-difluoro-16-phenoxy-18,19,20-trinor-13,14-dihydro-15-methyl-;
2,2-difluoro-15,16-dimethyl-16-phenoxy-18,19,20-trinor-13,14-dihydro-.

Following the procedure of Example 7 or 8, but employing corresponding starting material as described above there are prepared 11-deoxy-11α-methoxy- or 11β-methoxy-TXB$_1$- or TXB$_1$-type compounds, in free acid or methyl ester form, or the respective 15-epimers thereof, which exhibit the following functional characteristics;

3,7-inter-m-phenylene-3-oxa-4,5,6-trinor-;
3,7-inter-m-phenylene-3-oxa-4,5,6-trinor-16-methyl-;
3,7-inter-m-phenylene-3-oxa-4,5,6-trinor-16,16-dimethyl-;
3,7-inter-m-phenylene-3-oxa-4,5,6-trinor-16-fluoro-;
3,7-inter-m-phenylene-3-oxa-4,5,6-trinor-16,16-difluoro-;
3,7-inter-m-phenylene-3-oxa-17-phenyl-4,5,6,18,19,20-hexanor-;
3,7-inter-m-phenylene-3-oxa-17-(m-trifluoromethylphenyl)-4,5,6,18,19,20-hexanor-;
3,7-inter-m-phenylene-3-oxa-17-(m-chlorophenyl)-4,5,6,18,19,20-hexanor-;
3,7-inter-m-phenylene-3-oxa-17-(p-fluorophenyl)-4,5,6,18,19,20-hexanor-;
3,7-inter-m-phenylene-3-oxa-16-methyl-17-phenyl-4,5,6,18,19,20-hexanor-;
3,7-inter-m-phenylene-3-oxa-16,16-dimethyl-17-phenyl-4,5,6,18,19,20-hexanor-;
3,7-inter-m-phenylene-3-oxa-16-fluoro-17-phenyl-4,5,6,18,19,20-hexanor-;
3,7-inter-m-phenylene-3-oxa-16,16-difluoro-17-phenyl-4,5,6,18,19,20-hexanor-;
3,7-inter-m-phenylene-3-oxa-16-phenoxy-4,5,6,17,18,19,20-heptanor-;
3,7-inter-m-phenylene-3-oxa-16-(m-trifluoromethylphenoxy)-4,5,6,17,18,19,20-heptanor-;
3,7-inter-m-phenylene-3-oxa-16-(m-chlorophenoxy)-4,5,6,17,18,19,20-heptanor-;
3,7-inter-m-phenylene-3-oxa-4,5,6-trinor-16-(p-fluorophenoxy)-4,5,6,17,18,19,20-heptanor-;
3,7-inter-m-phenylene-3-oxa-16-phenoxy-4,5,6,18,19,20-hexanor-;
3,7-inter-m-phenylene-3-oxa-4,5,6-trinor-16-methyl-16-phenoxy-4,5,6,18,19,20-hexanor-;
3,7-inter-m-phenylene-3-oxa-4,5,6-trinor-15-methyl-;
3,7-inter-m-phenylene-3-oxa-4,5,6-trinor-15,16-dimethyl-;
3,7-inter-m-phenylene-3-oxa-4,5,6-trinor-15,16,16-trimethyl-;
3,7-inter-m-phenylene-3-oxa-4,5,6-trinor-16-fluoro15-methyl-;
3,7-inter-m-phenylene-3-oxa-4,5,6-trinor-16,16-difluoro-15-methyl-;
3,7-inter-m-phenylene-3-oxa-17-phenyl-4,5,6,18,19,20-hexanor-15-methyl-;
3,7-inter-m-phenylene-3-oxa-17-(m-trifluoromethylphenyl)-4,5,6,18,19,20-hexanor-15-methyl-;
3,7-inter-m-phenylene-3-oxa-17-(m-chlorophenyl)-4,5,6,18,19,20-hexanor-15-methyl-;
3,7-inter-m-phenylene-3-oxa-17-(p-fluorophenyl)-4,5,6,18,19,20-hexanor-15-methyl-;

3,7-inter-m-phenylene-3-oxa-15,16-dimethyl-17-phenyl-4,5,6,18,19,20-hexanor-;
3,7-inter-m-phenylene-3oxa-15,16,16-trimethyl-17-phenyl-4,5,6,18,19,20-hexanor-;
3,7-inter-m-phenylene-3-oxa-16-fluoro-17-phenyl-4,5,6,18,19,20-hexanor-15-methyl-;
3,7-inter-m-phenylene-3-oxa-16,16-difluoro-17-phenyl-4,5,6,18,19,20-hexanor-15-methyl-;
3,7-inter-m-phenylene-3-oxa-16-phenoxy-4,5,6,17,18,19,20-heptanor-15-methyl-;
3,7-inter-m-phenylene-3-oxa-16-(m-trifluoromethylphenoxy)-4,5,6,17,18,19,20-heptanor-15-methyl-;
3,7-inter-m-phenylene-3oxa-16-(m-chlorophenoxy)-4,5,6,17,18,19,20-heptanor-15-methyl-;
3,7-inter-m-phenylene-3-oxa-16phenoxy-4,5,6,18,19,20-hexanor-15-methyl-;
3,7-inter-m-phenylene-3-oxa-15,16-dimethyl-16-phenoxy-4,5,6,18,19,20-hexanor-;
3,7-inter-m-phenylene-3-oxa-4,5,6-trinor-13,14-dihydro-;
3,7-inter-m-phenylene-3-oxa-4,5,6-trinor-16-methyl-13,14-dihydro-;
3,7-inter-m-phenylene-3-oxa-4,5,6-trinor-16,16-dimethyl-13,14-dihydro-;
3,7-inter-m-phenylene-3-oxa-4,5,6-trinor-16-fluoro-13,14-dihydro-;
3,7-inter-m-phenylene-3-oxa-4,5,6-trinor-16,16-difluoro-13,14-dihydro-;
3,7-inter-m-phenylene-3-oxa-17-phenyl-4,5,6,18,19,20-trinor-13,14-dihydro-;
3,7-inter-m-phenylene-3-oxa-17-(m-trifluoromethylphenyl)-4,5,6,18,19,20-hexanor-13,14-dihydro-;
3,7-inter-m-phenylene-3-oxa-17-(m-chlorophenyl)-4,5,6,18,19,20-hexanor-13,14-dihydro-;
3,7-inter-m-phenylene-3-oxa-17-(p-fluorophenyl)-4,5,6,18,19,20-hexanor-13,14-dihydro-;
3,7-inter-m-phenylene-3-oxa-16-methyl-17-phenyl-4,5,6,18,19,20-hexanor-13,14-dihydro-;
3,7-inter-m-phenylene-3-oxa-16,16-dimethyl-17-phenyl-4,5,6,18,19,20-hexanor-13,14-dihydro-;
3,7-inter-m-phenylene-3-oxa-16-fluoro-17-phenyl-4,5,6,18,19,20-hexanor-13,14-dihydro-;
3,7-Inter-m-phenylene-3-oxa-16,16-difluoro-17-phenyl-4,5,6,18,19,20-hexanor-13,14-dihydro-;
3,7-Inter-m-phenylene-3-oxa-16-phenoxy-4,5,6,17,18,19,20-heptanor-13,14-dihydro-;
3,7-Inter-m-phenylene-3-oxa-16-(m-trifluoromethylphenoxy)-4,5,6,17,18,19,20-heptanor-13,14-dihydro-;
3,7-Inter-m-phenylene-3-oxa-16-(m-chlorophenoxy)-4,5,6,17,18,19,20-heptanor-13,14-dihydro-;
3,7-Inter-m-phenylene-3-oxa-16-(p-fluorophenoxy)-4,5,6,17,18,19,20-heptanor-13,14-dihydro-;
3,7-Inter-m-phenylene-3-oxa-16-phenoxy-4,5,6,18,19,20-hexanor-13,14-dihydro-;
3,7-Inter-m-phenylene-3-oxa-16-methyl-16-phenoxy-4,5,6,18,19,20-hexanor-13,14-dihydro-;
3,7-inter-m-phenylene-3-oxa-4,5,6-trinor-13,14-dihydro-15-methyl-;
3,7-inter-m-phenylene-3-oxa-4,5,6-trinor-15,16-dimethyl-13,14-dihydro-;
3,7-inter-m-phenylene-3-oxa-4,5,6-trinor-15,16,16-trimethyl-13,14-dihydro-;
3,7-inter-m-phenylene-3-oxa-4,5,6-trinor-16-fluoro-13,14-dihydro-15-methyl-;
3,7-inter-m-phenylene-3-oxa-4,5,6-trinor-16,16-difluoro-13,14-dihydro-15-methyl-;
3,7-inter-m-phenylene-3-oxa-17-phenyl-4,5,6,18,19,20-trinor-13,14-dihydro-15-methyl-;
3,7-inter-m-phenylene-3-oxa-17-(m-trifluoromethylphenyl)-4,5,6,18,19,20-hexanor-13,14-dihydro-15-methyl-;
3,7-inter-m-phenylene-3-oxa-17-(m-chlorophenyl)-4,5,6,18,19,20-hexanor-13,14-dihydro-15-methyl-;
3,7-inter-m-phenylene-3-oxa-17-(p-fluorophenyl)-4,5,6,18,19,20-hexanor-13,14-dihydro-15-methyl-;
3,7-inter-m-phenylene-3-oxa-15,16-dimethyl-17-phenyl-4,5,6,18,19,20-hexanor-13,14-dihydro-;
3,7-inter-m-phenylene-3-oxa-15,16,16-trimethyl-17-phenyl-4,5,6,18,19,20-hexanor-13,14-dihydro-;
3,7-inter-m-phenylene-3-oxa-16-fluoro-17-phenyl-4,5,6,18,19,20-hexanor-13,14-dihydro-15-methyl-;
3,7-inter-m-phenylene-3-oxa-16,16-difluoro-17-phenyl-4,5,6,18,19,20-hexanor-13,14-dihydro-15-methyl-;
3,7-inter-m-phenylene-3-oxa-16-phenoxy-4,5,6,17,18,19,20-heptanor-13,14-dihydro-15-methyl-;
3,7-inter-m-phenylene-3-oxa-16-(m-trifluoromethylphenoxy)-4,5,6,17,18,19,20-heptanor-13,14-dihydro-15-methyl-;
3,7-inter-m-phenylene-3-oxa-16-(m-chlorophenoxy)-4,5,6,17,18,19,20-heptanor-13,14-dihydro-15-methyl-;
3,7-inter-m-phenylene-3-oxa-16-(p-fluorophenoxy)-4,5,6,17,18,19,20-heptanor-13,14-dihydro-15-methyl-;
3,7-inter-m-phenylene-3-oxa-16-phenoxy-4,5,6,18,19,20-hexanor-13,14-dihydro-15-methyl-;
3,7-inter-m-phenylene-3-oxa-15,16-dimethyl-16-phenoxy-4,5,6,18,19,20-hexanor-13,14-dihydro-;
3,7-inter-m-phenylene-4,5,6-trinor-;
3,7-Inter-m-phenylene-4,5,6-trinor-16-methyl-;
3,7-Inter-m-phenylene-4,5,6-trinor-16,16-dimethyl-;
3,7-Inter-m-phenylene-4,5,6-trinor-16-fluoro-;
3,7-Inter-m-phenylene-4,5,6-trinor-16,16-difluoro-;
3,7-Inter-m-phenylene-17-phenyl-4,5,6,18,19,20-hexanor-;
3,7-Inter-m-phenylene-17-(m-trifluoromethylphenyl)-4,5,6,18,19,20-hexanor-;
3,7-Inter-m-phenylene-17-(m-chlorophenyl)-4,5,6,18,19,20-hexanor-;
3,7-Inter-m-phenylene-17-(p-fluorophenyl)-4,5,6,18,19,20-hexanor-;
3,7-Inter-m-phenylene-16-methyl-17-phenyl-4,5,6,18,19,20-hexanor-;
3,7-Inter-m-phenylene-16,16-dimethyl-17-phenyl-4,5,6,18,19,20-hexanor-;
3,7-Inter-m-phenylene-16-fluoro-17-phenyl-4,5,6,18,19,20-hexanor-;
3,7-Inter-m-phenylene-16,16-difluoro-17-phenyl-4,5,6,18,19,20-hexanor-;
3,7-Inter-m-phenylene-16-phenoxy-17-phenyl-4,5,6,17,18,19,20-heptanor-;
3,7-Inter-m-phenylene-16-(m-trifluoromethylphenoxy)-4,5,6,17,18,19,20-heptanor-;
3,7-Inter-m-phenylene-16-(m-chlorophenoxy)-4,5,6,17,18,19,20-heptanor-;
3,7-Inter-m-phenylene-16-(p-fluorophenoxy)-4,5,6,17,18,19,20-heptanor-;
3,7-Inter-m-phenylene-6-phenoxy-4,5,6,18,19,20-hexanor-;
3,7-inter-m-phenylene-16-methyl-16-phenoxy-4,5,6,18,19,20-hexanor-;
3,7-Inter-m-phenylene-4,5,6-trinor-15-methyl-;
3,7-Inter-m-phenylene-4,5,6-trinor-15,16-dimethyl-;
3,7-Inter-m-phenylene-4,5,6-trinor-15,16,16-trimethyl-;
3,7-inter-m-phenylene-4,5,6-trinor-16-fluoro-15-methyl-;
3,7-inter-m-phenylene-4,5,6-trinor-16,16-difluoro-15-methyl-;

3,7-inter-m-phenylene-17-phenyl-4,5,6,18,19,20-hexanor-15-methyl-;
3,7-inter-m-phenylene-17-(m-trifluoromethylphenyl)-4,5,6,18,19,20-hexanor-15-methyl-;
3,7-inter-m-phenylene-17-(m-chlorophenyl)-4,5,6,18,19,20-hexanor-15-methyl-;
3,7-inter-m-phenylene-17-(p-fluorophenyl)-4,5,6,18,19,20-hexanor-15-methyl-;
3,7-inter-m-phenylene-15,16-dimethyl-17-phenyl-4,5,6,18,19,20-hexanor-;
3,7-inter-m-phenylene-15,16,16-trimethyl-17-phenyl-4,5,6,18,19,20-hexanor-;
3,7-inter-m-phenylene-16-fluoro-17-phenyl-4,5,6,18,19,20-hexanor-15-methyl-;
3,7-inter-m-phenylene-16,16-difluoro-17-phenyl-4,5,6,18,19,20-hexanor-15-methyl-;
3,7-inter-m-phenylene-16-phenoxy-4,5,6,17,18,19,20-heptanor-15-methyl-;
3,7-inter-m-phenylene-16-(m-trifluoromethylphenoxy)-4,5,6,17,18,19,20-heptanor-15-methyl-;
3,7-inter-m-phenylene-16-(m-chlorophenoxy)-4,5,6,17,18,19,20-heptanor-15-methyl-;
3,7-inter-m-phenoxy-4,5,6,18,19,20-hexanor-15-methyl-;
3,7-inter-m-phenylene-15,16-dimethyl-16-phenoxy-4,5,6,18,19,20-hexanor-;
3,7-inter-m-phenylene-4,5,6-trinor-13,14-dihydro-;
3,7-Inter-m-phenylene-4,5,6-trinor-16-methyl-13,14-dihydro-;
3,7-Inter-m-phenylene-4,5,6-trinor-16,16-dimethyl-13,14-dihydro-;
3,7-Inter-m-phenylene-4,5,6-trinor-16-fluoro-13,14-dihydro-;
3,7-Inter-m-phenylene-4,5,6-trinor-16,16-difluoro-13,14-dihydro-;
3,7-Inter-m-phenylene-17-phenyl-4,5,6,18,19,20-hexanor-13,14-dihydro-;
3,7-Inter-m-phenylene-17-(m-trifluoromethylphenyl)-4,5,6,18,19,20-hexanor-13,14-dihydro-;
3,7-Inter-m-phenylene-17-(m-chlorophenyl)-4,5,6,18,19,20-hexanor-13,14-dihydro-;
3,7-Inter-m-phenylene17-(p-fluorophenyl)-4,5,6,18,19,20-hexanor-13,14-dihydro-;
3,7-Inter-m-phenylene-16-methyl-17-phenyl-4,5,6,18,19,20-hexanor-13,14-dihydro-;
3,7-Inter-m-phenylene-16,16-dimethyl-17-phenyl-4,5,6,18,19,20-hexanor-13,14-dihydro-;
3,7-Inter-m-phenylene-16-fluoro-17-phenyl-4,5,6,18,19,20-hexanor-13,14-dihydro-;
3,7-Inter-m-phenylene-16,16-difluoro-17-phenyl-4,5,6,18,19,20-hexanor-13,14-dihydro-;
3,7-Inter-m-phenylene-16-phenoxy-4,5,6,17,18,19,20-heptanor-13,14-dihydro-;
3,7-Inter-m-phenylene-16-(m-trifluoromethylphenoxy)-4,5,6,17,18,19,20-heptanor-13,14-dihydro-;
3,7-Inter-m-phenylene-16-(m-chlorophenoxy)-4,5,6,17,18,19,20-heptanor-13,14-dihydro-;
3,7-Inter-m-phenylene-16-(p-fluorophenoxy)-4,5,6,17,18,19,20-heptanor-13,14-dihydro-;
3,7-Inter-m-phenylene-16-phenoxy-4,5,6,18,19,20-hexanor-13,14-dihydro-;
3,7-Inter-m-phenylene-16-methyl-16-phenoxy-4,5,6,18,19,20-hexanor-13,14-dihydro-;
3,7-inter-m-phenylene-4,5,6-trinor-13,14-dihydro-15-methyl-;
3,7-inter-m-phenylene-4,5,6-trinor-15,16-dimethyl-13,14-dihydro-;
3,7-inter-m-phenylene-4,5,6-trinor-15-,16,16-trimethyl-13,14-dihydro-;
3,7-inter-m-phenylene-4,5,6-trinor-16-fluoro-13,14-dihydro-15-methyl-;
3,7-inter-m-phenylene-4,5,6-trinor-16,16-difluoro13,14-dihydro-15-methyl-;
3,7-inter-m-phenylene-17-phenyl-4,5,6,18,19,20-hexanor-13,14-dihydro-15-methyl-;
3,7-inter-m-phenylene-17-(m-trifluoromethylphenyl)-4,5,6,18,19,20-hexanor-13,14-dihydro-15-methyl-;
3,7-inter-m-phenylene-17-(m-chlorophenyl)-4,5,6,18,19,20-hexanor-13,14-dihydro-15-methyl-;
3,7-inter-m-phenylene-17-(p-fluorophenyl)-4,5,6,18,19,20-hexanor-13,14-dihydro-15-methyl-;
3,7-inter-m-phenylene-15,16-dimethyl-17-phenyl-4,5,6,18,19,20-hexanor-13,14-dihydro-;
3,7-inter-m-phenylene-15,16,16-trimethyl-17-phenyl-4,5,6,18,19,20-hexanor-13,14-dihydro-;
3,7inter-m-phenylene-16-fluoro-17-phenyl-4,5,6,18,19,20-hexanor-13,14-dihydro-15-methyl-;
3,7-inter-m-phenylene-16,16-difluoro-17-phenyl-4,5,6,18,19,20-hexanor-13,14-dihydro-15-methyl-;
3,7-inter-m-phenylene-16-phenoxy-4,5,6,17,18,19,20-heptanor-13,14-dihydro-15-methyl-;
3,7-inter-m-phenylene-17-(m-trifluoromethylphenoxy)-4,5,6,17,18,19,20-heptanor-13,14-dihydro-15-methyl-;
3,7-inter-m-phenylene-16-(m-chlorophenoxy)-4,5,6,17,18,19,20-heptanor-13,14-dihydro-15-methyl-;
3,7-inter-m-phenylene-16-(p-fluorophenoxy)-4,5,6,17,18,19,20-heptanor-13,14-dihydro-15-methyl-;
3,7-inter-m-phenylene-16-phenoxy-4,5,6,18,19,20-hexanor-13,14-dihydro-15-methyl-;
3,7-inter-m-phenylene-15,16-dimethyl-16-phenoxy-4,5,6,18,19,20-hexanor-13,14-dihydro-;
5-Oxa-;
5-Oxa-16-methyl-;
5-Oxa-16,16-dimethyl-;
5-Oxa-16-fluoro-;
5-Oxa-16,16-difluoro-;
5-Oxa-17-phenyl-18,19,20-trinor-;
5-Oxa-17-(m-trifluoromethylphenyl)-18,19,20-trinor-;
5-Oxa-17-(m-chlorophenyl)-18,19,20-trinor-;
5-Oxa-17-(p-fluorophenyl)-18,19,20-trinor-;
5-Oxa-16-methyl-17-phenyl-18,19,20-trinor-;
5-Oxa-16,16-dimethyl-17-phenyl-18,19,20-trinor-;
5-Oxa-16-fluoro-17-phenyl-18,19,20-trinor-;
5-Oxa-16,16-difluoro-17-phenyl-18,19,20-trinor:;
5-Oxa-16-phenoxy-17,18,19,20-tetranor-;
5-Oxa-16-(m-trifluoromethylphenoxy)-17,18,19,20-tetranor-;
5-oxa-16-(m-chlorophenoxy)-17,18,19,20-tetranor-;
5-oxa-16-(p-fluorophenoxy)-17,18,19,20-tetranor-;
5-oxa-16-phenoxy-18,19,20-trinor-;
5-oxa-16-methyl-16-phenoxy-18,19,20-trinor-;
5-oxa-15-methyl-5-oxa-15,16-dimethyl-;
5-oxa-15,16,16-trimethyl-;
5-oxa-16-fluoro-15-methyl-;
5-oxa-16,16-difluoro-15-methyl-;
5-oxa-17-phenyl-18,19,20-trinor-15-methyl-;
5-oxa-17-(m-trifluoromethylphenyl)18,19,20-trinor-15-methyl-;
5-oxa-17-(m-chlorophenyl)-18,19,20-trinor-15-methyl-;
5-oxa-17-(p-fluorophenyl)-18,19,20-trinor-15-methyl-;
5-oxa-15,16-dimethyl-17-phenyl-18,19,20-trinor-;
5-oxa-15,16,16-trimethyl-17-phenyl-18,19,20-trinor-;
5-oxa-16-fluoro-17phenyl-18,19,20-trinor-15-methyl-;
5-oxa-16,16-difluoro-17-phenyl-18,19,20-trinor-15-methyl-;
5-oxa-16-phenoxy-17,18,19,20-tetranor-15-methyl-;

5-oxa-16-(m-trifluoromethylphenoxy)-17,18,19,20-tetranor-15-methyl-;
5-oxa-16-(m-chlorophenoxy)-17,18,19,20-tetranor-15-methyl-;
5-oxa-16-phenoxy-18,19,20-trinor-15-methyl-;
5-oxa-15,16-dimethyl-16-phenoxy-18,19,20-trinor-
5-oxa-13,14-dihydro-;
5-oxa-16-methyl-13,14-dihydro-;
5-oxa-16,16-dimethyl-13,14-dihydro-;
5-oxa-16-fluoro-13,14-dihydro-;
5-Oxa-16-fluoro-13,14-dihydro-;
5-Oxa-16,16-difluoro-13,14-dihydro-;
5-Oxa-17-phenyl-18,19,20-trinor-13,14-dihydro-;
54-Oxa-17-(m-trifluoromethylphenyl)-18,19,20-trinor-13,14-dihydro-;
5-Oxa-17-(m-chlorophenyl)-18,19,20-trinor-13,14-dihydro-;
5-Oxa-17-(p-fluorophenyl)-18,19,20-trinor-13,14-dihydro-;
5-Oxa-16-methyl-17-phenyl-18,19,20-trinor-13,14-dihydro-;
5-Oxa-16,16-Dimethyl-17-phenyl-18,19,20-trinor-13,14-dihydro-;
5-Oxa-16-fluoro-17-phenyl-18,19,20-trinor-13,14-dihydro-;
5-Oxa-16,16-difluoro-17-phenyl-18,19,20-trinor-13,14-dihydro-;
5-Oxa-16-phenoxy-17,18,19,20-tetranor-13,14-dihydro-;
5-Oxa-16-(m-trifluoromethylphenoxy)-17,18,19,20-tetranor-13,14-dihydro-;
5-Oxa-16-(m-chlorophenoxy)-17,18,19,20-tetranor-13,14-dihydro-;
5-Oxa-16-(p-fluorophenoxy)-17,18,19,20-tetranor-13,14-dihydro-;
5-Oxa-16-phenoxy-18,19,20-trinor-13,14-dihydro-;
5-Oxa-16-phenoxy-18,19,20-trinor-13,14-dihydro-;
5-oxo-16-(m-chlorophenoxy)-17,18,19,20-tetranor-15-methyl-;
5-oxa-16-pheoxy-18,19,20-trinor-15-methyl-;
5-oxa-15,16-dimethyl-16-phenoxy-18,19,20-trinor-13,14-didehydro-;
5-oxa-13,14-dihydro-15-methyl-;
5-oxa-15,16-dimethyl-13,14-dihydro-;
5-oxa-15,16,16-trimethyl-13,14-dihydro-;
5-oxa-16-fluoro-13,14-dihydro-15-methyl-;
5-oxa-16,16-difluoro-13,13-dihydro-15-methyl-;
5-oxa-17-phenyl-18,19,20-trinor-13,14-dihydro-15-methyl-;
5-oxa-17-(m-trifluoromethylphenyl)-18,19,20-trinor-13,14-dihydro-15-methyl-;
5-oxa-17-(m-chlorophenyl)-18,19,20-trinor-13,14-dihydro-15-methyl-;
5-oxa-17-(p-fluorophenyl)-18,19,20-trinor-13,14-dihydro-15-methyl-;
5-oxa-15,16-dimetyl-17-phenyl-18,19,20-trinor-13,14-dihydro-;
5-oxa-15,16,16-trimethyl-17-phenyl-18,19,20-trinor-13,14-dihydro-;
5-oxa-16-fluoro-17-phenyl-18,19,20-trinor-13,14-dihydro-15-methyl-;
5-oxa-16,16-difluoro-17-phenyl-18,19,20-trinor-13,14-dihydro-15-methyl-;
5-oxa-16-phenoxy-17,18,19,20-tetranor-13,14-dihydro-15-methyl-;
5-oxa-16-(m-trifluoromethylphenoxy)-17,18,19,20-tetranor-13,14-dihydro-15-methyl-;
5-oxa-16-(m-chlorophenoxy)-17,18,19,20-tetranor-13,14-dihydro-15-methyl-;
5-oxa-16-(p-fluorophenoxy)-17,18,19,20-tetranor-13,14-dihydro-15-methyl-;
5-oxa-16-phenoxy-18,19,20-trinor-13,14-dihydro-15-methyl-;
5-oxa-15,16-dimethyl-16-phenoxy-18,19,20-trinor-13,14-dihydro-;

EXAMPLE 10

$TXB_1$ 15-epi-$TXB_1$, 11-deoxy-11α-methoxy-$TXB_1$, 15-epi-11-deoxy-11α-methoxy-$TXB_1$, 11-deoxy-11α-methoxy-$TXB_1$, methyl ester, or 15-epi-11-deoxy-11α-methoxy-$TXB_1$, methyl ester.

Refer to Chart A (Part VI).

A. The formula XXXIV compound wherein $R_{34}$ is benzyl and $R_{33}$ is methyl (1.7 g.) dissolved in 17 ml. of toluene and 4 ml. of tetrahydrofuran is cooled under an argon atmosphere in a dry-ice acetone bath. To this cooled solution is added diisobutylaluminumhydride. The reaction is complete in about 30 min., and the reaction mixture is thereafter treated at −78° C. with 1.7 ml. of water (added dropwise) and allowed to warm to 25° C. The resulting mixture is then filtered and the solid washed with benzene. The combined filtrates are then washed with brine and the organic layer dried over magnesium sulfate. Concentration of the solution under reduced pressure yields 1.71 g. of a formula XXXV residue, which solidifies on standing. Silica gel TLC $R_f$ is 0.13 in ethyl acetate and Skellysolve B (40:60).

B. Sodium hydride (55 percent dispersion in oil), 2.9 g, is washed with n-hexane. To the residue is added 43 ml. of dry dimethylsulfoxide and the mixture heated to 65° C. for 2 hr. under an argon atmosphere. A resulting dark gray mixture is then cooled to 15° C. and maintained at that temperature while 15.4 g. of 4-carboxybutyltriphenylphosphonium bromide, dissolved 70 ml. of dry dimethylsulfoxide, is added during 15 min. The resulting mixture is then allowed to warm to 25° C. and stirred for one hr. The mixture is then cooled again to 15° C. and treated over a 10 min. period with 1.71 g. of the reaction product of part A above, dissolved in 13 ml. of dry dimethylsulfoxide. After one hr., 300 mg. of water is added while maintaining the reaction temperature below 20° C. The resultant mixture is then extracted with diethyl ether and the aqueous layer treated with 50 g. of ammonium chloride in 100 ml. of saturated brine. The resulting mixture is then extracted with ethyl acetate and the ethyl acetate layer dried over magnesium sulfate and concentrated under reduced pressure. the residue thusly obtained in then treted with excess ethereal diazomethane. The diethyl ether is then evaporated and the residue chromatographed over 200 g. of silica gel. Eluting with mixtures of ethyl acetate and Skellysolve B (40:60 and 50:50), pure formula XXXVI product wherein $R_1$ is methyl, g is one, $R_2$ is hydrogen, $R_{33}$ is methyl, and $R_{34}$ is benzyl, 2.02 g., is obtained. NMR absorptions are observed at 1.4–2.5, 3.35, 3.62, 4.58, 4.8-5.0, 5.2-5.6, and 7.3 δ. The mass spectrum indicates a parent peak 360.1929. Silica gel TLC $R_f$ is 0.41 in ethyl acetate and Skellysolve B (40:60).

C. The reaction product of part B (2.02 g.) is dissolved in 200 ml. of ethyl acetate. Thereafter 2 g. of a 5 percent palladium-on-carbon catalyst is added and the mixture hydrogenated at 40 pounds per square inch. Hydrogen uptake is monitored, and after 3 hr. an additional 2 g. of a 5 percent palladium-on-charcoal catalyst is added. Hydrogenation is then allowed to continue for 16 hr. whereupon an additional 2 g. of the above catalyst is added and the reaction conditions are maintained for an additional 24 hr. At this point, silica gel TLC indicates the reaction is complete and the catalyst is removed by filtration and the solvent evaporated under vacuum yielding 1.51 g. of the formula XXXVII product as an oil. NMR absorptions are observed at 0.8–2.1, 2.1–2.5, 2.8–3.2, 3.67, 3.5–4.2, and 4.8–5.0 δ. Infrared absorptions are observed at 3600, 2900, 1740, 1430, 1180, 1120, and 1050 cm.$^{-1}$. The mass spectrum indicates a parent peak at 417.2492. Silica gel TLC $R_f$ is 0.9 in ethyl acetate and Skellysolve B (40:60).

D. The reaction product of part C (1.51 g.) and 3.08 g. of dicyclohexylcarbodiimide are dissolved in 21 ml. of benzenne and the resulting solution stirred at 25° C. under an argon atomsphere. To this solution is then added 2.48 g. of one M phosphoric acid in dimethylsulfoxide. After 90 min. the reaction mixture is treated with 1.5 g. of oxalic acid, dissolved in 3 ml. of methanol. The resulting mixture is then stirred, such stirring continuing until about 15 min. after an initial vigorous bubbling has ceased. The mixture is then filtered and the collected solids washed with benzene. The combined benzene solutions are then washed with a 5 percent sodium bicarbonate solution, dried over sodium sulfate, and evaporated under reduced pressure to yield a crude formula XXXVIII aldehyde, as an oil.

This oil is then dissolved in 15 ml. of diethyl ether and the resulting solution treated with 33 ml. of 0.3 M tri-n-butyl-2-oxoheptylidine phosphorane and diethyl ether. After 1.5 hr. the reaction mixture is diluted with diethyl ether and resulting solution is washed with one N aqueous hydrochloric acid 5 percent aqueous sodium bicarbonate, and dried over magnesium sulfate. Concentration of the solution under reduced pressure yields crude 11-deoxy-11α-methoxy-15-dehydro-TXB$_1$, methyl ester, as an oil. This product is then chromatographed over 200 g. of silica gel, eluting with acetone and benzene (7:93), yielding 1.15 g. of pure product.

Silica gel TLC $R_f$ for the formula XXXVIII compound is 0.27 in acetone and benzene (10:90).

For the 15-dehydro-TXB$_1$ reaction product NMR absorptions are observed at 0.7–2.7, 3.35, 3,63, 4.8–4.95, 6.32, and 6.85 δ. Infrared absorptions are observed at 3600, 2900, 1740, 1675, 1450, 1430, 1360, 1180, 1120, 1150, and 1020 cm.$^{-1}$. The mass spectrum exhibits a parent peak at 366.2406. Silica gel TLC $R_f$ is 0.32 in acetone and benzene (10:90).

E. Dry zinc chloride (1.89 g.) is added to 25 ml. of dry tetrahydrofuran, and the mixture is stirred under an argon atmosphere at ambient temperature. To this mixture is added 0.5 g. of sodium borohydride. After 24 hr. this mixture is cooled to −20° C. and treated with 1.15 g. of the reaction product of part D in 10 ml. of dry tetrahydrofuran, the addition proceeding over 5 min. After 2 hr. at −20° C. the reaction is allowed to warm to ambient temperature and stirred 5 additional hr. The excess reducing agent is then destroyed by the careful addition of water. The reaction mixture is then poured into methyl acetate and extracted with brine, water, 5 percent aqueous sodium bicarbonate, and again with brine. The organic layer is then dried over magnesium sulfate and concentrated under reduced pressure yielding 1.12 g. of crude 11-deoxy-11α-methoxyTXB$_1$, methyl ester, and its 15-epimer. The epimeric alcohols are then purified by silica gel chromatographed, eluting with mixtures of acetone and benzene (5:95 to 20:80). Accordingly, there are obtained 479 mg. off the 15-epi compound and 536 mg. of (15S) compound. For the 15-epi alcohol NMR absorptions are observed at 0.65–2.5, 3.53, 3.63, 3.7–4.3, 4.7–4.95, and 5.6–5.85 δ. The mass spectrum exhibits a parent peak 544.3598. Silica gel TLC $R_f$ is 0.19 in acetone and benzene (10:90).

For the (15S) compound NMR absorptions are identical to those observed for the 15-epi compound. The high resolution mass spectrum exhibits a parent peak at 544.3608. Silica gel TLC $R_f$ is 0.14 in acetone and benzene (10.90).

F. The 15-epi reaction product of part E (400 mg.) in 400 ml. of 45 percent aqueous potassium hydroxide are dissolved in 12 ml. of methanol and the resulting solution stirred at ambient temperature under an argon atmosphere for 15 min. The resulting mixture is then diluted with water and saturated sodium chloride. The resulting solution is then acidified to pH 5 with 2N hydrochloric acid and extracted with ethyl acetate. The ethyl acetate extracts are then washed with brine, dried over magnesium sulfate, and evaporated under reduced pressure yielding 372 mg. of pure 11-deoxy-11α-meethoxy-15-epi-TXB$_1$. NMR absorptions are observed 3.36, 3.8–4.3, 3.75–3.95, and 5.4–5.9 δ. The mass spectrum exhibits a parent peak at 602.3854. Silica gel TLC $R_f$ is 0.14 in acetone and benzene (40:60) and 0.73 in the A-IX solvent system.

G. The reaction product of part F (365 mg.) and 0.18 ml. of 85 percent phosphoric acid are dissolved in 2.2 ml. of tetrahydrofuran and 1.8 ml. of water. The resulting solution is then warmed to 40° C. for 10 hr. The reaction mixture is then cooled and diluted with ethyl acetate and brine. The various layers are then separated and the aqueous layer extracted with ethyl acetate. The combined ethyl acetate solutions are then washed with brine, dried over magnesium sulfate, and evaporated under reduced pressure. The resulting residue is chromatographed on 30 g. of silica gel, eluting with ethyl acetate and Skellylosolve B (75:25) and ethyl acetate, yielding 273 ml. of 15-epi-TXB$_1$. Infrared absorptions are observed to 3350, 2900, 1710, 1370, 1240, 1100, 1040, 1070, 1020, and 970 cm.$^{-1}$. The mass spectrum exhibits a parent peak at 645.3860. Silica gel TLC $R_f$ is 0.50 in A-IX solvent system.

H. Following the procedure of part F, 400 mg. of the reaction product of part E is transformed to 11-deoxy-11α-methoxy-TXB$_1$. The NMR absorptions are observed at 3.38, 4.75–4.95, and 5.3–6.1 δ. The mass spectrum exhibits a parent peak 602,3851. Silica gel TLC $R_f$ is 0.22 in acetone and benzene (40:60) and 0.71 in the A-IX solvent system.

I. The reaction product of part 8 (370 mg.) is transformed to TXB$_1$ following the procedure described in part G above. Infrared absorptions are observed at 3400, 2950, 2875, 1715, 1240, 1110, 1040, 1020, and 970 cm.$^{-1}$. The mass spectrum exhibits a parent peak at 660.4087. Silica gel TLC $R_f$ is 0.46 in the A-IX solvent system.

We claim:
1. A thromboxane analog of the formula.

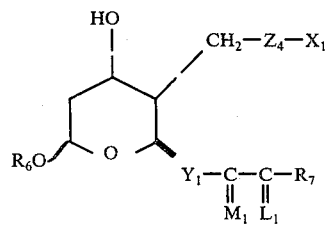

wherein $R_6$ is hydrogen or alkyl of one to 4 carbon atoms, inclusive;

wherein $M_1$ is

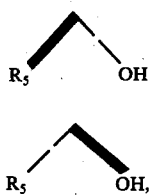

or

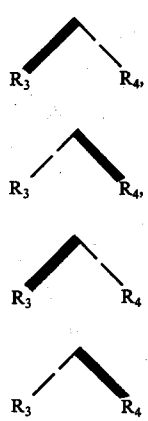

wherein $R_5$ is hydrogen or methyl;

wherein $L_1$ is

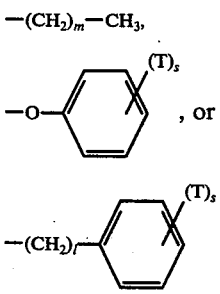

wherein $R_3$ and $R_4$ are hydrogen, methyl, or fluoro, being the same or different with the proviso that one of $R_3$ and $R_4$ is methyl only when the other is hydrogen or methyl;

wherein $Y_1$ is trans — CH=CH— or —$CH_2CH_2$—;

wherein $R_7$ is

—$(CH_2)_m$—$CH_3$, (1)

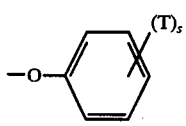, or (2)

(3)

wherein l is zero, one, two, or three;
wherein m is one to 5, inclusive, T is alkyl of one to 3 carbon atoms, inclusive, alkoxy of one to 3 carbon atoms, inclusive, chloro, fluoro, or trifluoroethyl, and s is one, two, or 3, the various T's being the same or different, with the proviso that not more than two T's are other then alkyl, with the further proviso that $R_7$ is only when $R_3$ and $R_4$ are hydrogen or methyl, being the same or different;

wherein $Z_4$ is
(1) cis—CH=CH—$CH_2$—$(CH_2)_g$—$CH_2$—,
(2) cis—CH=CH—$CH_2$—$(CH_2)_g$—$CF_2$—,
(3) cis—$CH_2$—CH=CH—$(CH_2)_g$—$CH_2$—,
(4) —$(CH_2)_3$—$(CH_2)_g$—$CH_2$—,
(5) —$(CH_2)_3$—$(CH_2)_g$—$CF_2$—,
(6) —$CH_2$—O—$CH_2$—$(CH_2)_g$—$CH_2$—, wherein g is one, or 3; and wherein $X_1$ is
(1) —$CH_2OH$, or
(2) —$COOR_1$, wherein $R_1$ is alkyl of one to 12 carbon atoms, inclusive, cycloalkyl of 3 to 10 carbon atoms, inclusive, aralkyl of 7 to 12 carbon atoms, inclusive, phenyl, phenyl substituted with one or two chloro, fluoro, or alkyl of one to 4 carbon atoms, inclusive, or a pharmacologically acceptable cation, with the overall proviso that $Z_4$ is cis—CH=CH—$(CH_2)_3$—$Y_1$ is trans—CH=CH—, $R_3$, $R_4$, and $R_5$ are all hydrogen, and $R_7$ is n-butyl, only when $X_1$ is —$CH_2OH$.

2. A thromboxane analog according to claim 1, wherein $R_6$ is alkyl of one to 4 carbon atoms, inclusive.

3. 11-Deoxy-11α-methoxy-$TXB_1$, a thromboxane analog according to claim 2.

4. A thromboxane analog according to claim 1, wherein $R_6$ is hydrogen.

5. A thromboxane analog according to claim 4, wherein $Z_4$ is —$(CH_2)_3$—$(CH_2)_g$—$CF_2$—.

6. 2,2-difluoro-$TXB_1$ a thromboxane annalog according to claim 5.

7. A thromboxane analog according to claim 4, wherein $Z_4$ is cis—CH=CH—$CH_2$—$(CH_2)_g$—$CF_2$—.

8. 2,2-Difluoro-$TXB_2$, a thromboxane analog according to claim 7.

9. A thromboxane analog according to claim 4, wherein $Z_4$ is cis—$CH_2$—CH=CH—$(CH_2)_g$—$CH_2$—.

10. cis-4,5-Didehydro-$TXB_1$, a thromboxane analog according to claim 9.

11. A thromboxane analog according to claim 4, wherein $Z_4$ is —$(CH_2)_3$—$(CH_2)_g$—$CH_2$—.

12. $TXB_1$, a thromboxane analog according to claim 11.

13. A thromboxane analog according to claim 4, wherein $Z_4$ is —$(CH_2)_2$—O—$(CH_2)_g$—$CH_2$—.

14. 5-Oxa-$TXB_1$, a thromboxane analog according to claim 13.

15. A thromboxane analog according to claim 4, wherein $Z_4$ is cis—CH=CH—$CH_2$—$(CH_2)_g$—$CH_2$—.

16. A thromboxane analog according to claim 15, wherein $X_1$ is —$CH_2OH$.

17. 2-Decarboxy-2-hydroxymethyl-$TXB_2$, a thromboxane analog according to claim 16.

18. A thromboxane analog according to claim 15, wherein $X_1$ is —$COOR_1$.

19. A thromboxane analog according to claim 18, wherein $M_1$ is

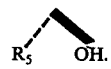

20. 15-epi-15-Methyl-$TXB_2$, a tjromboxane analog according to claim 19.

21. A thromboxane analog according to claim 18, wherein $M_1$ is

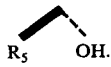

22. A thromboxane analog according to claim 21, wherein $R_7$ is

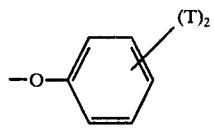

23. 17-Phenyl-18,19,20-trinor-TXB$_2$, a thromboxane analog according to claim 22.
24. A thromboxane analog according to claim 21, wherein $R_7$ is

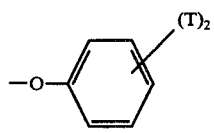

25. 16-Phenoxy-17,18,19,20-tetranor-TXB$_2$, as thromboxane analog according to claim 24.
26. A thromboxane analog according to claim 21, wherein $R_7$ is —(CH$_2$)$_m$—CH$_3$.
27. A thromboxane analog according to claim 26, wherein $m$ is 3.
28. A thromboxane analog according to claim 27, wherein $g$ is 3.
29. 2a,2b-Dihomo-TXB$_2$, a thromboxane analog according to claim 28.
30. A thromboxane analog according to claim 29, wherein $g$ is one.
31. A thrombonxane analog according to claim 30, wherein $Y_1$ is —CH$_2$CH$_2$—.
32. 13,14-Dihydro-TXB$_2$, a thromboxane analog according to claim 31.
33. A thromboxane analog according to claim 30, wherein $Y_1$ is trans—CH=CH—.

34. A thromboxane analog according to claim 33, wherein $R_5$ is methyl.
35. A thromboxane analog according to claim 34, wherein at least one of $R_3$ and $R_4$ is fluoro.
36. A thromboxane analog according to claim 35, wherein $R_3$ and $R_4$ are both fluoro.
37. 15-Methyl-16,16-difluoro-TXB$_2$, methyl ester, a thromboxane analog according to claim 36.
38. 15-Methyl-16,16-difluoro-TXB$_2$, a thromboxane analog according to claim 36.
39. A thromboxane analog according to claim 34, wherein at least one of $R_3$ and $R_4$ is methyl.
40. A thromboxane analog according to claim 39, wherein $R_3$ and $R_4$ are both methyl.
41. 15,16,16-Trimethyl-TXB$_2$, methyl ester, a thromboxane analog according to claim 40.
42. 15,16,16-Trimethyl-TXB$_2$, a thromboxane analog according to claim 40.
43. A thromboxane analog according to claim 34, wherein $R_3$ and $R_4$ are both hydrogen.
44. 15-Methyl-TXB$_2$, methyl ester, a thromboxane analog according to claim 43.
45. 15-Methyl-TXB$_2$a thromboxane analog according to claim 43.
46. A thromboxane analog according to claim 33, wherein $R_5$ is hydrogen.
47. A thromboxane analog according to claim 46, wherein at least one of $R_3$ and $R_4$ is fluoro.
48. A thromboxane analog according to claim 47, wherein $R_3$ and $R_4$ are both fluoro.
49. 16,16-Difluoro-TXB$_2$, methyl ester, a thromboxane analog according to claim 48.
50. 16,16-Difluoro-TXB$_2$, a thromboxane analog according to claim 48.
51. A thromboxane analog according to claim 46, wherein at least one of $R_3$ and $R_4$ is methyl.
52. A thromboxane analog according to claim 51, wherein $R_3$ and $R_4$ are both methyl.
53. 16,16-Dimethyl-TXB$_2$, methyl ester, a thromboxane analog according to claim 52.
54. 16,16-dimethyl-TXB$_2$, a thromboxane analog according to claim 52.

* * * * *

UNITED STATES PATENT OFFICE
CERTIFICATE OF CORRECTION

Patent No. 4,054,737          Dated 18 October 1977

Inventor(s)  Robert C. Kelly, et al.

It is certified that error appears in the above-identified patent and that said Letters Patent are hereby corrected as shown below:

Column 2, line 4, "prosanoic" should read -- prostanoic --; line 65, "Dye" should read -- Due --;
Column 3, line 26, "11-hydroxy" should read -- 11-hydroxyl --;

Column 18, line 2, "cis-Ch=CH-" should read -- cis-CH=CH- --; line 4, "-(CH$_2$)$_3$(CH$_2$)$_g$-CH$_2$-" should read -- -(CH$_2$)$_3$-(CH$_2$)$_g$-CH$_2$- --;
Column 19, lines 45-50, that portion of the formula reading

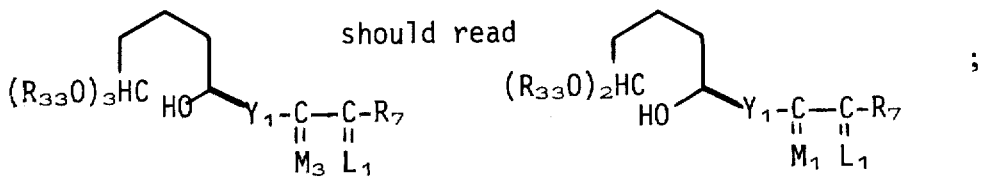

should read

Column 23, lines 41-42, "cis-CH=CH-(CH$_2$-(CH$_2$)$_g$-" should read -- cis-CH=CH-CH$_2$-(CH$_2$)$_g$- --;
Column 27, line 31, "injection of" should read -- injection or --
Column 38, lines 55-60, that portion of the formula reading

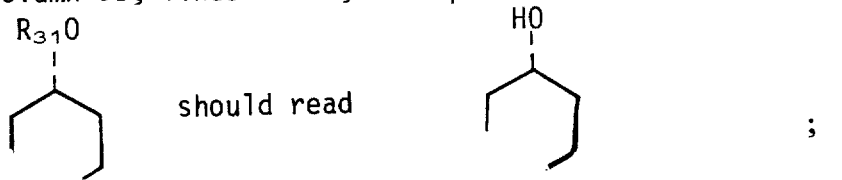

should read

UNITED STATES PATENT OFFICE
CERTIFICATE OF CORRECTION

Patent No. 4,054,737      Dated 18 October 1977

Inventor(s) Robert C. Kelly, et al.

It is certified that error appears in the above-identified patent and that said Letters Patent are hereby corrected as shown below:

Column 39, line 50, "-eR$_7$" should read -- -R$_7$ --;
Column 40, line 10, "-eR$_7$" should read -- -R$_7$ --;
Column 43, line 37, should include -- or --; line 68, "ay" should read -- any --;
Column 46, line 7, "(o-, m-, or p-)methoxy-m" should read -- (o-, m-, or p-)methoxyphenyl-, --;
Column 47, line 10, "corresonding" should read -- corresponding --; line 20, "and 6β-hydroxy" should read -- and 3β-hydroxy --;
Column 51, line 39, "or 5-ether" should read -- or 15-ether --;
Column 54, line 6, "triallyl," should read -- trialkyl, --; line 61 and 64, "Americal" should read -- American --; line 65, "formula LXVII" should read -- formula LXVIII --;
Column 63, line 2, "3.09 g" should read -- 3.9 g --;
Column 65, line 2, "2 percent bicarbonate" should read -- 2 percent potassium bicarbonate --;
Column 66, line 45, "15-aceylate," should read -- 15-acylate, --;
Column 74, line 58, "-6-phenoxy-" should read -- 16-phenoxy- --;
Column 75, line 23, "3,7-inter-m-phenoxy-" should read -- 3,7-inter-m-phenylene-16-phenoxy- --;
Column 77, line 14, "54-Oxa-" should read -- 5-Oxa- --;
Column 79, line 14, "atomsphere" should read -- atmosphere --;
Column 80, line 53, "1715, 1240," should read -- 1715, 1375, 1240, --;
Column 82, line 20, "cis-Ch=" should read -- cis-CH= --; line 65, "tjromboxane" should read -- thromboxane --.

Signed and Sealed this

Thirtieth Day of June 1981

[SEAL]

Attest:

RENE D. TEGTMEYER

*Attesting Officer*     *Acting Commissioner of Patents and Trademarks*